(12) United States Patent
Bärfacker et al.

(10) Patent No.: US 9,604,989 B2
(45) Date of Patent: *Mar. 28, 2017

(54) IMIDAZOPYRIDAZINES AS AKT KINASE INHIBITORS

(71) Applicant: Bayer Intellectual Property GmbH, Monheim (DE)

(72) Inventors: Lars Bärfacker, Oberhausen (DE); William Scott, Guilford, CT (US); Andrea Hägebarth, Berlin (DE); Stuart Ince, Berlin (DE); Hartmut Rehwinkel, Berlin (DE); Oliver Politz, Panketal OT Zepernick (DE); Roland Neuhaus, Berlin (DE); Hans Briem, Berlin (DE); Ulf Bömer, Glienicke (DE)

(73) Assignees: BAYER INTELLECTUAL PROPERTY GMBH, Monheim (DE); BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,205

(22) Filed: Jul. 6, 2015

(65) Prior Publication Data

US 2015/0368250 A1 Dec. 24, 2015

Related U.S. Application Data

(63) Continuation of application No. 14/007,427, filed as application No. PCT/EP2012/056300 on Apr. 5, 2012, now Pat. No. 9,206,185.

(60) Provisional application No. 61/472,732, filed on Apr. 7, 2011.

(51) Int. Cl.
C07D 487/04 (2006.01)
A61K 31/5025 (2006.01)
A61K 45/06 (2006.01)

(52) U.S. Cl.
CPC ........ *C07D 487/04* (2013.01); *A61K 31/5025* (2013.01); *A61K 45/06* (2013.01)

(58) Field of Classification Search
CPC .................... C07D 487/04; A61K 31/5025
USPC .......................................... 544/236; 514/248
See application file for complete search history.

(56) References Cited

U.S. PATENT DOCUMENTS 9,206,185 B2 * 12/2015 Barfacker ............ C07D 487/04

* cited by examiner

*Primary Examiner* — Kahsay Habte
(74) *Attorney, Agent, or Firm* — Nixon & Vanderhye P.C.

(57) ABSTRACT

The present invention relates to a method for the treatment of a cancer that is sensitive to Pi3K/Akt pathway inhibition by administering a therapeutically effective amount of a compound of formula (I)

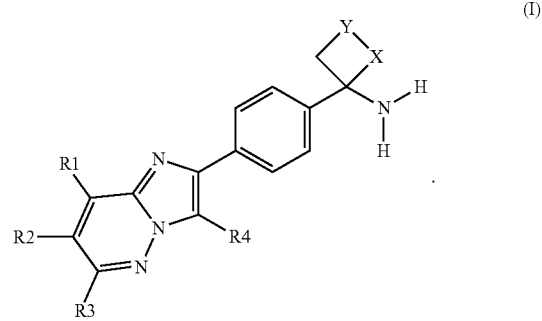

6 Claims, No Drawings

IMIDAZOPYRIDAZINES AS AKT KINASE INHIBITORS

FIELD OF APPLICATION OF THE INVENTION

The invention relates to substituted Imidazopyridazines, a process for their production and the use thereof.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particularly Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

Thus Akt seems to be a suitable target for the treatment of cancer.

Various publications exist relating to Akt inhibiting compounds such as e.g. WO 2009/148887, WO 2009/148916, WO2010104933, WO2010114780, WO2011033265.

In a recent disclosure, Y. Li et al (Bioorg. Med. Chem. Lett. 2009, 19, 834-836 and cited references therein) detail the difficulty in finding optimal Akt inhibitors. The potential application of Akt inhibitors in multiple disease settings, such as for example, cancer, makes the provision of new Akt inhibitors to those currently available highly desirable.

DESCRIPTION OF THE INVENTION

A solution to the above problem is the provision of alternative Akt inhibitors. It has now been found that the new Imidazopyridazine compounds, which are described in detail below, are Akt inhibitors suitable for the treatment of cancer.

In accordance with a first aspect, the invention relates to compounds of formula (I)

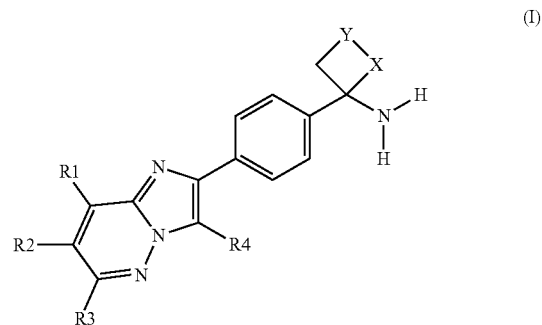

in which
R1 is hydrogen, hydroxy, NR5R6, halogen, cyano, CO(NR8R9), C(O)OR8, C(O)(1-6C-alkyl), NHC(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C- alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7-cycloalkyl, 3-7C-heterocyclyl, aryl, R2 is hydrogen, hydroxy, NR5R6, halogen, cyano, CO(NR8R9), C(O)OR8, C(O)(1-6C-alkyl), NHC(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl, R3 is hydrogen, hydroxy, NR5R6, halogen, cyano, CO(NR8R9), C(O)OR8, C(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, NHC(O)(1-6C-alkyl), 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl, R4 is phenyl which is optionally substituted one, two or three times, identically or differently, with a halogen atom;
R5 is hydrogen, 1-6C-alkyl,
R6 is hydrogen, 1-6C-alkyl,
R8 is hydrogen, 1-6C-alkyl which optionally is substituted with hydroxy,
R9 is hydrogen, 1-6C-alkyl,
R10 is hydrogen, 1-6C-alkyl,
R11 is hydrogen, 1-6C-alkyl,
X, Y is CH$_2$;
n is 0, 1, 2;
or an N-oxide, a salt, a tautomer or a stereoisomer of said compound, or a salt of said N-oxide, tautomer or stereoisomer.

In accordance with a second aspect, the invention relates to compounds of formula (I) according to claim 1, wherein
R1 is hydrogen, hydroxy, NR5R6, halogen, cyano, CO(NR8R9), C(O)OR8, C(O)(1-6C-alkyl), NHC(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl, R2 is hydrogen, hydroxy, NR5R6, halogen, cyano, CO(NR8R9), C(O)OR8, C(O)(1-6C-alkyl), NHC(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl, R3 is hydrogen, hydroxy, NR5R6, halogen, cyano, CO(NR8R9), C(O)OR8, C(O)(1-6C-alkyl), NHC(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl, R4 is phenyl which is optionally substituted one, two or three times, identically or differently, with a halogen atom;
R5 is hydrogen, 1-6C-alkyl,
R6 is hydrogen, 1-6C-alkyl,
R8 is hydrogen, 1-6C-alkyl,
R9 is hydrogen, 1-6C-alkyl,
R10 is hydrogen, 1-6C-alkyl,
R11 is hydrogen, 1-6C-alkyl,
X, Y is CH$_2$;
n is 0, 1, 2;
or an N-oxide, a salt, a tautomer or a stereoisomer of said compound, or a salt of said N-oxide, tautomer or stereoisomer.

Another aspect of the invention relates to compounds of formula (I) according to claim 1, wherein
R1 is hydrogen, hydroxy, NR5R6, halogen, cyano, CO(NR8R9), C(O)OR8, C(O)(1-3C-alkyl), NHC(O)(1-6C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, 2-3C-alkenyl, 2-3C-alkynyl, wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6-cycloalkyl, 3-6C-heterocyclyl, aryl, R2 is hydrogen, hydroxy, NR5R6, halogen, cyano, CO(NR8R9), C(O)OR8, C(O)(1-3C-alkyl), NHC(O)(1-3C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl, R3 is hydrogen, hydroxy, NR5R6, halogen, cyano, CO(NR8R9), C(O)OR8, C(O)(1-3C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, NHC(O)(1-3C-alkyl), 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl, R4 is phenyl which is optionally substituted one, two or three times, identically or differently, with a halogen atom;
R5 is hydrogen, 1-3C-alkyl,
R6 is hydrogen, 1-3C-alkyl,
R8 is hydrogen, 1-3C-alkyl which optionally is substituted with hydroxy,
R9 is hydrogen, 1-3C-alkyl,
R10 is hydrogen, 1-3C-alkyl,
R11 is hydrogen, 1-3C-alkyl,
X, Y is CH$_2$;
n is 0, 1, 2;
or an N-oxide, a salt, a tautomer or a stereoisomer of said compound, or a salt of said N-oxide, tautomer or stereoisomer.

Another aspect of the invention relates to compounds of formula (I) according to claim 1, wherein
R1 is hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl, aryl, heteroaryl,
wherein said group being optionally substituted, one or more times, identically or differently, with a substituent selected from:
halogen, 1-3C-alkyl, 1-3C-alkoxy, —C(O)OR10, 3-6-cycloalkyl, 3-6C-heterocyclyl, aryl, R2 is hydrogen, hydroxy, NR5R6, halogen, cyano, CO(NR8R9), C(O)OR8, C(O)(1-3C-alkyl), NHC(O)(1-3C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl, R3 is hydrogen, hydroxy, NR5R6, halogen, cyano, CO(NR8R9), C(O)OR8, C(O)(1-3C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, NHC(O)(1-3C-alkyl), 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl, R4 is phenyl which is optionally substituted one, two or three times, identically or differently, with a halogen atom;
R5 is hydrogen, 1-3C-alkyl,
R6 is hydrogen, 1-3C-alkyl,
R8 is hydrogen, 1-3C-alkyl which optionally is substituted with hydroxy,
R9 is hydrogen, 1-3C-alkyl,
R10 is hydrogen, 1-3C-alkyl,
R11 is hydrogen, 1-3C-alkyl,
X, Y is CH$_2$;
n is 0, 1, 2;
or an N-oxide, a salt, a tautomer or a stereoisomer of said compound, or a salt of said N-oxide, tautomer or stereoisomer.

A further aspect of the invention relates to compounds of formula (I) according to claim 1, wherein
R1 is OR7;
R2 is hydrogen,
R3 is C(O)NR8R9, C(O)OR8, halogen, 1-6C-alkyl, 1-6C-alkoxy,
R4 is phenyl which is optionally substituted one, two or three times, identically or differently, with a halogen atom;
R5 is hydrogen, 1-6C-alkyl,
R6 is hydrogen, 1-6C-alkyl,
R7 is 1-4C-haloalkyl,
R8 is hydrogen, 1-6C-alkyl,
R9 is hydrogen, 1-6C-alkyl,
R10 is hydrogen, 1-6C-alkyl,
R11 is hydrogen, 1-6C-alkyl,
X, Y is CH$_2$;
n is 0, 1, 2;

or an N-oxide, a salt, a tautomer or a stereoisomer of said compound, or a salt of said N-oxide, tautomer or stereoisomer.

A further aspect of the invention are compounds of formula (I) according to claim 1,
wherein
R1 is hydrogen, 1-4C-alkoxy,
R2 is hydrogen,
R3 is C(O)NH$_2$, C(O)OR8, halogen, 1-4C-alkyl, 1-4C-alkoxy,
R4 is phenyl which is optionally substituted one, two or three times, identically or differently, with a halogen atom;
R5 is hydrogen, 1-4C-alkyl,
R6 is hydrogen, 1-4C-alkyl,
R7 is 1-4C-haloalkyl,
R8 is hydrogen, 1-4C-alkyl,
R9 is hydrogen, 1-4C-alkyl,
R10 is hydrogen, 1-4C-alkyl,
R11 is hydrogen, 1-4C-alkyl,
X, Y is CH$_2$
n is 0, 1, 2;
or an N-oxide, a salt, a tautomer or a stereoisomer of said compound, or a salt of said N-oxide, tautomer or stereoisomer.

Another aspect of the invention are compounds of formula (I)
wherein
R1 is hydrogen, methoxy, ethoxy,
R2 is hydrogen,
R3 is C(O)NH$_2$, C(O)OR8, 1-3C-alkyl, bromine, methoxy, ethoxy,
R4 is phenyl which is optionally substituted one, two or three times, identically or differently, with a halogen atom;
R5 is hydrogen, 1-4C-alkyl,
R6 is hydrogen, 1-4C-alkyl,
R7 is 1-4C-haloalkyl,
R8 is hydrogen, 1-4C-alkyl,
R9 is hydrogen, 1-4C-alkyl,
R10 is hydrogen, 1-4C-alkyl,
R11 is hydrogen, 1-4C-alkyl,
X, Y is CH$_2$
n is 0, 1, 2; or an N-oxide, a salt, a tautomer or a stereoisomer of said compound, or a salt of said N-oxide, tautomer or stereoisomer A further aspect of the invention are compounds of formula (I)
wherein
R1 is hydrogen, 1-3C-alkoxy,
R2 is hydrogen
R3 is 1-3C-alkyl 1-3C-alkoxy, halogen, trifluoromethyl, C(O)NH2, COOR8,
R4 is phenyl
R8 is hydrogen, 1-4C-alkyl,
X, Y is CH2
or an N-oxide, a salt, a tautomer or a stereoisomer of said compound, or a salt of said N-oxide, tautomer or stereoisomer.

Another aspect of the invention are compounds of formula (I)
wherein
R1 is hydrogen, hydroxyl, amino, methoxy, ethoxy, butoxy, pyridine-3-yl, pyridine-4-yl, pyrazol-3-yl, 1-methyl-pyrazol-3-yl, imidazole-2-yl, methyl, propyl, —O—(CH$_2$)—O—CH$_3$, —O—CH$_2$-phenyl, —O—CH$_2$-cyclopropyl, —C(O)OCH$_3$, —C(O)—NHCH$_3$, —C(O)—NH$_2$, 4-fluorophenyl, —(CH$_2$)$_2$—C(O)OCH$_3$, cyclopropyl, —NH—C(O)CH$_3$,
R2 is hydrogen, methyl,
R3 is hydrogen, hydroxy, amino, methyl, ethyl, methoxy, ethoxy, —O—CH$_2$—C(O)OCH$_3$, —S—CH$_3$, —SO$_2$—CH$_3$, bromine, chlorine, trifluoromethyl, C(O)NH$_2$, COOH, C(O)OCH$_3$, C(O)OCH$_2$CH$_3$, C(O)NH$_2$, C(O)NHCH$_3$, C(O)N(CH$_3$)$_2$, C(O)NH(CH$_2$)$_2$—OH, —CH=CH$_2$, 4-fluorophenyl, NHC(O)CH$_3$, NHC(O)CF$_3$, NH—SO$_2$—CH$_3$, C(O)CH$_3$,
R4 is phenyl
X, Y is CH2
or an N-oxide, a salt, a tautomer or a stereoisomer of said compound, or a salt of said N-oxide, tautomer or stereoisomer.

Another aspect of the invention are compounds of formula (I)
wherein
R1 is hydrogen, methoxy,
R2 is hydrogen
R3 is methyl, ethyl, methoxy, bromine, trifluoromethyl, C(O)NH$_2$, COOH, C(O)OCH$_3$, C(O)OCH$_2$CH$_3$,
R4 is phenyl
X, Y is CH2
or an N-oxide, a salt, a tautomer or a stereoisomer of said compound, or a salt of said N-oxide, tautomer or stereoisomer.

In one aspect of the invention compounds of formula (I) as described above are selected from the group consisting of:

1-[4-(6-Methyl-3-phenylimidazo[1,2-b]pyridazin-2-yl)phenyl]-cyclobutanamine
1-[4-(6-Ethyl-3-phenylimidazo[1,2-b]pyridazin-2-yl)phenyl]-cyclobutanamine
1-{4-[3-Phenyl-6-(trifluoromethyl)imidazo[1,2-b]pyridazin-2-yl]phenyl}cyclobutanamine
Ethyl 2-[4-(1-aminocyclobutyl)phenyl]-3-phenylimidazo[1,2-b]pyridazine-6-carboxylate
2-[4-(1-Aminocyclobutyl)phenyl]-3-phenylimidazo[1,2-b]-pyridazine-6-carboxamide
1-[4-(6-Methyloxy-3-phenylimidazo[1,2-b]pyridazin-2-yl)-phenyl]cyclobutanamine
1-[4-(6-bromo-8-methyloxy-3-phenylimidazo[1,2-b]pyridazin-2-yl)phenyl]cyclobutanamine
2-[4-(1-aminocyclobutyl)phenyl]-3-phenylimidazo[1,2-b]-pyridazine-6-carboxylic acid
1-[4-(6,8-dimethyloxy-3-phenylimidazo[1,2-b]pyridazin-2-yl)-phenyl]cyclobutanamine
2-[4-(1-aminocyclobutyl)phenyl]-8-methoxy-3-phenyl-imidazo[1,2-b]pyridazine-6-carboxamide
1-[4-(8-Methoxy-3-phenylimidazo[1,2-b]pyridazin-2-yl)-phenyl]cyclobutanamine
Methyl 2-[4-(1-aminocyclobutyl)phenyl]-8-methoxy-3-phenyl-imidazo[1,2-b]pyridazine-6-carboxylate
1-[4-(6-Ethyl-8-methoxy-3-phenylimidazo[1,2-b]pyridazin-2-yl)phenyl]cyclobutanamine
1-{4-[6-Methoxy-3-phenyl-8-(pyridin-3-yl)imidazo[1,2-b]-pyridazin-2-yl]phenyl}cyclobutanami
1-{4-[6-Methoxy-3-phenyl-8-(1H-pyrazol-4-yl)imidazo[1,2-b]-pyridazin-2-yl]phenyl}cyclobutanamine HCl salt
1-[4-(6,8-Diethyl-3-phenylimidazo[1,2-b]pyridazin-2-yl)-phenyl]cyclobutanamine
1-[4-(6-Chloro-3-phenylimidazo[1,2-b]pyridazin-2-yl)phenyl]-cyclobutanamine
1-[4-(8-Methoxy-3-phenyl-6-vinylimidazo[1,2-b]pyridazin-2-yl)phenyl]cyclobutanamine
1-{4-[6-Chloro-3-phenyl-8-(1H-pyrazol-3-yl)imidazo[1,2-b]pyridazin-2-yl]phenyl}cyclobutanamine
1-{4-[3-Phenyl-8-(1H-pyrazol-3-yl)-6-vinylimidazo[1,2-b]pyridazin-2-yl]phenyl}cyclobutanamine
1-{4-[6-Ethyl-3-phenyl-8-(1H-pyrazol-3-yl)imidazo[1,2-b]pyridazin-2-yl]phenyl}cyclobutanamine -continued 2-[4-(1-Aminocyclobutyl)phenyl]-8-ethoxy-N-methyl-3-phenylimidazo[1,2-b]pyridazine-6-carboxamide
1-{4-[6-Chloro-8-(1-methyl-1H-pyrazol-5-yl)-3-phenylimidazo[1,2-b]pyridazin-2-yl]phenyl}cyclobutanamine
1-{4-[6-Chloro-8-(1H-imidazol-2-yl)-3-phenylimidazo[1,2-b]pyridazin-2-yl]phenyl}cyclobutanamine
1-[4-(3-Phenylimidazo[1,2-b]pyridazin-2-yl)phenyl]-cyclobutanamine
2-[4-(1-Aminocyclobutyl)phenyl]-8-methoxy-N-methyl-3-phenylimidazo[1,2-b]pyridazine-6-carboxamide
1-{4-[3-Phenyl-8-(1H-pyrazol-3-yl)imidazo[1,2-b]pyridazin-2-yl]phenyl}cyclobutanamine
2-[4-(1-Aminocyclobutyl)phenyl]-8-(2-methoxyethoxy)-3-phenylimidazo[1,2-b]pyridazine-6-carboxamide
1-{4-[8-(Benzyloxy)-6-chloro-3-phenylimidazo[1,2-b]-pyridazin-2-yl]phenyl}cyclobutanamine
1-[4-(6-Chloro-8-ethoxy-3-phenylimidazo[1,2-b]pyridazin-2-yl)phenyl]cyclobutanamine
Methyl 2-[4-(1-aminocyclobutyl)phenyl]-3-phenylimidazo[1,2-b]pyridazine-8-carboxylate
2-[4-(1-Aminocyclobutyl)phenyl]-3-phenylimidazo[1,2-b]-pyridazin-8-ol
1-{4-[6-(4-Fluorophenyl)-3-phenylimidazo[1,2-b]pyridazin-2-yl]phenyl}cyclobutanamine
2-[4-(1-Aminocyclobutyl)phenyl]-3-phenylimidazo[1,2-b]-pyridazine-6,8-dicarboxamide
2-[4-(1-Aminocyclobutyl)phenyl]-3-phenylimidazo[1,2-b]-pyridazin-6-amine
1-{4-[6-(Methylsulfanyl)-3-phenylimidazo[1,2-b]pyridazin-2-yl]phenyl}cyclobutanamine
N-{2-[4-(1-Aminocyclobutyl)phenyl]-3-phenylimidazo[1,2-b]-pyridazin-6-yl}acetamide
N-{2-[4-(1-1-{4-[6-(Methylsulfonyl)-3-phenylimidazo[1,2-b]-pyridazin-2-yl]phenyl}cyclobutanamine
Methyl 2-[4-(1-aminocyclobutyl)phenyl]-3-phenylimidazo[1,2-b]pyridazine-6-carboxylate
N-{2-[4-(1-Aminocyclobutyl)phenyl]-3-phenylimidazo[1,2-b]-pyridazin-6-yl}-2,2,2-trifluoroacetamide
1-[4-(6-Bromo-3-phenylimidazo[1,2-b]pyridazin-2-yl)phenyl]-cyclobutanamine
1-{4-[6,8-Bis(4-fluorophenyl)-3-phenylimidazo[1,2-b]-pyridazin-2-yl]phenyl}cyclobutanamine
1-{2-[4-(1-Aminocyclobutyl)phenyl]-3-phenylimidazo[1,2-b]-pyridazin-6-yl}ethanone
1-{4-[8-(4-Fluorophenyl)-3-phenylimidazo[1,2-b]pyridazin-2-yl]phenyl}cyclobutanamine
N-{2-[4-(1-Aminocyclobutyl)phenyl]-3-phenylimidazo[1,2-b]-pyridazin-6-yl}methanesulfonamide
1-[4-(6-Chloro-8-cyclopropyl-3-phenylimidazo[1,2-b]-pyridazin-2-yl)phenyl]cyclobutanamine
1-[4-(3-Phenyl-8-propylimidazo[1,2-b]pyridazin-2-yl)phenyl]-cyclobutanamine
2-[4-(1-Aminocyclobutyl)phenyl]-3-phenylimidazo[1,2-b]-pyridazin-8-amine
N-{2-[4-(1-Aminocyclobutyl)phenyl]-3-phenylimidazo[1,2-b]-pyridazin-8-yl}acetamide
1-[4-(6-Chloro-7,8-dimethyl-3-phenylimidazo[1,2-b]pyridazin-2-yl)phenyl]cyclobutanamine
Methyl 2-[4-(1-aminocyclobutyl)phenyl]-7,8-dimethyl-3-phenylimidazo[1,2-b]pyridazine-6-carboxylate
2-[4-(1-Aminocyclobutyl)phenyl]-7,8-dimethyl-3-phenylimidazo[1,2-b]pyridazine-6-carboxamide
1-[4-(6-Methoxy-7,8-dimethyl-3-phenylimidazo[1,2-b]-pyridazin-2-yl)phenyl]cyclobutanamine
1-{4-[7,8-Dimethyl-6-(methylsulfanyl)-3-phenylimidazo[1,2-b]-pyridazin-2-yl]phenyl}cyclobutanamine
1-[4-(6-Ethoxy-7,8-dimethyl-3-phenylimidazo[1,2-b]pyridazin-2-yl)phenyl]cyclobutanamine
Methyl 2-[4-(1-aminocyclobutyl)phenyl]-3-phenyl-8-(1H-pyrazol-3-yl)imidazo[1,2-b]pyridazine-6-carboxylate
Methyl 2-[4-(1-aminocyclobutyl)phenyl]-8-ethoxy-3-phenylimidazo[1,2-b]pyridazine-6-carboxylate
Methyl 2-[4-(1-aminocyclobutyl)phenyl]-8-(1H-imidazol-2-yl)-3-phenylimidazo[1,2-b]pyridazine-6-carboxylate
tert-Butyl {1-[4-(8-acetamido-3-phenylimidazo[1,2-b]-pyridazin-2-yl)phenyl]cyclobutyl}carbamate
2-[4-(1-Aminocyclobutyl)phenyl]-3-phenyl-8-(1H-pyrazol-3-yl)imidazo[1,2-b]pyridazine-6-carboxamide
2-[4-(1-Aminocyclobutyl)phenyl]-8-ethoxy-3-phenyl-imidazo[1,2-b]pyridazine-6-carboxamide
2-[4-(1-Aminocyclobutyl)phenyl]-8-(1H-imidazol-2-yl)-N-methyl-3-phenylimidazo[1,2-b]pyridazine-6-carboxamide
2-[4-(1-Aminocyclobutyl)phenyl]-N-methyl-3-phenylimidazo[1,2-b]pyridazine-8-carboxamide
2-[4-(1-Aminocyclobutyl)phenyl]-8-(cyclopropylmethoxy)-N-methyl-3-phenylimidazo[1,2-b]pyridazine-6-carboxamide
2-[4-(1-Aminocyclobutyl)phenyl]-N-methyl-3-phenyl-8-(1H-pyrazol-3-yl)imidazo[1,2-b]pyridazine-6-carboxamide
2-[4-(1-Aminocyclobutyl)phenyl]-N-ethyl-3-phenyl-imidazo[1,2-b]pyridazine-6-carboxamide
2-[4-(1-Aminocyclobutyl)phenyl]-3-phenyl-8-(1H-pyrazol-3-yl)imidazo[1,2-b]pyridazine-6-carboxylic acid
2-[4-(1-Aminocyclobutyl)phenyl]-N-methyl-3-phenyl-imidazo[1,2-b]pyridazine-6-carboxamide
2-[4-(1-Aminocyclobutyl)phenyl]-N,N-dimethyl-3-phenyl-imidazo[1,2-b]pyridazine-6-carboxamide
2-[4-(1-Aminocyclobutyl)phenyl]-N-(2-hydroxyethyl)-3-phenyl-imidazo[1,2-b]pyridazine-6-carboxamide
2-[4-(1-Aminocyclobutyl)phenyl]-N-(2-hydroxyethyl)-3-phenyl-8-(1H-pyrazol-3-yl)imidazo[1,2-b]pyridazine-6-carboxamide
Methyl 3-{2-[4-(1-aminocyclobutyl)phenyl]-3-phenyl-imidazo[1,2-b]pyridazin-8-yl}propanoate
1-{4-[6-Methoxy-3-phenyl-8-(1H-pyrazol-3-yl)imidazo[1,2-b]-pyridazin-2-yl]phenyl}cyclobutanamine
1-{4-[6-Methoxy-8-(1-methyl-1H-pyrazol-5-yl)-3-phenyl-imidazo[1,2-b]pyridazin-2-yl]phenyl}cyclobutanamine
1-{4-[6-Methoxy-3-phenyl-8-(pyridin-4-yl)imidazo[1,2-b]-pyridazin-2-yl]phenyl}cyclobutanamine
1-[4-(6,8-Diethoxy-3-phenylimidazo[1,2-b]pyridazin-2-yl)-phenyl]cyclobutanamine
1-[4-(8-Butoxy-6-ethoxy-3-phenylimidazo[1,2-b]pyridazin-2-yl)phenyl]cyclobutanamine
1-[4-(6-Ethoxy-3-phenylimidazo[1,2-b]pyridazin-2-yl)-phenyl]cyclobutanamine
2-[4-(1-Aminocyclobutyl)phenyl]-3-phenylimidazo[1,2-b]-pyridazin-6-ol
Methyl ({2-[4-(1-aminocyclobutyl)phenyl]-3-phenylimidazo-[1,2-b]pyridazin-6-yl}oxy)acetate One aspect of the present invention are the compounds disclosed in the examples as well as the intermediates, especially a compound of general formula (II) shown below in scheme 1, as used for their synthesis.

Another aspect of the invention are compounds of formula (I) according to claim 1, wherein
R1 is hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl, aryl, heteroaryl,
wherein said group being optionally substituted, one or more times, identically or differently, with a substituent selected from:
halogen, 1-3C-alkyl, 1-3C-alkoxy, —C(O)OR10, 3-6-cycloalkyl, 3-6C-heterocyclyl, aryl.

Another aspect of the invention are compounds of formula (I) according to claim 1, wherein
R1 is hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl, heteroaryl,
wherein said group being optionally substituted, one or more times, identically or differently, with a substituent selected from:
halogen, 1-3C-alkyl, 1-3C-alkoxy, —C(O)OR10, 3-6-cycloalkyl, aryl.

Another aspect of the invention are compounds of formula (I) according to claim 1, wherein
R1 is hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl, aryl,
wherein said group being optionally substituted, one or more times, identically or differently, with a substituent selected from:

halogen, 1-3C-alkyl, 1-3C-alkoxy, —C(O)OR10, 3-6-cycloalkyl, 3-6C-heterocyclyl, aryl.

Another aspect of the invention are compounds of formula (I) according to claim 1, wherein
R1 is hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl,
wherein said group being optionally substituted, one or more times, identically or differently, with a substituent selected from:
halogen, 1-3C-alkyl, 1-3C-alkoxy, —C(O)OR10, 3-6-cycloalkyl, 3-6C-heterocyclyl, aryl.

Another aspect of the invention are compounds of formula (I) according to claim 1, wherein
R1 is hydrogen, —C(O)NH(1-3C-alkyl), —C(O)NH2 or a group selected from 1-6C-alkoxy, heteroaryl which are optionally substituted with 1-3C-alkyl, 1-3C-alkoxy.

Another aspect of the invention are compounds of formula (I) according to claim 1, wherein
R1 is 1-6C-alkoxy, preferably 1-4-alkyoxy, especially methoxy.

Another aspect of the invention are compounds of formula (I) according to claim 1, wherein
R2 is hydrogen.

Another aspect of the invention are compounds of formula (I) according to claim 1, wherein
R3 is hydrogen, hydroxy, NR5R6, halogen, cyano, CO(NR8R9), C(O)OR8, C(O)(1-6C-alkyl), NHS(O)$_2$R11, NHC(O)NHR11, —S(O)$_n$-1-6C-alkyl, —S(O)$_2$NR5R6 or a group selected from 1-6C-alkyl, 1-6C-alkoxy 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, NHC(O)(1-6C-alkyl), 2-6C-alkenyl, 2-6C-alkynyl,
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)$_2$R11, 3-7C-heterocyclyl, aryl.

Another aspect of the invention are compounds of formula (I) according to claim 1, wherein
R3 is hydrogen, hydroxy, NR5R6, halogen, cyano, CO(NR8R9), C(O)OR8, C(O)(1-3C-alkyl), NHS(O)$_2$R11, NHC(O)NHR11, —S(O)$_n$-1-3C-alkyl, —S(O)$_2$NR5R6 or a group selected from 1-3C-alkyl, 1-3C-alkoxy 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, NHC(O)(1-3C-alkyl), 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl.

Another aspect of the invention are compounds of formula (I) according to claim 1, wherein
R3 is hydrogen, hydroxy, amino, bromine, methoxy, ethoxy, butoxy, pyridine-3-yl, pyridine-4-yl, pyrazol-3-yl, 1-methyl-pyrazol-3-yl, imidazole-2-yl, methyl, propyl, —O—(CH$_2$)—O—CH$_3$, —O—CH$_2$-phenyl, —O—CH$_2$-cyclopropyl, —C(O)OCH$_3$, —C(O)—NHCH$_3$, —C(O)—NH$_2$, 4-fluoro-phenyl, —(CH$_2$)$_2$—C(O)OCH$_3$, cyclopropyl, —NH—C(O)CH$_3$, Another aspect of the invention are compounds of formula (I) according to claim 1, wherein
R3 is 1-4C-alkyl, COOR8, (CO)NH2, 1-4C-alkoxy, halogen, especially methyl, ethyl, trifluoromethyl, aminocarbonyl, methoxy, methoxycarbonyl, ethoxycarbonyl, COOH, bromine.

Another aspect of the invention are compounds of formula (I) according to claim 1, wherein
R3 is NR8R9, —C(O)OR10, —C(O)NR8R9.

In another embodiment of the above-mentioned aspects, the invention relates to compounds of formula (I) according to claim 1, wherein R4 is an unsubstituted phenyl moiety.

Another aspect of the invention are compounds of formula (I) according to claim 1, wherein
R8 is hydrogen, 1-4Calkyl, especially hydrogen or 1-2C-alkyl.

Another aspect of the invention are compounds of formula (I) according to claim 1, wherein n is 0 or 2.

Another aspect of the invention are compounds of formula (I) according to claim 1, wherein R1 is selected from the following groups:
hydrogen, hydroxy, NR5R6, CO(NR8R9), C(O)OR8, NHC(O)(1-6C-alkyl), or a group selected from 1-3C-alkyl, 1-3C-alkoxy, 3-6C-cycloalkyl, aryl, heteroaryl,
wherein said group being optionally substituted, one or more times, identically or differently, with a substituent selected from:
halogen, 1-3C-alkyl, 1-3C-alkoxy, —C(O)OR10, 3-6-cycloalkyl, 3-6C-heterocyclyl, aryl
and
R3 is selected from
hydrogen, hydroxy, NR5R6, halogen, cyano, CO(NR8R9), C(O)OR8, C(O)(1-3C-alkyl), NHS(O)$_2$R11, NHC(O)NHR11, —S(O)n-1-3C-alkyl, —S(O)$_2$NR5R6 or a group selected from 1-3C-alkyl, 1-3C-alkoxy 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, NHC(O)(1-3C-alkyl), 2-3C-alkenyl, 2-3C-alkynyl,
wherein said group being optionally substituted, one or more times, identically or differently, with a substituent selected from:
hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)$_2$R11, 3-6C-heterocyclyl, aryl.

Another aspect of the invention are compounds of formula (I) according to claim 1, wherein R1 is selected from the following groups:
is hydrogen, —C(O)NH(1-3C-alkyl), —C(O)NH2 or a group selected from 1-6C-alkoxy, heteroaryl which are optionally substituted with 1-3C-alkyl, 1-3C-alkoxy and R3 is —C(O)NR8R9.

Another aspect of the invention are compounds of formula (I) according to claim 1, wherein R1 is selected from the following groups:
is hydrogen, —C(O)NH(1-3C-alkyl), —C(O)NH2 or a group selected from 1-6C-alkoxy, heteroaryl which are optionally substituted with 1-3C-alkyl, 1-3C-alkoxy and R3 is NR8R9.

Another aspect of the invention are compounds of formula (I) according to claim 1, wherein R1 is selected from the following groups:

is hydrogen, —C(O)NH(1-3C-alkyl), —C(O)NH2 or a group selected from 1-6C-alkoxy, heteroaryl which are optionally substituted with 1-3C-alkyl, 1-3C-alkoxy and R3 is —C(O)OR10.

Another aspect of the invention are compounds of formula (I) according to claim 1, wherein R1 is selected from the following groups:
is hydrogen, —C(O)NH(1-3C-alkyl), —C(O)NH2 or a group selected from 1-6C-alkoxy, heteroaryl which are optionally substituted with 1-3C-alkyl, 1-3C-alkoxy and R3 is 1-4C-alkyl, COOR8, (CO)NH2, 1-4C-alkoxy, halogen, especially methyl, ethyl, trifluoromethyl, aminocarbonyl, methoxy, methoxycarbonyl, ethoxycarbonyl, COOH, bromine

DEFINITIONS

"1-6C-alkyl" is a straight-chain or branched alkyl group having 1 to 6 carbon atoms. Examples are methyl, ethyl, n propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Whenever "alkyl" is part of a constituent consisting of "alkyl" together with another component the definition of "alkyl" given above also applies.

The term "1-6C-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("2-3C-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "2-6C-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("2-3C-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

NR5R6 represents "amino" as well as "mono- or di-1-6C-alkylamino" radicals containing in addition to the nitrogen atom, independently one or two of the above mentioned 1-6C-alkyl radicals. Examples are the methyamino, the ethylamino, the isopropylamino, the dimethylamino, the diethylamino, the methyl(ethyl)amino and the diisopropylamino radical The same is intended for any NRxRy residue mentioned within the claims or description.

"Aryl" represents a mono-, or bicyclic aromatic carbocyclic radical having, as a rule, 6 to 10 carbon atoms; by way of example phenyl or naphthyl. Phenyl is preferred.

The term "-(1-6C-alkyl)-aryl" represents an aryl radical as defined above which is connected to the rest of the molecule via a straight or branched alkyl chain, preferably —(CH$_2$)-aryl, or —(CH$_2$CH$_2$)-aryl. Benzyl is particularly preferred.

The term "aryloxy" or "—O-aryl" represents the same aryl moieties as defined for the term aryl whereby the ring is connected via an oxygen atom to the rest of the molecule.

The term "—O-(1-6C-alkyl)-aryl" represents the same aryl moieties as defined for the term aryl whereby the ring is connected via a —O-(1-6Calkyl) spacer to the rest of the molecule. Preferred —O-(1-6Calkyl) spacers in this context are —O—(CH$_2$)—, or —O—(CH$_2$CH$_2$)—. Benzyloxy is particularly preferred.

"Halogen" within the meaning of the present invention is iodine, bromine, chlorine or fluorine, preferably "halogen" within the meaning of the present invention is chlorine or fluorine, if halogen were used as a leaving group during synthesis bromine or iodine are preferred.

"1-4C-Haloalkyl", which also can be defined as an alkyl moiety which is substituted one or more times with halogen, is a straight-chain or branched alkyl group having 1 to 4 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and penta-fluoroethyl, whereby fluoromethyl, difluoromethyl, trifluoromethyl, fluoroethyl, 1,1-difluoroethyl, or 1,1,1-trifluoroethyl are preferred. Partially or completely fluorinated C1-C4-alkyl groups are considered to be encompassed by the term 1-4C-haloalkyl.

"1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, isobutoxy, sec-butoxy, tert-butoxy, pro-poxy, isopropoxy, ethoxy and methoxy radicals, preferred are methoxy, ethoxy, propoxy, isopropoxy.

"3-7C-Cycloalkyl" stands for cyclopropyl, cyclobutyl, cyclopentyl, cyclohexyl or cycloheptyl, preferably cyclopropyl.

"3-7C-Cycloalkyloxy" or "—O-(3-7C-cycloalkyl)" stands for cyclopropyloxy, cyclobutyloxy, cyclopentyloxy, cyclohexyloxy or cycloheptyloxy, preferably cyclopropyloxy.

The term "heteroaryl" represents a monocyclic 5- or 6-membered aromatic heterocycle comprising without being restricted thereto, the 5-membered heteroaryl radicals furyl, thienyl, pyrrolyl, oxa-zolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl, preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The term "-(1-6C-alkyl)-heteroaryl" represents a heteroaryl radical as defined above which is connected to the rest of the molecule via a straight or branched alkyl chain, preferably —(CH$_2$)-heteroaryl, or —(CH$_2$CH$_2$)-heteroaryl, whereby —(CH$_2$)-heteroaryl is particularly preferred.

The term "Heteroaryloxy" or "—O-heteroaryl" represents the same heteroaryl moieties as defined for the term heteroaryl whereby the ring is connected via an oxygen atom to the rest of the molecule.

The term "—O-(1-6C-alkyl)-heteroaryl" represents the same heteraryl moieties as defined for the term heteroaryl whereby the ring is connected via a —O-(1-6Calkyl) spacer to the rest of the molecule.

The term "—O-(1-6C-alkyl) spacer" can vary in the sense of the invention to have an alkylene chain having from 1-6, 1-5, 1-4, 1-3, 1-2 or 1 carbon atoms which can be straight or branched where possible.

"3-7C-Heterocyclyl", or "heterocyclyl" represents a mono- or polycyclic, preferably mono- or bicyclic, more preferably monocyclic, nonaromatic heterocyclic radical containing, 4 to 10, preferably 4 to 7, ring atoms, and up to 3, preferably up to 2, hetero atoms and/or hetero groups from the series consisting of N, O, S, SO, SO$_2$. The heterocyclyl radicals can be saturated or partially unsaturated and, unless stated otherwise, may be optionally substituted, one or more times, identically or differently, with a substituent selected from: 1-4C-alkyl, 1-4C-haloalkyl, 1-4C-alkoxy, hydroxy, fluorine, whereby the 1-4C-alkyl may be optionally further substituted with hydroxy. Particularly preferred heterocyclic radicals are 4- to 7-membered monocyclic saturated heterocyclyl radicals having up to two hetero atoms from the series consisting of O, N and S. The following may be mentioned by way of example and by preference: oxetanyl, tetrahydrofuranyl, azetidinyl, 3-hydroxyazetidinyl, 3-fluoroazetidinyl, 3,3-difluoroazetidinyl, pyrrolidinyl, 3-hydroxypyrrolidinyl, pyrrolinyl, piperidinyl, 3-hydroxypiperidinyl, 4-hydroxypiperidinyl, 3-fluoropiperidinyl, 3,3-difluoropiperidinyl, 4-fluoropiperidinyl, 4,4-difluoropiperidinyl, piperazinyl, N-methyl-piperazinyl, N-(2-hydroxyethyl)-piperazinyl, morpholinyl, thiomorpholinyl, azepanyl, homopiperazinyl, N-methyl-homopiperazinyl.

The term "heterocyclyloxy" or —O-heterocyclyl" represents the same heterocyclic moieties as defined for the term heterocyclyl whereby a C atom in the ring is connected via an oxygen atom to the rest of the molecule. Preferred heterocyclic moieties are either unsubstituted, or may be optionally substituted on a ring nitrogen arom with a substituent selected from: 1-4C-alkyl, 1-4C-haloalkyl, 1-4C-alkoxy.

The term "—O-(1-6C-alkyl)-heterocyclyl" represents the same heterocyclyl moieties as defined for the term heterocyclyl whereby the ring is connected via a —O-(1-6Calkyl) spacer to the rest of the molecule. In one aspect of the invention heterocyclic moieties containing one or more ring nitrogen atom are preferably connected to the —O-(1-6-alkyl) spacer via one of the ring nitrogen atoms.

The term -(1-6C-alkyl)-heterocyclyl represents the same heterocyclyl moieties as defined for the term heterocyclyl s.o. whereby the ring is connected via a -(1-6C-alkyl) spacer to the rest of the molecule.

The NH(CO)1-6C-alkyl or the NH(CO)R11 group includes for example NH(CO)CH3, NH(CO)C2H5, NH(CO)C3H7, NH(CO)CH(CH3)2.

The NHS(O)$_2$R11 group includes for example NHS(O) 2CH3, NHS(O)2C2H5, NHS(O)2C3H7, NHS(O)2CH (CH3)2.

The NH(CO)NHR11 group includes for example NHC (O)NHCH3, NHC(O)NHC2H5.

The C(O)NR8R9 group includes, for example, C(O)NH2, C(O)N(H)CH3, C(O)N(CH3)2, C(O)N(H)CH2CH3, C(O)N (CH3)CH2CH3 or C(O)N(CH2CH3)2. In the case of —NR8R9, when R8 and R9 together with the nitrogen atom to which they are attached form a 3-6C-heterocyclic ring, the term "3-6C-heterocyclic ring" is defined above.

The C(O)OR8 group includes for example C(O)OH, C(O)OCH3, C(O)OC2H5, C(O)OC3H7, C(O)CH(CH3)2, C(O)OC4H9, C(O)OC5H11, C(O)OC6H13; for C(O)O(1-6Calkyl) the alkyl part may be straight or branched.

Constituents which are optionally substituted as stated herein, may be substituted, unless otherwise noted, one or more times, independently from one another at any possible position. When any variable occurs more than one time in any constituent, each definition is independent.

In case of R1, R2 or R3 it is understood that the groups selected from 1-6C-alkyl, 1-6C-alkoxy, 3-7C-cycloalkyl, aryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl may be optionally substituted, one or more times, identically or differently, with a substituent selected from: hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11. Preferably the groups -(1-6C-alkyl)-aryl, -(1-6C-alkyl)-heteroaryl, —O-(1-6C-alkyl)-heteroaryl, —O-(1-6C-alkyl)-(3-7C-heterocyclyl), —O-(1-6C-alkyl)-aryl.

The heteroarylic, or heterocyclic groups mentioned herein may be substituted by their given substituents or parent molecular groups, unless otherwise noted, at any possible position, such as e.g. at any substitutable ring carbon or ring nitrogen atom. Analogously it is being understood that it is possible for any heteroaryl or heterocyclyl group to be attached to the rest of the molecule via any suitable atom if chemically suitable. Unless otherwise noted, any heteroatom of a heteroarylic ring with unsatisfied valences mentioned herein is assumed to have the hydrogen atom(s) to satisfy the valences. Unless otherwise noted, rings containing quaternizable amino- or imino-type ring nitrogen atoms (—N=) may be preferably not quaternized on these amino- or imino-type ring nitrogen atoms by the mentioned substituents or parent molecular groups.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from $NH_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or Sagopilone; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and (vii) folic acid antagonists such as methotrexate (Farmitrexat®) or premetrexed (Alimta®).

The term "target specific anti-cancer agent", includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI 24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors (e.g. Femara, Arimedex or Aromasin).

Other "target specific anti-cancer agents" include bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples of anti-cancer agents include, but are not limited 131 I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

A special aspect of the invention are combinations comprising at least one compound according to claim 1 and at least one of the anti-cancer drugs selected from Ancestim, atrigel-leuprolide, axitinib, Bacillus Calmette-Guerin (BCG)-Tice, bosutinib, brentuximab vedotin, brivanib alaninate, Cervarix, cinacalcet hydrochloride, crizotinib, cytarabine ocfosfate, diethylstilbestrol, doxorubicin eluting beads, enzastaurin hydrochloride, etoposide phosphate disodium salt, floxuridine, fludeoxyglucose (18F), Gardasil, histrelin acetate, icotinib hydrochloride, ingenol mebutate, interferon alfa-2A, interferon alfa-2b, interferon alfa-n1, interferon alfa, interferon gamma-n1, ketoconazole, leucovorin/UFT, leuprolide acetate depot, levothyroxine sodium, liposomal cytarabine, liposomal daunorubicin, liposomal doxorubicin, M-Vax, MDV-3100, midostaurin, minocycline hydrochloride, motesanib diphosphate, muromonab-CD3, oblimersen sodium, octreotide acetate, omacetaxine mepesuccinate, ombrabulin hydrochloride, paclitaxel nanoparticles, paclitaxel poliglumex, PEG-liposomal doxorubicin hydrochloride, pilocarpine hydrochloride, pixantrone maleate, rapamycin, ridaforolimus, ruboxistaurin mesilate hydrate, ruxolitinib phosphate, thyrotropin alfa, trimetrexate glucuronate, VAL-083, vesnarinone, vincristine TCS, Virulizin, zotarolimus, AZD-8055, BEZ-235, BGT-226, BKM-120, CAL-101, CC-223, GDC-0980, GSK-2110183, GSK-2636771, OSI-027, perifosine, PF-04691502, pictrelisib, PX-866, triciribine phosphate, UCN-01, XL-147, XL-765, ARRY-162, AS-703026, E-6201, selumetinib, trametinib dimethyl sulfoxide.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

further aspect of the present invention. Preferred intermediates are the Intermediate Examples as disclosed below.

The Compounds According to the Invention can be Prepared as Follows.

The compounds according to the invention can be prepared according to the following scheme, Scheme 1:

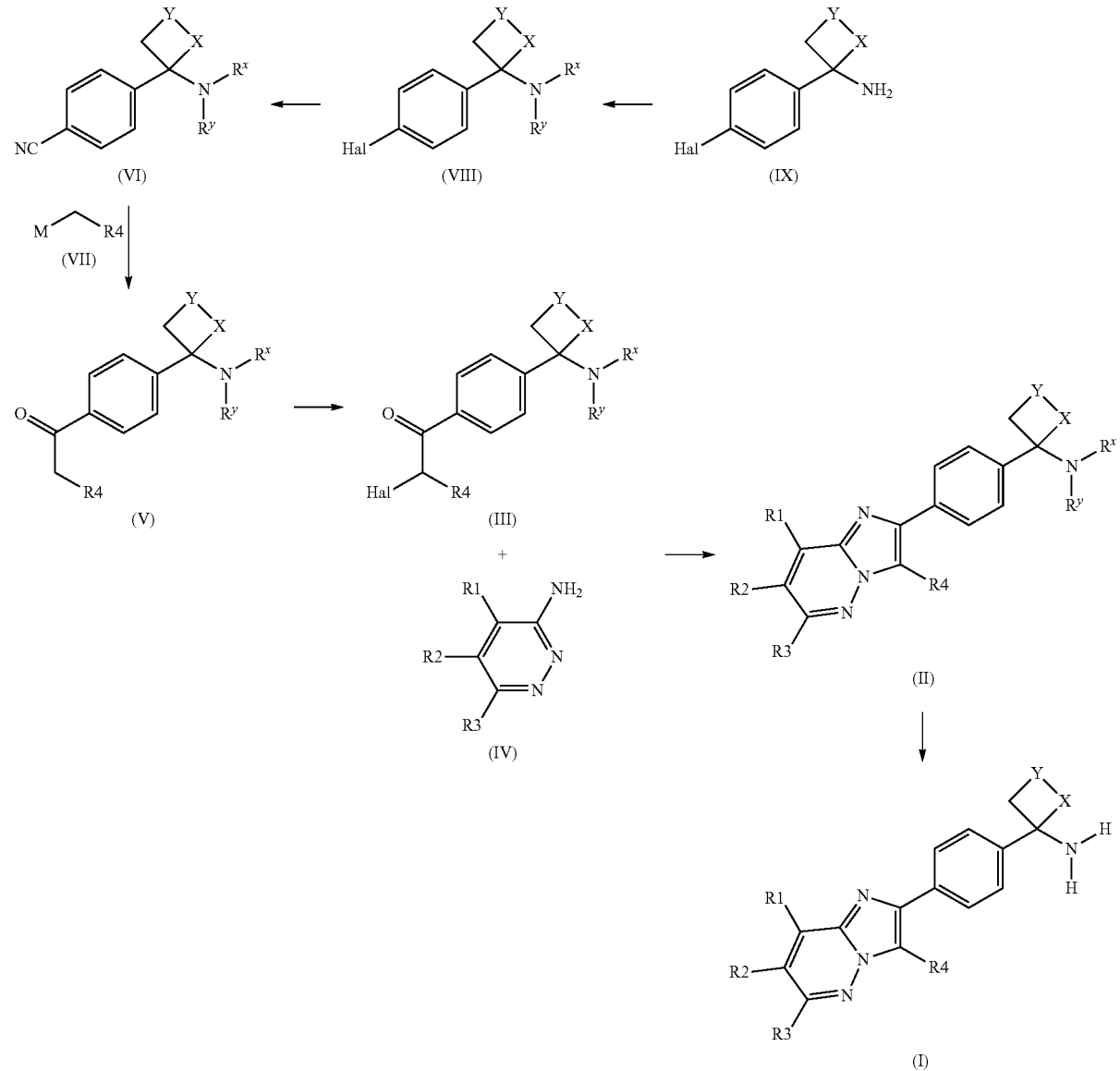

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below, as well as their use for the synthesis of the compounds of claims 1-5, are one wherein X, Y, R1, R2, R3 and R4 have the meanings defined above, whereby Rx Ry is R6, or a protecting group; Hal is halogen, preferably M is Mg-Hal, Zn-Hal, or Li.

Compounds of general formula (I) may be prepared from compounds of general formula (II). Rx may optionally be R6, or a protecting group, or other such precursor which requires further manipulation.

The use of amine protecting groups in organic synthesis is well known to persons practiced in the art. Amine protecting groups include, but are not limited to:

carbamate protecting groups, including, but not limited to methyl carbamate, ethyl carbamate, 9-fluorenylmethyl carbamate, (Fmoc), tert-butyl carbamate (BOC), allyl carbamate, and benzyl carbamate (CBZ) including benzyl carbamates substituted on the phenyl ring, amide protecting groups, including, but not limited to N-formyl amide, and N-acetyl amide, N-benzyl amine protecting groups, including N-benzyl amines substituted on the phenyl ring.

When Rx and Ry of the compound of formula (I) are both hydrogen, Rx of the compound of formula (II) may be a protecting group and Ry of the compound of formula (II) may be hydrogen, the same protecting group as Rx, or a different protecting group, or Rx and Ry may combine to make a cyclic imide protecting group, such as an N-phthaloyl protecting group.

An amine protecting group may be reacted with a suitable reagent to remove the protecting group and replace it with a hydrogen. Such suitable reagents include, but are not limited to:

acid reagents, include, but are not limited to hydrochloric acid, acetic acid, trifluoroacetic acid, methanesulfonic acid, trifluoromethanesulfonic acid, sulfuric acid, boron tribromide; acid reagents may be used for the removal of tert-butyl carbamate, N-formyl amide, or N-acetyl amide or protecting groups.

base reagents, include, but are not limited to lithium hydroxide, potassium hydroxide, sodium hydroxide, caesium carbonate, ammonium hydroxide; base reagents may be used for the removal of methyl carbamate, 9.fluorenyl carbamate, ethyl carbamate, N-formyl amide, or N-acetyl amide protecting groups.

nucleophilic reagents, include, but are not limited to lithium iodide, sodium iodide, potassium iodide, trimethylsilyl iodide, hydrazine, nucleophilic reagents may be used for the removal of benzyl carbamate, N-formyl amide, N-acetyl amide, or N-phthaloyl protecting groups.

metal-mediated reagents, including, but are not limited to nickel reagents, palladium reagents, platinum reagents may be used for the removal of allyl carbamate protecting groups.

reduction reagents, include, but are not limited to sodium in ammonia, or the combination of a hydrogen source, such as, but not limited to hydrogen gas, formic acid, or a salt of formic acid and a metal reagent, including, but not limited to a nickel reagent, palladium reagent, platinum reagent; reduction reagents may be used for the removal of 9-fluorenylmethyl carbamate, benzyl carbamate, or N-benzyl amine protecting groups.

For example, Rx in compounds of general formula (II) may be a protecting group such as the Boc group, —CO(OtBu). Preparation of compounds of general formula (I) may thus be accomplished by use of an appropriate deprotection reaction, such as in the case of a Boc group, acidic reaction conditions, for example, with a solution of 4M hydrochloric acid in dioxane or trifluoromethanesulfonic acid, in an appropriate solvent, such as for example DCM and methanol, at ambient temperature. Further conditions to deprotect the Boc group, or further protecting groups that may be suitable for use in blocking the amino functionality in compounds of general formula (II), including their synthesis and deprotection, are found, for example, in T. W. Greene, Protective Groups in Organic Synthesis, John Wiley & Sons, 1999, 3rd Ed., or in P. Kocienski, Protecting Groups, Thieme Medical Publishers, 2000. Similarly, when Ry is not H, then Ry is a protecting group, such as for example when Rx and Ry together form a cyclic protecting group such as for example a phthalamide.

Furthermore, compounds of general formula (II) may contain functionality that may itself be further modified, thus allowing introduction of the desired functionality in the R1, R2 or R3 groups. Such transformations include oxidations, reductions, nucleophilic substitutions, electrophilic substitutions, radical reactions, or metal promoted reactions such as metal assisted cross-coupling reactions, such as for example Suzuki, Stille, or Heck reactions, or the like. Similarly, compounds of general formula (I) may also be modified in this way to provide further compounds according to the invention, providing the transformations do not cause unwanted side reactions at the —NHR6 group.

Thus a further aspect of the invention is a process for the manufacture of compounds of general formula (I) according to claim 1 by reacting a compound of general formula (II)

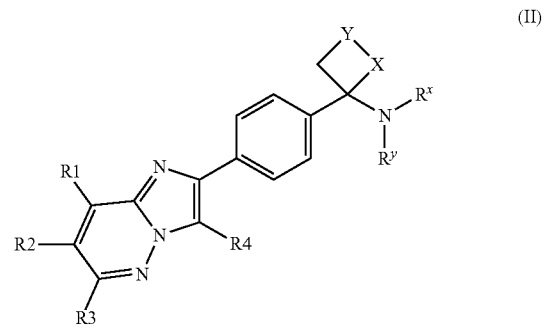

(II)

wherein
R1-R4 have the meaning as stated in claim 1 and
Rx,Ry are R6, or a protecting group,
wherein transformation to a compound of general formula (I) is accomplished by use of an appropriate deprotection reaction, whereby the protecting groups as discussed above can be used.

Another aspect of the invention is a process as disclosed above whereby subsequently of before the deprotection step, further modifications allowing introduction of the desired functionality in the R1, R2 or R3 groups can be performed.

Compounds of general formula (II) may be prepared from an intermediate ketone of general formula (III) and a heterocyclic amine of general formula (IV), by use of an appropriate cyclisation reaction. For example, compounds of general formula (II) may be prepared by reacting (III) and (IV) in an appropriate solvent, such as for example DMF or ethanol, at elevated temperatures from 50° C. to 150° C. The use of basic additives such as a tertiary amine, for example triethylamine, may be beneficial.

Compounds of general formula (IV) are either commercially available, may be prepared using the methods described in the examples, may be prepared using known methods, or may be prepared by analogous methods to those known by the person skilled in the art.

Compounds of general formula (III) may be prepared from a ketone of general formula (V) by use of an appropriate halogenation reaction. For example in the case of halogen is Br, a suitable bromination reaction, such as for example by reacting a ketone of general formula (V) with pyridinium hydrobromide perbromide in a suitable solvent, such as THF, at suitable temperatures, such as for example from 0° C. to ambient temperature.

Compounds of general formula (V) may be prepared from a compound of general formula (VI) using known methods, such as by addition of a suitable organometallic reagent (VII), in a suitable solvent, such as ethereal solvents, for example THF, at low temperatures, for example from −78° C. to −10° C., preferably from −30° C. to −10° C. Preferred organometallic reagents are for example organomagnesium reagents in which M is —MgCl or —MgBr, more preferably —MgCl.

Compounds of general formula (VI) may be prepared from compounds of general formula (VIII) using known methods, such as by way of a palladium catalysed cyanation reaction, using a suitable catalyst such as tetrakis(triphenylphosphine)palladium(0)[Pd(PPh$_3$)$_4$], a suitable cyano source, such as zinc dicyanide, a suitable solvent, such as DMF, whereby dry DMF may be beneficial, and elevated temperatures, such as up to the boiling point of the solvent, preferably at 80° C.

Compounds of general formula (VIII) and (IX) are either commercially available, may be prepared using the methods described below, may be prepared using known methods, or may be prepared by analogous methods to those known by the person skilled in the art.

One aspect of the invention are compounds of formula (II), especially wherein Rx is the Boc group, —CO(OtBu) and Ry is hydrogen.

Another aspect of the invention is the process for the manufacture of compounds of general formula (I), characterized in that a compound of formula (II)

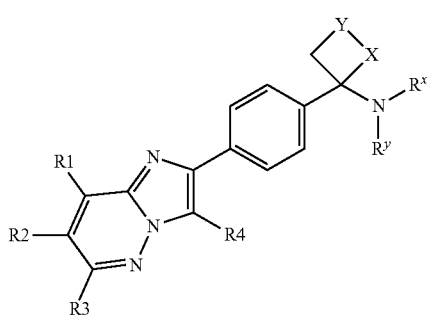

whereby R1-R4, X and Y have the meaning according to claim 1 and Rx is R6 or a protecting group; Ry is hydrogen or a protecting group, or Rx and Ry together, or Y and Rx together, may form a cyclic protecting group, Hal is halogen, is reacted with a solution of 4M hydrochloric acid in dioxane or trifluoromethanesulfonic acid, in an appropriate solvent, such as for example DCM and methanol, at ambient temperature forming a compound of formula (I)

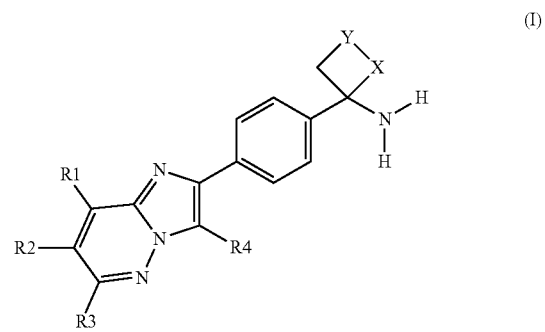

Thus another aspect of the invention is the use of intermediate of formula (II) for the preparation of compounds of formula (I).

One preferred aspect of the invention is the process for the preparation of the compounds of claims 1-5 according to the Examples.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as meta-chloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt). An abnormal activation of the PI3K/AKT pathway is an essential step towards the initiation and maintenance of human tumors and thus its inhibition, for example with AKT inhibitors, is understood to be a valid approach for treatment of human tumors. For a recent review see Garcia-Echeverria et al (Oncogene, 2008, 27, 551-5526).

Cellular activity and analogous terms in the present invention is used as known to persons skilled in the art, as an example, inhibition of phosphorylation, inhibition of cellular proliferation, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which excecutes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Furthermore, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of the Pi3K/Akt pathway induces cellular effects as mentioned herein, alone, or in combination with standard cytotoxic or targeted anti-cancer drugs.

Compounds according to the present invention exhibit anti-proliferative and/or pro-apoptotic and/or chemosensitizing properties. Accordingly, the compounds of the present invention are useful for the treatment of hyperproliferative disorders, in particular cancer. Therefore the compounds of the present invention are useful to induce an anti-proliferative and/or pro-apoptotic and/or chemosensitizing effect in mammals, such as humans, suffering from a hyperproliferative disorders, like cancer.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, especially malignant neoplasia, including cancer and the tumor types as disclosed below.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are useful for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

In another aspect of the invention the compounds according to the present invention can be preferably used for the treatment of breast cancer.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

Compounds according to the present invention are suitable for treatment, prevention or amelioration of the diseases of benign and malignant behavior as described above, such as e.g. benign or malignant neoplasia, particularly cancer, especially a cancer that is sensitive to Pi3K/Akt pathway inhibition.

The present invention further includes a method for treating, preventing or ameliorating diseases, preferably treating mammals, including humans, which are suffering from one of the abovementioned conditions, illnesses, disorders or diseases. The method is characterized in that a pharmacologically active and therapeutically effective and tolerable amount of one or more of the compounds according to the present invention is administered to the subject in need of such treatment.

The present invention further includes a method for treating, preventing or ameliorating diseases responsive to inhibition of the Pi3K/Akt pathway, in a mammal, including human, preferably treating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of benign or malignant neoplasia, particularly cancer, comprising administering a pharmacologically active and therapeutically effective and tolerable amount of one or more of the compounds according to the present invention to a subject in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, especially malignant neoplasia, particularly cancer, in a mammal, including human, comprising administering a pharmacologically active and therapeutically effective and tolerable amount of one or more of the compounds according to the present invention to said mammal.

The present invention further includes a method for treating solid and hematological tumors, whereby solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). and hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A preferred aspect of the invention includes a method for treating breast cancer.

The present invention further relates to the use of the compounds for the production of pharmaceutical compositions, which are employed for the treatment, prophylaxis, and/or amelioration of one or more of the illnesses mentioned, preferably for the treatment of one or more of the illnesses mentioned.

The present invention further relates to the use of the compounds for the manufacture of pharmaceutical compositions for treating, preventing or ameliorating, preferably treating hyperproliferative diseases and/or disorders responsive to the induction of apoptosis, such as e.g. benign or malignant neoplasia, especially malignant neoplasia, in particular cancer, especially those cancer diseases and tumor types mentioned above.

The present invention further relates to the use of the compounds according to this invention for the production of pharmaceutical compositions for treating, preventing or ameliorating, preferably treating benign or malignant neoplasia, especially malignant neoplasia, particularly cancer, such as e.g. any of those cancer diseases and tumor types described above.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The invention further related to the use of a compound according to the invention or a pharmaceutically acceptable salt thereof, for the production of a pharmaceutical composition for the treatment, prevention or amelioration of a disease mediated by a dysregulated function of a single protein kinase or multiple protein kinases and/or disorders responsive to the induction of apoptosis.

The invention further relates to a pharmaceutical composition, comprising a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

In the sense of the invention auxiliaries, vehicles, excipients, diluents, carriers or adjuvants all mean additives which may be added to the compound to obtain a pharmaceutically acceptable composition suitable for administration.

Thus the invention relates to a pharmaceutical compositions comprising one or more of the compounds according to this invention and one or more pharmaceutically acceptable additives.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical additives, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the additives, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound additives, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular additives of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1500 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, more specifically benign or malignant hyperplasia, particularly cancer, such as e.g. any of those cancer diseases described above, especially breast cancer.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

The invention further relates to the use of a pharmaceutical composition comprising one or more of the compounds according to this invention as sole active ingredient(s) and a pharmaceutically acceptable additives in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range depending from the agent combined.

In practising the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. beningn or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating, especially treating hyperproliferative diseases and/or disorders responsive to induction of apoptosis, such as e.g. benign or malignant neoplasia, especially malignanr neoplasia, e.g. cancer, particularly any of those cancer diseases and tumor types mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating, especially treating hyperproliferative diseases, and/or disorders responsive to the induction of apoptosis, such as e.g. malignant or benign neoplasia, especially malignant neoplasia, such as e.g. cancer, particularly those diseases and tumor types mentioned herein.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially malignant neoplasia, e.g. cancer, like any of those cancer diseases and tumor types mentioned herein.

In addition, compounds according to the present invention can be used in the pre- or post-surgical treatment of cancer.

In further addition, compounds of the present invention can be used in combination with radiation therapy.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Experimental Part

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using ACD/Name Batch version 12.01 or using AutoNom2000 as implemented in MDL ISIS Draw. In some cases generally accepted names of commercially available reagents were used in place of AutoNom2000 generated names.

| Abbreviation | Meaning |
| --- | --- |
| anh | anhydrous |
| boc | t-Butoxycarbonyl |
| br | broad |
| CI | chemical ionisation |
| d | doublet |
| dd | doublet of doublet |
| DAD | diode array detector |
| DCM | dichloromethane |
| DMF | N,N-dimethylformamide |
| EtOAc | ethyl acetate |
| Eq. | equivalent |
| ESI | electrospray (ES) ionization |
| HPLC | high performance liquid chromatography |
| LC-MS | liquid chromatography mass spectrometry |
| m | multiplet |
| MeOH | methanol |
| MPLC | medium performance liquid chromatography |
| MS | mass spectrometry |
| n-BuLi | n-Butyllithium |
| NMR | nuclear magnetic resonance spectroscopy: chemical shifts (δ) are given in ppm. The chemical shifts were corrected by setting the DMSO signal to 2.50 ppm using unless otherwise stated. |
| PYBOP | (benzotriazol-1-yloxy)tripyrrolidinophosphium hexafluorophosphate |
| q | quartet |
| r.t. or rt | room temperature |
| RT | retention time (as measured either with HPLC or UPLC) in minutes |
| s | singlet |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

Examples

UPLC-MS Standard Procedures

Analytical UPLC-MS was performed using UPLC-MS Method 1 unless otherwise stated. The masses (m/z) are reported from the positive mode electrospray ionisation unless the negative mode is indicated (ES−).

Method 1:
Instrument: Waters Acquity UPLC-MS SQD 3001; column: Acquity UPLC BEH C18 1.7 50×2.1 mm; eluent A: water+0.1% formic acid, eluent B: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD Method 2:
Instrument: Waters Acquity UPLC-MS SQD 3001; column: Acquity UPLC BEH C18 1.7 50×2.1 mm; eluent A: water+0.2% ammonia, Eluent B: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD Method 3:
Instrument: Waters Acquity UPLC-MS SQD 3001; column: Acquity UPLC BEH C18 1.7 50×2.1 mm; eluent A: water+0.1% ammonia, eluent b: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD Method 4:
instrument: Waters Acquity UPLC-MS SQD 3001; column: Acquity UPLC BEH C18 1.7 50×2.1 mm; eluent A: water+0.2% ammonia, eluent B: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD Intermediate Examples Intermediate Example Int-1 tert-Butyl {1-[4-(6-methyl-3-phenylimidazo[1,2-b]pyridazin-2-yl)phenyl]-cyclobutyl}carbamate

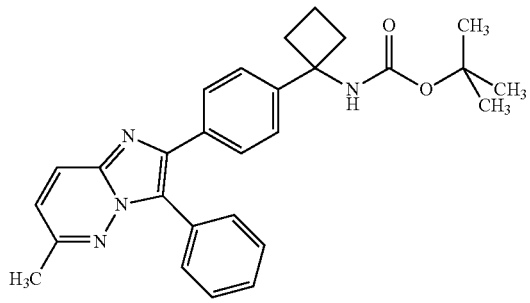 [SMILES: Cc1ccc2nc(-c3ccc(C4(NC(=O)OC(C)(C)C)CCC4)cc3)c(-c3ccccc3)n2n1]

Step 1:
tert-Butyl[1-(4-bromophenyl)cyclobutyl]carbamate

The free base of commercially available 1-(4-bromophenyl)cyclobutanamine hydrochloride [CAS 1193389-40-0] (8.99 g, 34.24 mmol, 1.0 eq) was prepared as follows: (8.99 g, 34.24 mmol, 1.0 eq) of the hydrochloride salt was taken up in DCM and washed sequentially with aqueous sodium bicarbonate and water and the organic portion was tried and concentrated.

The crude amine was taken up in dry THF (120 mL) and diisopropylethylamine (17.62 mL, 102.7 mmol, 3.0 eq) under nitrogen and a solution of di-tert-butyldicarbonate (8.22 g, 37.6 mmol, 1.1 eq) in THF (20 mL) was added. The reaction was stirred at rt overnight. The mixture was partitioned between EtOAc and water and the extracted organic phase was washed with brine and concentrated in vacuo to give the title compound.

Alternatively, the title compound may be prepared by known methods, such as those given in WO2008/70041, in particular from commercially available (4-bromophenyl)acetonitrile.

Step 2:
tert-Butyl[1-(4-cyanophenyl)cyclobutyl]carbamate

The title compound may be prepared from by known methods, such as those given in WO2008/70041, in particular from tert-butyl[1-(4-bromophenyl)cyclobutyl]carbamate.

Alternatively, tert-butyl[1-(4-cyanophenyl)cyclobutyl]carbamate (CAS 1032349-97-5) may be obtained commercially.

Step 3: tert-Butyl {1-[4-(phenylacetyl)phenyl]cyclobutyl}carbamate

The title compound may be prepared by known methods, such as those given in WO2008/70041, in particular from tert-butyl[1-(4-cyanophenyl)cyclobutyl]carbamate.

Step 4: tert-Butyl (1-{4-[bromo(phenyl)acetyl]phenyl}cyclobutyl)carbamate [Int-1A]

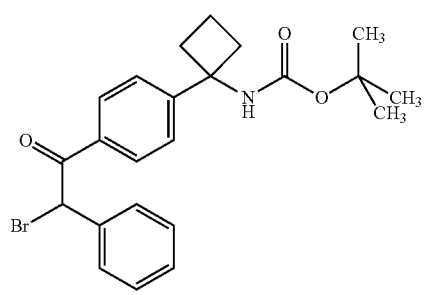 [SMILES: CC(C)(C)OC(=O)NC1(c2ccc(C(=O)C(Br)c3ccccc3)cc2)CCC1]

A mixture of tert-butyl {1-[4-(phenylacetyl)phenyl]cyclobutyl}carbamate (5.0 g, 13.68 mmol, 1.0 eq) and pyridinium hydrobromide perbromide (4.38 g, 13.68 mmol, 1.0 eq) in THF (78 mL) was stirred at 0° C. for 30 minutes. The mixture was partitioned between EtOAc and water and the organic phase washed respectively with aqueous sodium thiosulfate solution and brine, dried, filtered through a silicone coated filter paper and concentrated in vacuo to give the crude title compound (5.44 g, 93% purity by UPLC-MS) which was used without further purification.

UPLC-MS (Method 4): RT=1.49 min; m/z=442.21 (ES−, M−H, M=$C_{23}H_{26}{}^{79}BrNO_3$).

Step 5: tert-Butyl {1-[4-(6-methyl-3-phenylimidazo[1,2-b]pyridazin-2-yl)-phenyl]cyclobutyl}carbamate [Int-1]

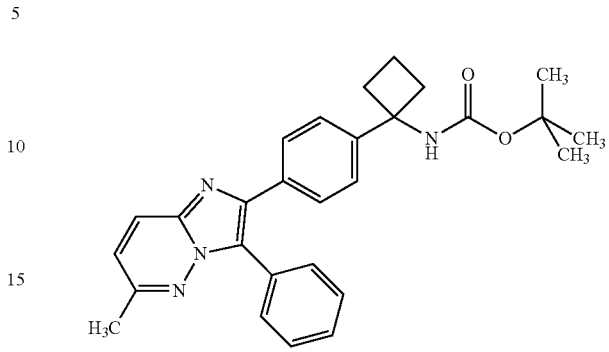

A mixture of crude tert-butyl (1-{4-[bromo(phenyl)acetyl]phenyl}cyclobutyl)carbamate that was prepared in a manner analgous to that described for Intermediate Example Int-1-A (1.00 g, ~80% purity, 1.87 mmol, 1.0 eq), 6-methylpyridazin-3-amine (CAS-Nr. 18591-82-7, 0.245 g, 2.24 mmol, 1.2 eq), N,N-diisopropylethylamine (0.33 mL, 1.87 mmol, 1.0 eq) and activated 3 Å molecular sieves in isopropanol (5.7 mL) was heated for 7 hours under reflux. On cooling, the mixture was partitioned between DCM and water, stirred vigorously and filtered through a silicone coated filter paper. The filtrate was concentrated in vacuo. UPLC analysis of the crude product indicated a purity of >90%. The crude product was used in the next step without further purification.

UPLC-MS (Method 1): RT=1.41 min; m/z=455.89 (M+H).

Intermediate Example Int-2 tert-Butyl {1-[4-(6-ethyl-3-phenylimidazo[1,2-b]pyridazin-2-yl)-phenyl]cyclobutyl}carbamate

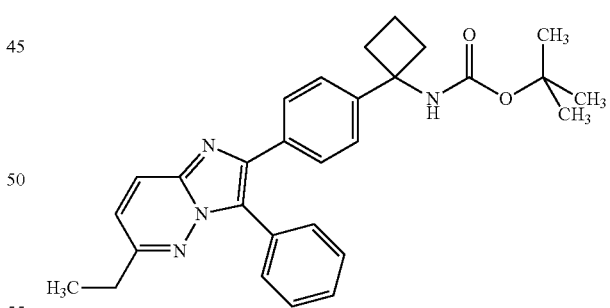

A mixture of crude tert-butyl (1-{4-[bromo(phenyl)acetyl]phenyl}cyclobutyl)-carbamate that was prepared in a manner analgous to that described for Intermediate Example Int-1-A (1.85 g, ~80% purity, 3.45 mmol, 1.0 eq), 6-ethylpyridazin-3-ammonium chloride (CAS-Nr. 1178585-42-6, 0.660 g, 4.14 mmol, 1.2 eq), N,N-diisopropylethylamine (1.20 mL, 6.89 mmol, 2.0 eq) and activated 3 Å molecular sieves in isopropanol (10.5 mL) was heated for 12 hours under reflux. On cooling, the mixture was partitioned between DCM and water, stirred vigorously and filtered through a silicone coated filter paper. The filtrate was concentrated in vacuo. The crude mixture was purified via MPLC (Biotage Isolera; 100 g SNAP cartridge: hexane→hexane/ethyl acetate 2/1) to give 700 mg (43% yield) of the title compound in 69% purity (UPLC).

UPLC-MS (Method 3): RT=1.53 min; m/z=469.34 (M+H).

Intermediate Example Int-3 tert-Butyl (1-{4-[3-phenyl-6-(trifluoromethyl)imidazo[1,2-b]pyridazin-2-yl]-phenyl}cyclobutyl)carbamate

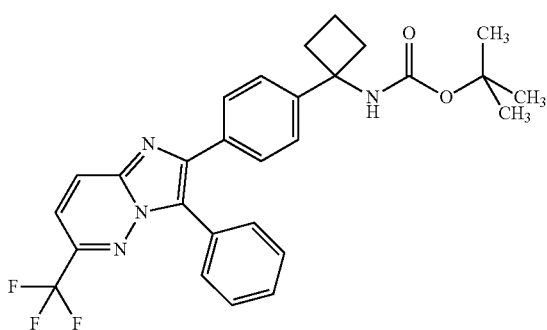 [SMILES: CC(C)(C)OC(=O)NC1(c2ccc(-c3nc4ccc(C(F)(F)F)nn4c3-c3ccccc3)cc2)CCC1]

A mixture of crude tert-butyl (1-{4-[bromo(phenyl)acetyl]phenyl}cyclobutyl)carbamate that was prepared in a manner analogous to that described for Intermediate Example Int-1-A (1.85 g, ~80% purity, 3.45 mmol, 1.0 eq), 6-(trifluoromethyl)pyridazin-3-amine (CAS-Nr. 935777-24-5, 0.674 g, 4.14 mmol, 1.2 eq), N,N-diisopropylethylamine (0.60 mL, 6.89 mmol, 1.0 eq) and activated 3 Å molecular sieves in isopropanol (10.5 mL) was heated for 7 hours under reflux. On cooling, the mixture was partitioned between DCM and water, stirred vigorously and filtered through a silicone coated filter paper. The filtrate was concentrated in vacuo. The crude mixture was purified via MPLC (Biotage Isolera; 100 g SNAP cartridge: hexane→hexane/ethyl acetate 2/1) to give 680 mg (34% yield) of the title compound.

UPLC-MS (Method 3): RT=1.56 min; m/z=509.29 (M+H).

Intermediate Example Int-4

Ethyl 2-(4-{1-[(tert-butoxycarbonyl)amino]cyclobutyl}phenyl)-3-phenylimidazo[1,2-b]pyridazine-6-carboxylate

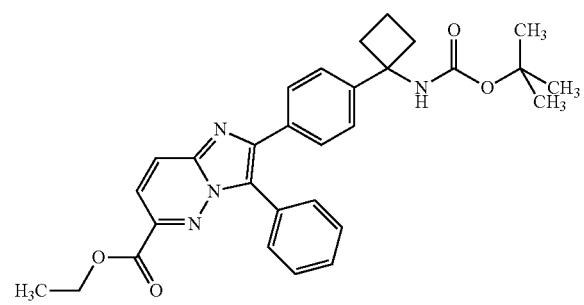 [SMILES: CCOC(=O)c1ccc2nc(-c3ccc(C4(NC(=O)OC(C)(C)C)CCC4)cc3)c(-c3ccccc3)n2n1]

A mixture of crude tert-butyl (1-{4-[bromo(phenyl)acetyl]phenyl}cyclobutyl)carbamate that was prepared in a manner analogous to that described for Intermediate Example Int-1-A (3.3 g, ~80% purity, 5.79 mmol), ethyl 6-aminopyridazine-3-carboxylate (CAS-Nr. 98548-01-7, 1 g, 5.57 mmol), N,N-diisopropylethylamine (0.97 mL, 5.57 mmol) and activated 3 Å molecular sieves in isopropanol (30.4 mL) was heated for 20 hours under reflux. On cooling the mixture was partitioned between DCM and water, stirred vigorously and filtered through a silicone coated filter paper. The filtrate was concentrated in vacuo, taken up in DCM and washed with dilute aqueous hydrochloric acid (1N) and brine, dried and concentrated in vacuo to give the crude title compound. Purification was achieved by chromatography on silica (gradient elution:Hexane:EtOAc 9:1 to Hexane:EtOAc 1:1) to give the title compound (2.80 g, 92% purity, 90% yield).

UPLC-MS (Method 3): RT=1.51 min; m/z=513.41 (M+H).

1H-NMR (400 MHz, d6-DMSO): δ=8.29 (d, 1H), 7.74 (d, 1H), 7.50-7.56 (m, 8H), 7.31 (d, 2H), 4.33 (q, 2H), 2.28-2.39 (m, 4H), 1.88-1.99 (m, 1H), 1.68-1.80 (m, 1H), 1.26-1.29 (m, 9H), 1.08 (br s, 3H).

Intermediate Example Int-5 tert-Butyl (1-{4-[3-phenyl-6-methoxyimidazo[1,2-b]pyridazin-2-yl]-phenyl}cyclobutyl)carbamate

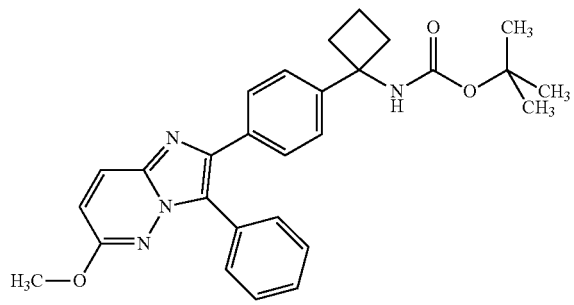 [SMILES: COc1ccc2nc(-c3ccc(C4(NC(=O)OC(C)(C)C)CCC4)cc3)c(-c3ccccc3)n2n1]

A mixture of crude tert-butyl (1-{4-[bromo(phenyl)acetyl]phenyl}cyclobutyl)carbamate that was prepared in a manner analogous to that described for Intermediate Example Int-1-A (0.67 g, 1.50 mmol), 3-amino-6-methoxypyridazine (CAS Registry No. 7252-84-8, 0.23 g, 1.80 mmol, 1.2 eq), N,N-diisopropylethylamine (0.74 mL, 1.50 mmol, 1.0 eq) and powdered activated 3 Å molecular sieves (10 g) in isopropanol (78 mL) was heated at the reflux temperature for 8 h. On cooling, the mixture was filtered through a pad of Celite. The Celite was washed with DCM, and the combined organics were washed with water, dried with sodium sulfate and concentrated under reduced pressure to give tert-butyl (1-{4-[3-phenyl-6-methoxyimidazo[1,2-b]pyridazin-2-yl]phenyl}cyclobutyl)carbamate (0.55 g, 78% yield).

UPLC-MS (Method 3): RT=1.52 min; m/z (rel intensity) 471 (95, (M+H)⁺), 943 (100, 2M+H)⁺); ES− m/z (rel intensity) 469 (20, (M−H)⁻).

1H-NMR (d6-DMSO): δ 1.00-1.20 (br s, 3H), 1.20-1.37 (br s, 6H), 1.65-1.81 br s, 1H), 1.85-2.00 (m, 1H), 2.25-2.38 m, 4H), 3.80 (s, 3H), 6.92 (d, J=9.6 Hz, 1H), 7.28 (d, J=8.5 Hz, 2H), 7.37-7.59 (m, 8H), 8.50 (d, J=9.6Hz, 1H).

Intermediate Example Int-6 tert-Butyl (1-{4-[3-phenyl-6,8-dibromoimidazo[1,2-b]pyridazin-2-yl]-phenyl}cyclobutyl)carbamate

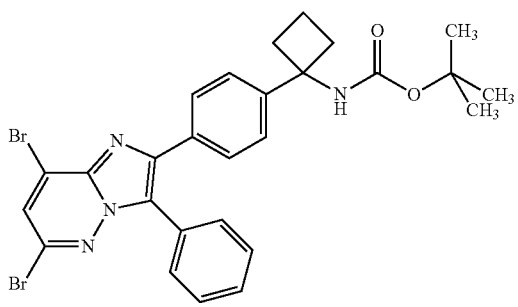 [SMILES: CC(C)(C)OC(=O)NC1(c2ccc(-c3nc4c(Br)cc(Br)nn4c3-c3ccccc3)cc2)CCC1]

A mixture of crude tert-butyl (1-{4-[bromo(phenyl)acetyl]phenyl}cyclobutyl)carbamate that was prepared in a manner analgous to that described for Intermediate Example Int-1-A (5.80 g, 13.1 mmol), 3-amino-4,6-dibromopyridazine (CAS Registry No. 1206487-35-5, 3.96 g, 15.7 mmol, 1.2 eq), N,N-diisopropylethylamine (2.3 mL, 13.0 mmol, 1.0 eq) and powdered activated 3 Å molecular sieves (10 g) in isopropanol (70 mL) was heated at the reflux temperature for 8 h. On cooling, the mixture was filtered through a pad of Celite. The Celite was washed with DCM, and the combined organics were washed with water, dried with sodium sulfate and concentrated under reduced pressure. The remaining material was purified using MPLC (Biotage Isolera; 100 g SNAP cartridge: 100% hexane 2.0 min., gradient to 75% hexane/25% EtOAc 2.5 min., 75% hexane/25% EtOAc 4.5 min., gradient to 50% hexane/50% EtOAc 2 min., 50% hexane/50% EtOAc 4.5 min., gradient to 100% EtOAc 2.5 min., 100% EtOAc 5.7 min.) to give partially purified tert-butyl (1-{4-[3-phenyl-6,8-dibromoimidazo[1,2-b]pyridazin-2-yl]phenyl}cyclobutyl)carbamate (2.65 g, ~82% pure, 28% yield):

UPLC-MS (Method 3): RT=1.67 min; m/z (rel intensity) 597 (50, (M+H)$^+$).

1H-NMR (d6-DMSO): δ 1.00-1.20 (br s, 3H), 1.20-1.37 (br s, 6H), 1.65-1.81 (m, 1H), 1.85-2.00 (m, 1H), 2.25-2.38 m, 4H), 3.80 (s, 3H), 6.92 (d, J=9.6 Hz, 1H), 7.28 (d, J=8.5 Hz, 2H), 7.37-7.59 (m, 8H), 8.50 (d, J=9.6 Hz, 1H).

The following examples were prepared in a manner analogous to Intermediate Example Int-6 by reacting the appropriate amine with tert-butyl (1-{4-[bromo(phenyl)acetyl]phenyl}cyclobutyl)carbamate [prepared in a manner analgous to that described for Intermediate Example Int-1A]

| Intermediate Example | Structure/Name | Characterization |
|---|---|---|
| Int-6.1 | tert-Butyl {1-[4-(8-bromo-6-chloro-3-phenylimidazo[1,2-b]pyridazin-2-yl)phenyl]cyclobutyl}carbamate | UPLC-MS (Method 3): RT = 1.65 min; m/z (rel intensity) 553 (90, (M + H)$^+$). |
| Int-6.2 | tert-Butyl {1-[4-(6-chloro-3-phenylimidazo[1,2-b]pyridazin-2-yl)phenyl]cyclobutyl}carbamate | UPLC-MS (Method 3): RT = 1.54 min; m/z (rel intensity) 475 (100, (M + H)$^+$), 949 (50, (2M + H)$^+$). 1H-NMR (d6-DMSO): δ 0.99-1.35 (br m, 9H), 1.65-1.80 (m, 1H), 1.86-2.01 (m, 1H), 2.26-2.39 m, 4H), 7.29 (d, J = 8.5 Hz, 2H), 7.38 (d, J = 9.4 Hz, 1H), 7.45-7.60 (m, 7H), 8.25 (d, J = 9.4 Hz, 1H). |

| Intermediate Example | Structure/Name | Characterization |
|---|---|---|
| Int-6.3 | 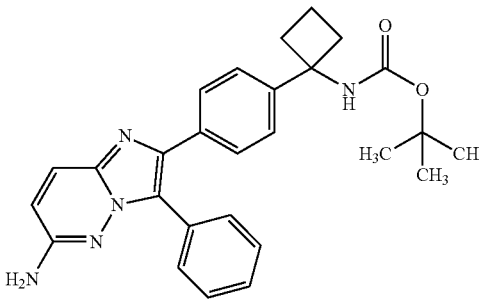<br>tert-Butyl {1-[4-(6-amino-3-phenylimidazo[1,2-b]pyridazin-2-yl)phenyl]cyclobutyl}carbamate | UPLC-MS (Method 3): RT = 1.32 min; m/z (rel intensity) 456 (100, (M + H)$^+$), 911 (50, (2M + H)$^+$); ES-m/z (rel intensity) 454 (100, (M − H)$^−$), 911 (10, (2M − H)$^−$).<br>1H-NMR (d6-DMSO): δ 1.00-1.35 (br m, 9H), 1.65-1.77 (m, 1H), 1.86-1.88 (m, 1H), 2.24-2.38 (m, 4H), 6.27 (s, 2H), 6.64 (d, J = 9.6 Hz, 1H), 7.29 (d, J = 8.3 Hz, 2H), 7.37-7.50 (m, 7H), 7.74 (d, J = 9.4 Hz, 1H). |
| Int-6.4 | 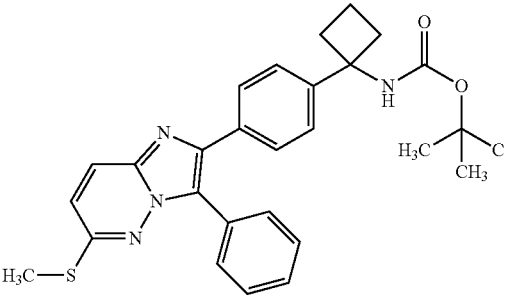<br>tert-Butyl (1-{4-[6-(methylsulfanyl)-3-phenylimidazo[1,2-b]pyridazin-2-yl]phenyl}cyclobutyl)carbamate | UPLC-MS (Method 3): RT = 1.60 min; m/z (rel intensity) 487 (100, (M + H)$^+$), 973 (30, (2M + H)$^+$).<br>1H-NMR (d6-DMSO): δ 1.00-1.37 (br m, 9H), 1.68-1.79 (m, 1H), 1.88-2.00 (m, 1H), 2.27-2.38 (m, 4H), 2.43 (s, 3H), 7.18 (d, J = 9.6 Hz, 1H), 7.29 (d, J = 8.3 Hz, 2H), 7.40-7.49 (m, 3H), 7.52 (d, J = 8.3 Hz, 2H), 7.57 (dm; J = 7.6 Hz, 2H), 7.98 (9.6 Hz, 1H). |
| Int-6.5 | 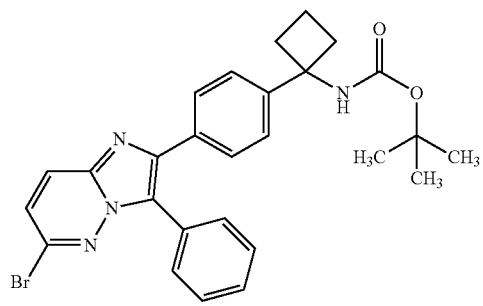<br>tert-Butyl {1-[4-(6-bromo-3-phenylimidazo[1,2-b]pyridazin-2-yl)phenyl]cyclobutyl}carbamate | UPLC-MS (Method 3): RT = 1.55 min; m/z (rel intensity) 519 (90, (M + H)$^+$).<br>1H-NMR (d6-DMSO): δ 0.98-1.32 (m, 9H), 1.65-1.79 (m, 1H), 1.85-2.00 (m, 2H), 2.26-2.39 (m, 4H), 7.29 (d, J = 8.5 Hz, 2H), 7.45 (d, J = 9.4 Hz, 1H), 7.47-7.57 (m, 7H), 8.14 (9.4 Hz, 1H). |

| Intermediate Example | Structure/Name | Characterization |
|---|---|---|
| Int-6.6 | 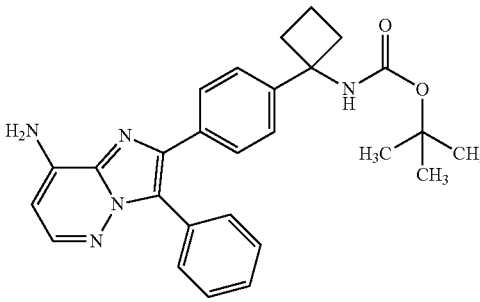<br>tert-Butyl {1-[4-(8-amino-3-phenylimidazo[1,2-b]pyridazin-2-yl)phenyl]cyclobutyl}carbamate | UPLC-MS (Method 3): RT = 1.39 min; m/z (rel intensity) 456 (100, (M + H)$^+$), 911 (20, (M + H)$^+$); ES-m/z (rel intensity) 454 (90, (M − H)$^−$). |

Intermediate Example Int-7 tert-Butyl (1-{4-[3-phenyl-6-bromo-8-methoxyimidazo[1,2-b]pyridazin-2-yl]-phenyl}cyclobutyl)carbamate

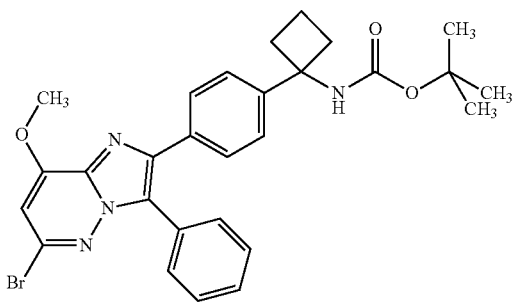

A solution of tert-butyl (1-{4-[3-phenyl-6,8-dibromoimidazo[1,2-b]pyridazin-2-yl]phenyl}cyclobutyl)carbamate that was prepared in a manner analgous to that described for Intermediate Example Int-6 (0.10 g, 0.17 mmol in MeOH (3 mL) was cooled with an ice bath and treated dropwise with sodium methoxide (0.5M in MeOH, 0.40 mL, 0.20 mmol, 1.2 eq). The resulting solution was allowed to warm to room temperature and was stirred at room temperature for 2 h, after which additional sodium methoxide was added (0.5M in methanol, 0.40 mL, 0.20 mmol, 1.2 eq). The resulting solution was allowed to warm to room temperature and was stirred at room temperature for 2 h, after which additional sodium methoxide was added (0.5M in MeOH, 0.40 mL, 0.20 mmol, 1.2 eq). The resulting solution was added to ice water, and the aqueous mixture was extracted with DCM (3×25 mL). The combined organic phases were dried (Na$_2$SO$_4$ anh.) and concentrated under reduced pressure to give impure tert-butyl (1-{4-[3-phenyl-6-bromo-8-methoxyimidazo[1,2-b]pyridazin-2-yl]phenyl}cyclobutyl) carbamate (102 mg, ~78% pure). This material was used without further purification:

UPLC-MS (Method 3): RT=1.67 min; m/z (rel intensity) 549 (90, (M+H)$^+$).

1H-NMR (d6-DMSO): δ 1.00-1.20 (br s, 3H), 1.20-1.37 (br s, 6H), 1.65-1.81 (br s, 1H), 1.85-2.00 (m, 1H), 2.25-2.38 m, 4H), 3.80 (s, 3H), 6.92 (d, J=9.6 Hz, 1H), 7.28 (d, J=8.5 Hz, 2H), 7.37-7.59 (m, 8H), 8.50 (d, J=9.6H, 1H).

The following examples were prepared in a manner analogous to Intermediate Example Int-7 by reacting the appropriate carbamate with sodium methoxide in methanol

| Intermediate Example | Structure/Name | Characterization |
|---|---|---|
| Int-7.1 | 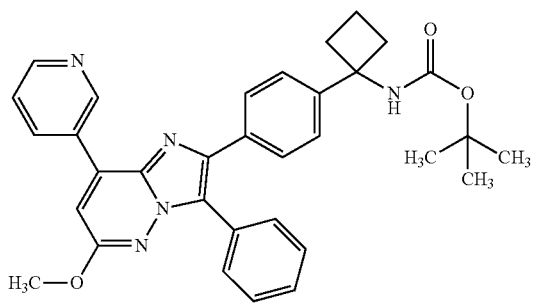 [SMILES: COc1cc(-c2cccnc2)c2nc(-c3ccc(C4(NC(=O)OC(C)(C)C)CCC4)cc3)c(-c3ccccc3)n2n1]<br>tert-Butyl (1-{4-[6-methoxy-3-phenyl-8-(pyridin-3-yl)imidazo[1,2-b]pyridazin-2-yl]phenyl}cyclobutyl)carbamate | UPLC-MS (Method 3): RT = 1.62 min; m/z (rel intensity) 548 (100, (M + H)$^+$). |

| Intermediate Example | Structure/Name | Characterization |
|---|---|---|
| Int-7.2 | tert-Butyl (1-{4-[6-methoxy-3-phenyl-8-(1H-pyrazol-4-yl)imidazo[1,2-b]pyridazin-2-yl]phenyl}cyclobutyl)carbamate | UPLC-MS (Method 3): RT = 1.60 min; m/z (rel intensity) 537 (100, (M + H)$^+$); ES-m/z (rel intensity) 535 (100, (M − H)$^−$). |
| Int-7.3 | tert-Butyl {1-[4-(6-chloro-8-methoxy-3-phenylimidazo[1,2-b]pyridazin-2-yl)phenyl]cyclobutyl}carbamate | UPLC-MS (Method 3): RT = 1.53 min; m/z (rel intensity) 505 (100, (M + H)$^+$); ES-m/z (rel intensity) 503 (10, (M − H)$^−$). 1H-NMR (d6-DMSO): δ 1.00-1.34 (br m, 9H), 1.66-1.79 (br s, 1H), 1.88-1.99 (m, 1 H), 2.26-2.38 m, 4H), 6.95 (s, 1 H), 7.27 (d, J = 8.6 Hz, 2H), 7.45-7.54 (m, 8H). |

The following examples were prepared in a manner analogous to Intermediate Example Int-7 by reacting the appropriate carbamate with sodium ethoxide in ethanol

| Intermediate Example | Structure/Name | Characterization |
|---|---|---|
| Int-7.4 | tert-Butyl {1-[4-(6-bromo-8-ethoxy-3-phenylimidazo[1,2-b]pyridazin-2-yl)phenyl]cyclobutyl}carbamate | UPLC-MS (Method 3): RT = 1.61 min; m/z (rel intensity) 563 (90, (M + H)$^+$), ES-m/z (rel intensity) 561 (5, (M − H)$^−$). |

Intermediate Example Int-8 tert-Butyl (1-{4-[3-phenyl-6,8-dimethoxyimidazo[1,2-b]pyridazin-2-yl]-phenyl}cyclobutyl)carbamate

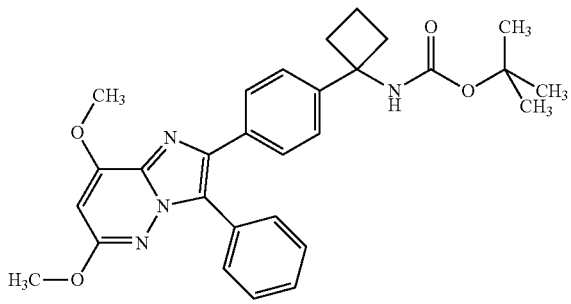 [SMILES: COc1cc(OC)c2nc(-c3ccc(C4(NC(=O)OC(C)(C)C)CCC4)cc3)c(-c3ccccc3)n2n1]

A solution of tert-butyl (1-{4-[3-phenyl-6,8-dibromoimidazo[1,2-b]pyridazin-2-yl]phenyl}cyclobutyl)carbamate that was prepared in a manner analgous to that described for Intermediate Example Int-6 (0.66 g, 1.10 mmol) in MeOH (10 mL) was treated dropwise with sodium methoxide (0.5M in MeOH, 11.0 mL, 5.51 mmol, 5.0 eq) and the resulting mixture was stirred at room temperature for 12 h. The resulting solution was irradiated at 120° C. in a microwave apparatus for 90 minutes. The resulting solution was added to ice water, and the aqueous mixture was extracted with DCM (3×50 mL). The combined organic phases were dried (Na$_2$SO$_4$ anh.) and concentrated under reduced pressure. The resulting material was purified using MPLC (Biotage Isolera; SNAP 10 g cartridge: 100% hexane 2.0 min., gradient to 70% hexane/30% DCM 3 min., 70% hexane/30% DCM 3 min., gradient to 50% hexane/50% DCM 4 min., 50% hexane/50% DCM 3.5 min., gradient to 95% hexane/5% DCM 5.5 min., 95% hexane/5% DCM 5.5 min.) to give tert-butyl (1-{4-[3-phenyl-6,8-dimethoxyimidazo[1,2-b]pyridazin-2-yl]phenyl}cyclobutyl)carbamate (0.19 g, 34%) followed by methyl (1-{4-[3-phenyl-6,8-dimethoxyimidazo[1,2-b]pyridazin-2-yl]phenyl}cyclobutyl)carbamate (0.029 g, 5.4%).

tert-Butyl (1-{4-[3-phenyl-6,8-dimethoxyimidazo[1,2-b]pyridazin-2-yl]phenyl}-cyclobutyl)carbamate UPLC-MS (Method 3): RT=1.53 min; m/z (rel intensity) 501 (50, (M+H)$^+$).

1H-NMR (d6-DMSO): δ 1.00-1.18 (br s, 3H), 1.22-1.35 (br s, 6H), 1.67-1.79 (br s, 1H), 1.87-1.98 (br s, 1H), 2.27-2.37 (m, 4H), 3.77 (s, 3H), 4.20 (s, 3H), 6.41 (s, 1H), 7.26 (d, J=8.3 Hz, 2H), 7.38-7.48 (m, 5H), 7.52-7.56 (m, 2H).

Methyl (1-{4-[3-phenyl-6,8-dimethoxyimidazo[1,2-b]pyridazin-2-yl]phenyl}-cyclobutyl)carbamate UPLC-MS (Method 3): RT=1.36 min; m/z (rel intensity) 459 (70, (M+H)$^+$); ES– m/z (rel intensity) 457 (10, (M–H)$^-$).

1H-NMR (d6-DMSO): δ 1.66-1.81 (m, 1H), 1.86-2.02 (br s, 1H), 2.35 (br t, J=7.3 Hz, 4H), 3.41 (br s, 3H), 3.76 (s, 3H), 4.20 (s, 3H), 6.41 (s, 1H), 7.26 (d, J=8.3 Hz, 2H), 7.38-7.51 (m, 5H), 7.51-7.57 (m, 2H), 7.87 (br s, 1H).

Intermediate Example Int-9

Methyl 2-(4-{1-[(tert-butoxycarbonyl)amino]cyclobutyl}phenyl)-8-methoxy-3-phenylimidazo[1,2-b]pyridazine-6-carboxylate

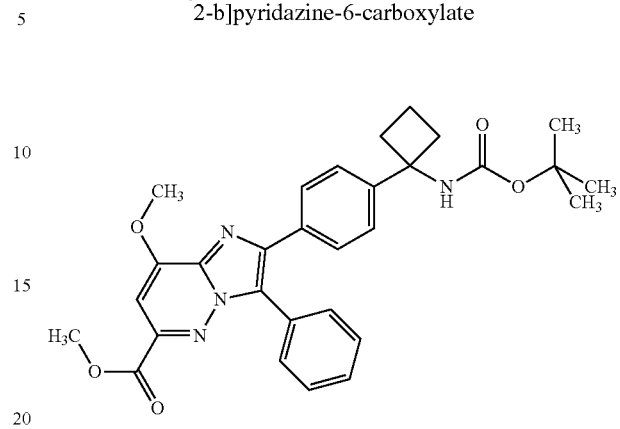

To a solution of tert-butyl (1-{4-[3-phenyl-6-bromo-8-methoxyimidazo[1,2-b]pyridazin-2-yl]phenyl}cyclobutyl)carbamate that was prepared in a manner analgous to that described for Intermediate Example Int-7 (0.41 g, 0.75 mmol) in MeOH (10 mL) and THF (1 mL) in an autoclave was added 1,1'-bis(diphenylphosphino)ferrocenepalladium (II) dichloride (0.12 g, 0.15 mmol, 0.20 equiv) and triethylamine (0.11 mL, 0.82 mmol, 1.1 equiv.). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 110° C., and stirred at this temperature for 22 h. The resulting solution was concentrated under reduced pressure. The resulting material was crystallized from MeOH to give methyl 2-(4-{1-[(tert-butoxycarbonyl)amino]cyclobutyl}phenyl)-8-methoxy-3-phenylimidazo[1,2-b]pyridazine-6-carboxylate (0.34 g, 85%):

UPLC-MS (Method 3): RT=1.46 min; m/z (rel intensity) 529 (70, (M+H)$^+$); ES– m/z (rel intensity) 527 (5, (M–H)$^-$).

1H-NMR (d6-DMSO): δ 1.00-1.18 (br s, 3H), 1.22-1.35 (br s, 6H), 1.67-1.79 (br s, 1H), 1.87-1.98 (br s, 1H), 2.27-2.37 (m, 4H), 3.77 (s, 3H), 4.20 (s, 3H), 6.41 (s, 1H), 7.26 (d, J=8.3 Hz, 2H), 7.38-7.48 (m, 5H), 7.52-7.56 (m, 2H).

Intermediate Example Int-10 tert-Butyl {1-[4-(6-carbamoyl-8-methoxy-3-phenylimidazo[1,2-b]pyridazin-2-yl)phenyl]cyclobutyl}carbamate (Approach 1)

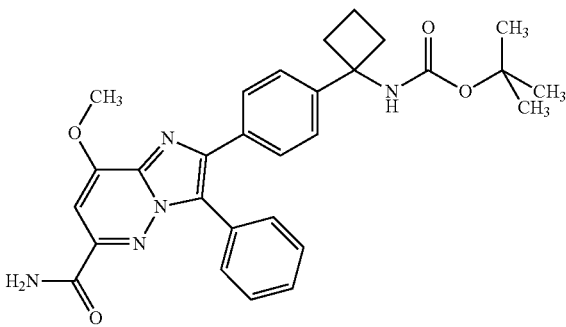 [SMILES: COc1cc(C(N)=O)nn2c(-c3ccccc3)c(-c3ccc(C4(NC(=O)OC(C)(C)C)CCC4)cc3)nc12]

A mixture of methyl 2-(4-{1-[(tert-butoxycarbonyl)amino]cyclobutyl}phenyl)-8-methoxy-3-phenylimidazo[1,2-b]pyridazine-6-carboxylate that was prepared in a manner analgous to that described for Intermediate Example Int-9 (0.20 g, 0.38 mmol) in a solution of ammonia in MeOH (7N, 15 mL) and THF (1 mL) was irradiated in a microwave apparatus at 130° C. for 90 min. The solids were collected by filtration to give tert-butyl {1-[4-(6-carbamoyl-8-methoxy-3-phenylimidazo[1,2-b]pyridazin-2-yl)phenyl]cyclobutyl}carbamate (0.12 g, 63%):

UPLC-MS (Method 3): RT=1.30 min; m/z (rel intensity) 514 (70, (M+H)$^+$); ES− m/z (rel intensity) 512 (90, (M−H)$^−$).

1H-NMR (d6-DMSO): δ 1.00-1.20 (br s, 3H), 1.20-1.39 (br s, 6H), 1.65-1.81 (br s, 1H), 1.86-2.02 (br m, 1H), 2.28-2.39 (m, 4H), 3.77 (s, 3H), 4.13 (s, 3H), 7.15 (s, 1H), 7.30 (d, J=8.3 Hz, 2H), 7.41-7.55 (m, 7H), 7.56-7.62 (m, 2H), 7.82 (br s, 1H).

The following examples were prepared in a manner analogous to Intermediate Example Int-10 by reacting the appropriate carbamate with a solution of ammonia in MeOH:

| Intermediate Example | Structure/Name | Characterization |
|---|---|---|
| Int-10.1 | 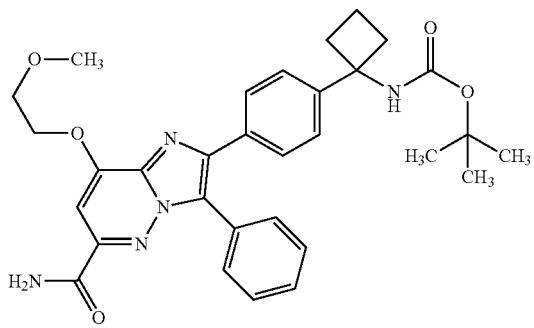 [SMILES: COCCOc1cc(C(N)=O)nn2c(-c3ccccc3)c(-c3ccc(C4(NC(=O)OC(C)(C)C)CCC4)cc3)nc12]<br>tert-Butyl (1-{4-[6-carbamoyl-8-(2-methoxyethoxy)-3-phenylimidazo[1,2-b]pyridazin-2-yl]phenyl}cyclobutyl)carbamate | UPLC-MS (Method 3): RT = 1.29 min; m/z (rel intensity) 558 (100, (M + H)$^+$); ES-m/z (rel intensity) 556 (100, (M − H)$^−$). |

The following examples were prepared in a manner analogous to Intermediate Example Int-10 by reacting the appropriate carbamate with a solution of methylamine in MeOH:

| Intermediate Example | Structure/Name | Characterization |
|---|---|---|
| Int-10.2 | 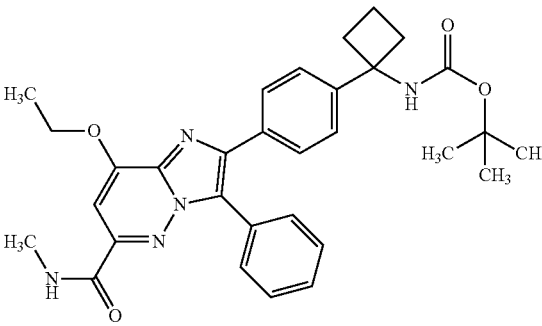<br>tert-Butyl (1-{4-[8-ethoxy-6-(methylcarbamoyl)-3-phenylimidazo[1,2-b]pyridazin-2-yl]phenyl}cyclobutyl)carbamate | UPLC-MS (Method 3): RT = 1.42 min; m/z (rel intensity) 542 (70, (M + H)$^+$); ES-m/z (rel intensity) 540 (30, (M − H)$^−$). |

| Intermediate Example | Structure/Name | Characterization |
|---|---|---|
| Int-10.3 | 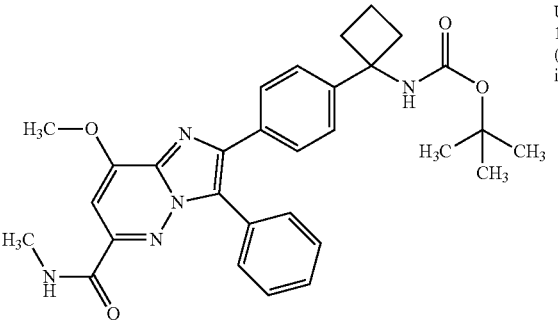<br>tert-Butyl (1-{4-[8-methoxy-6-(methylcarbamoyl)-3-phenylimidazo[1,2-b]pyridazin-2-yl]phenyl}cyclobutyl) carbamate | UPLC-MS (Method 3): RT = 1.35 min; m/z (rel intensity) 527 (70, (M + H)$^+$); ES-m/z (rel intensity) 525 (20, (M − H)$^-$). |

Intermediate Example Int-11 tert-Butyl {1-[4-(8-methoxy-3-phenylimidazo[1,2-b]pyridazin-2-yl)-phenyl]cyclobutyl}carbamate

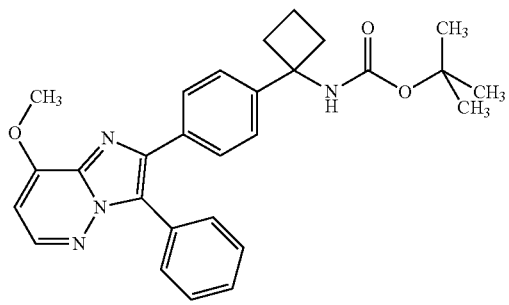 [SMILES: COc1ccnn2c(-c3ccccc3)c(-c3ccc(C4(NC(=O)OC(C)(C)C)CCC4)cc3)nc12]

To a mixture of tert-butyl (1-{4-[3-phenyl-6-bromo-8-methoxyimidazo[1,2-b]pyridazin-2-yl]phenyl}cyclobutyl) carbamate that was prepared in a manner analgous to that described for Intermediate Example Int-7 (0.075 g, 0.14 mmol) and 5% palladium on carbon (0.007 g) in DMF (1 mL) was added a solution of sodium formate (0.074 g, 1.09 mmol, 8.0 eq) in water (0.2 mL). The resulting mixture was stirred at 80° C. for 3 h, diluted with MeOH (10 mL) and stirred at room temperature for 1 h. The resulting solution was filtered through a membrane filter, and the solids were washed with MeOH (1 mL). The resulting solution was diluted with EtOAc (25 mL), washed with water (2×25 mL), dried (Na$_2$SO$_4$ anh.) and concentrated under reduced pressure to give tert-butyl {1-[4-(8-methoxy-3-phenyl imidazo [1,2-b]pyridazin-2-yl)phenyl]cyclobutyl}carbamate approximately 75% purity (0.058 g, 90%):

UPLC-MS (Method 3): RT=1.44 min; m/z (rel intensity) 471 (100, (M+H)$^+$); ES− m/z (rel intensity) 512 (90, (M−H)$^-$).

The following examples were prepared in a manner analogous to Intermediate Example Int-11 by reacting the appropriate carbamate with sodium formate and a palladium catalyst

| Intermediate Example | Structure/Name | Characterization |
|---|---|---|
| Int-11.1 | 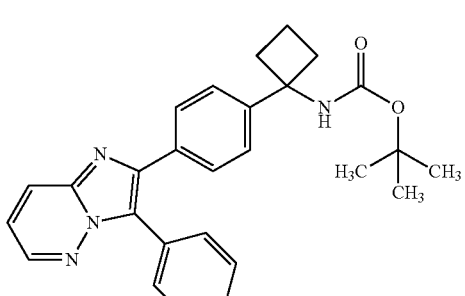<br>tert-Butyl {1-[4-(3-phenylimidazo[1,2-b]pyridazin-2-yl)phenyl]cyclobutyl}carbamate | UPLC-MS (Method 3): RT = 1.33 min; m/z (rel intensity) 441 (100, (M + H)$^+$), 881 (50, (2M + H)$^+$); ES-m/z (rel intensity) 439 (100, (M − H)$^-$), 879 (10, (2M − H)$^-$). |

| Intermediate Example | Structure/Name | Characterization |
|---|---|---|
| Int-11.2 | tert-Butyl (1-{4-[3-phenyl-8-(1H-pyrazol-3-yl)imidazo[1,2-b]pyridazin-2-yl]phenyl}cyclobutyl)carbamate | UPLC-MS (Method 3): RT = 1.49 min; m/z (rel intensity) 507 (100, (M + H)$^+$); ES-m/z (rel intensity) 505 (100, (M − H)$^−$). |
| Int-11.3 | tert-Butyl {1-[4-(8-hydroxy-3-phenylimidazo[1,2-b]pyridazin-2-yl)phenyl]cyclobutyl}carbamate | UPLC-MS (Method 3): RT = 0.83 min; m/z (rel intensity) 457 (100, (M + H)$^+$), 913 (70, (2M + H)$^+$); ES-m/z (rel intensity) 455 (100, (M − H)$^−$). |
| Int-11.4 | tert-Butyl (1-{4-[8-(4-fluorophenyl)-3-phenylimidazo[1,2-b]pyridazin-2-yl]phenyl}cyclobutyl)carbamate | UPLC-MS (Method 3): RT = 1.49 min; m/z (rel intensity) 535 (100, (M + H)$^+$); ES-m/z (rel intensity) 533 (100, (M − H)$^−$). |

Intermediate Example Int-12 tert-Butyl {1-[4-(8-methoxy-3-phenyl-6-vinylimidazo[1,2-b]pyridazin-2-yl)-phenyl]cyclobutyl}carbamate

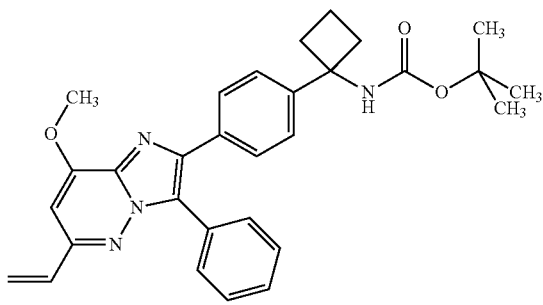 [SMILES: C=Cc1cc(OC)c2nc(-c3ccc(C4(NC(=O)OC(C)(C)C)CCC4)cc3)c(-c3ccccc3)n2n1]

A mixture of tert-butyl (1-{4-[3-phenyl-6-bromo-8-methoxyimidazo[1,2-b]pyridazin-2-yl]phenyl}cyclobutyl)carbamate that was prepared in a manner analgous to that described for Intermediate Example Int-7 (0.30 g, 0.54 mmol) and tetrakis(triphenylphosphine)palladium(0) (0.006 g, 0.005 mmol, 10 mol %) in 1,2-dimethoxyethane (4 mL) was stirred under an argon atmosphere for 10 min, then was sequentially treated with $K_2CO_3$ (0.075 g, 0.54 mmol, 1.0 eq), water (1.5 mL) and vinylboronic acid anhydride pyridine complex (prepared as described in *J. Org. Chem.* 2002, 67, 4968; 0.13 g, 0.54 mmol, 1.0 eq). The resulting mixture was heated at the reflux temperature for 16 h, then was added to water (15 mL). The resulting mixture was extracted with EtOAc (2×25 mL). The combined organic phases were washed with water (25 mL), dried ($Na_2SO_4$), and concentrated under reduced pressure. The resulting material was purified using MPLC (Biotage Isolera; Snap 10 g cartridge, 100% hexane 1.5 min, gradient to 80% hexane/20% EtOAc 1.0 min, 80% hexane/20% EtOAc 2.0 min, gradient to 50% hexane/50% EtOAc 3.0 min, 50% hexane/50% EtOAc 4.0 min, gradient to 100% EtOAc 4.5 min, 100% EtOAc 7.7 min) to give tert-butyl {1-[4-(8-methoxy-3-phenyl-6-vinylimidazo[1,2-b]pyridazin-2-yl)phenyl]cyclobutyl}carbamate (0.25 g, 92%):

UPLC-MS (Method 3): RT=1.55 min; m/z (rel intensity) 497 (100, (M+H)$^+$); ES− m/z (rel intensity) 495 (10, (M−H)$^-$).

1H-NMR (d6-DMSO): δ 0.80-1.37 (br m, 9H), 1.65-1.80 (br s, 1H), 1.85-2.01 (br m, 1H), 2.27-2.37 (m, 4H), 4.02 (s, 3H), 5.63 (d, J=11.3 Hz, 1H), 6.27 (d, J=17.7 Hz, 1H), 6.64 (dd, J=10.0, 17.7 Hz, 1H), 7.04 (s, 1H), 7.27 (d, J=8.5 Hz, 2H), 7.42-7.55 (m, 8H).

The following examples were prepared in a manner analogous to Intermediate Example Int-12 by reacting the appropriate carbamate with vinylboronic acid anhydride pyridine complex

| Intermediate Example | Structure/Name | Characterization |
|---|---|---|
| Int-12.1 | tert-Butyl {1-[4-(3-phenyl-6,8-divinylimidazo[1,2-b]pyridazin-2-yl)phenyl]cyclobutyl}carbamate | UPLC-MS (Method 3): RT = 1.71 min; m/z (rel intensity) 493 (100, (M + H)$^+$), 985 (80, (2M + H)$^+$); ES-m/z (rel intensity) 491 (10, (M − H)$^-$). |
| Int-12.2 | tert-Butyl (1-{4-[3-phenyl-8-(1H-pyrazol-3-yl)-6-vinylimidazo[1,2-b]pyridazin-2-yl]phenyl}cyclobutyl)carbamate | UPLC-MS (Method 3): RT = 1.59 min; m/z (rel intensity) 533 (100, (M + H)$^+$); ES-m/z (rel intensity) 531 (100, (M − H)$^-$). |

Intermediate Example Int-13 tert-Butyl {1-[4-(6-ethyl-8-methoxy-3-phenylimidazo[1,2-b]pyridazin-2-yl)-phenyl]cyclobutyl}carbamate

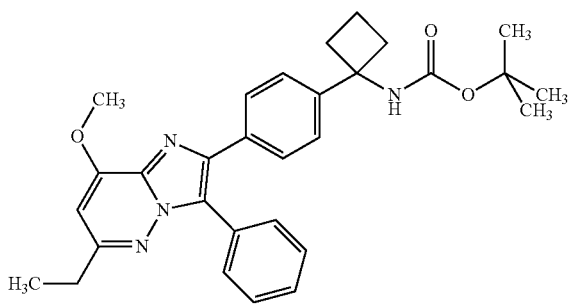 [SMILES: CCc1cc(OC)c2nc(-c3ccc(C4(NC(=O)OC(C)(C)C)CCC4)cc3)c(-c3ccccc3)n2n1]

A solution of tert-butyl {1-[4-(8-methoxy-3-phenyl-6-vinylimidazo[1,2-b]pyridazin-2-yl)phenyl]cyclobutyl}carbamate that was prepared in a manner analogous to that described for Intermediate Example Int-12 (0.20 g, 0.40 mmol) in methanol (8 mL) was hydrogenated using an H-Cube flow reactor (Pd/C cartridge). The resulting solution was concentrated under reduced pressure to give tert-butyl {1-[4-(6-ethyl-8-methoxy-3-phenylimidazo[1,2-b]pyridazin-2-yl)phenyl]cyclobutyl}carbamate (0.20 g, 100%):

1H-NMR (d6-DMSO): δ 1.08-1.35 (br m, 9H), 1.19 (t, J=7.5 Hz, 3H), 1.66-1.83 (br s, 1H), 1.85-2.03 (br m, 1H), 2.26-2.37 (m, 4H), 2.68 (q, J=7.5 Hz, 2H), 4.05 (s, 3H), 6.70 (s, 1H), 7.26 (d, J=8.5 Hz, 2H), 7.41-7.53 (m, 8H).

The following examples were prepared in a manner analogous to Intermediate Example Int-13 by hydrogenation of the appropriate carbamate using an H-Cube flow reactor

| Intermediate Example | Structure/Name | Characterization |
|---|---|---|
| Int-13.1 | tert-Butyl {1-[4-(6,8-diethyl-3-phenylimidazo[1,2-b]pyridazin-2-yl)phenyl]cyclobutyl}carbamate | UPLC-MS (Method 3): RT = 1.77 min; m/z (rel intensity) 497 (100, (M + H)+). |
| Int-13.2 | tert-Butyl (1-{4-[6-ethyl-3-phenyl-8-(1H-pyrazol-3-yl)imidazo[1,2-b]pyridazin-2-yl]phenyl}cyclobutyl)carbamate | UPLC-MS (Method 3): RT = 1.62 min; m/z (rel intensity) 535 (100, (M + H)+); ES-m/z (rel intensity) 533 (50, (M − H)−). |

Intermediate Example Int-14 tert-Butyl (1-{4-[6-chloro-3-phenyl-8-(pyridin-3-yl)imidazo[1,2-b]pyridazin-2-yl]phenyl}cyclobutyl)carbamate

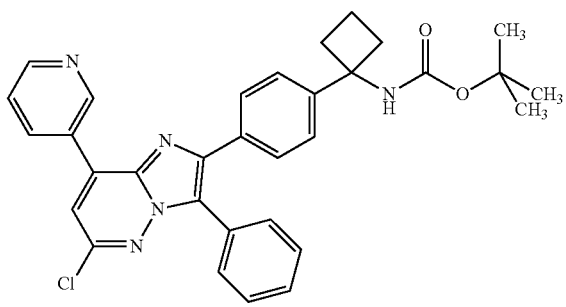 [SMILES: CC(C)(C)OC(=O)NC1(c2ccc(-c3nc4c(-c5cccnc5)cc(Cl)nn4c3-c3ccccc3)cc2)CCC1]

A mixture of tert-butyl {1-[4-(8-bromo-6-chloro-3-phenylimidazo[1,2-b]pyridazin-2-yl)phenyl]cyclobutyl}carbamate that was prepared in a manner analogous to that described for Intermediate Example Int-7.1 (0.15 g, 0.27 mmol), 3-pyridineboronic acid (0.040 g, 0.33 mmol, 1.2 equiv.), 1,1'-bis(diphenylphosphino)ferrocenepalladium(II) dichloride (0.022 g, 0.03 mmol, 0.1 equiv.), $Na_2CO_3$ (0.086 g, 0.81 mmol, 3.0 equiv.), in dioxane (2.9 mL) and water (0.4 mL) was bubbled with Ar, then placed under an argon atmosphere and was irradiated in a microwave apparatus at 105° C. for 90 min. The reaction mixture was then added to a mixture of water (10 mL), a saturated aqueous $NH_4Cl$ solution (10 mL) and $CH_2Cl_{12}$ (20 mL). The resulting mixture was stirred strongly for 30 minutes. The organic phase was separated, dried ($Na_2SO_4$ anh), and concentrated under reduced pressure. The resulting material was purified using MPLC (Biotage Isolera; Snap 10 g cartridge, 100% hexane 2.0 min, gradient to 80% hexane/20% EtOAc 1.0 min, 80% hexane/20% EtOAc 3.0 min, gradient to 50% hexane/50% EtOAc 2.5 min, 50% hexane/50% EtOAc 3.5 min, gradient to 100% EtOAc 3.0 min, 100% EtOAc 4.8 min) to give tert-butyl (1-{4-[6-chloro-3-phenyl-8-(pyridin-3-yl)imidazo[1,2-b]pyridazin-2-yl]phenyl}cyclobutyl)carbamate (0.046 g, 31%):

UPLC-MS (Method 3): RT=1.62 min; m/z (rel intensity) 552 (100, (M+H)$^+$); ES– m/z (rel intensity) 550 (10, (M–H)$^-$).

1H-NMR (d6-DMSO): δ 0.98-1.37 (br m, 9H), 1.66-1.81 (br s, 1H), 1.85-2.00 (br m, 1H), 2.27-2.38 (m, 4H), 7.31 (d, J=8.5 Hz, 2H), 7.49-7.58 (m, 7H), 7.64 (ddd, J=7.0, 4.7, 0.8 Hz, 1H), 7.85 (s, 1H), 8.75 (ddd, J=4.9, 1.5 Hz, 1H), 8.81 (app dt, J=8.1, 1.9 Hz, 1H), 9.56 (dd, J=2.3, 0.6 Hz, 1H).

The following examples were prepared in a manner analogous to Intermediate Example Int-14 by reacting the appropriate carbamate with [1-(tert-butoxycarbonyl)-1H-pyrazol-4-yl]boronic acid

| Intermediate Example | Structure/Name | Characterization |
| --- | --- | --- |
| Int-14.1 | tert-Butyl (1-{4-[6-chloro-3-phenyl-8-(1H-pyrazol-4-yl)imidazo[1,2-b]pyridazin-2-yl]phenyl}cyclobutyl)carbamate | UPLC-MS (Method 3): RT = 1.55 min; m/z (rel intensity) 541 (100, (M + H)$^+$); ES-m/z (rel intensity) 539 (80, (M – H)$^-$). |

The following examples were prepared in a manner analogous to Intermediate Example Int-14 by reacting the appropriate carbamate with [1-(tert-butoxycarbonyl)-1H-pyrazol-5-yl]boronic acid

| Intermediate Example | Structure/Name | Characterization |
|---|---|---|
| Int-14.2 | 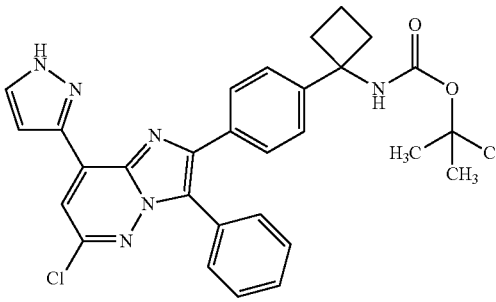<br>tert-Butyl (1-{4-[6-chloro-3-phenyl-8-(1H-pyrazol-3-yl)imidazo[1,2-b]pyridazin-2-yl]phenyl}cyclobutyl)carbamate | UPLC-MS (Method 3): RT = 1.59 min; m/z (rel intensity) 541 (100, (M + H)$^+$); ES-m/z (rel intensity) 539 (50, (M − H)$^-$). 1H-NMR (d6-DMSO): δ 1.00-1.37 (br m, 9H), 1.68-1.80 (br s, 1H), 1.88-2.00 (br m, 1H), 2.30-2.38 (m, 3H), 7.32 (d, J = 8.6 Hz, 2H), 7.49-7.56 (m, 5H), 7.61 (br d, J = 8.1 Hz, 2H), 7.20-7.70 (m, 2H), 7.98 (br s, 1H). |

The following examples were prepared in a manner analogous to Intermediate Example Int-14 by reacting the appropriate carbamate with (1-methyl-1H-pyrazol-5-yl)boronic acid

| Intermediate Example | Structure/Name | Characterization |
|---|---|---|
| Int-14.3 | 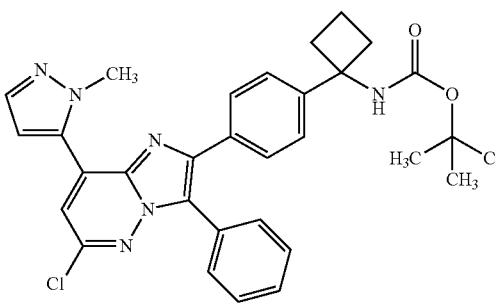<br>tert-Butyl (1-{4-[6-chloro-8-(1-methyl-1H-pyrazol-5-yl)-3-phenylimidazo[1,2-b]pyridazin-2-yl]phenyl}cyclobutyl)carbamate | UPLC-MS (Method 3): RT = 1.59 min; m/z (rel intensity) 555 (80, (M + H)$^+$); ES-m/z (rel intensity) 553 (20, (M − H)$^-$). 1H-NMR (d6-DMSO): δ 1.00-1.37 (br m, 9H), 1.65-1.80 (br s, 1H), 1.85-1.89 (br m, 1H), 2.26-2.38 (m, 4H), 4.05 (s, 3H), 6.92 (br s, 0.7 H), 7.30 (d, J = 8.5 Hz, 2H), 7.49-7.57 (m, 8H), 7.64 (d, J = 2.0 Hz, 1H), 7.20-7.70 (m, 2H), 7.96 (s, 0.3H). |

The following examples were prepared in a manner analogous to Intermediate Example Int-14 by reacting the appropriate carbamate with (4-fluorophenyl)boronic acid

| Intermediate Example | Structure/Name | Characterization |
|---|---|---|
| Int-14.4 | tert-Butyl (1-{4-[6-(4-fluorophenyl)-3-phenylimidazo[1,2-b]pyridazin-2-yl]phenyl}cyclobutyl)carbamate | UPLC-MS (Method 3): RT = 1.64 min; m/z (rel intensity) 535 (100, (M + H)+); ES-m/z (rel intensity) 533 (10, (M − H)−). |
| Int-14.5 | tert-Butyl (1-{4-[6-chloro-8-(4-fluorophenyl)-3-phenylimidazo[1,2-b]pyridazin-2-yl]phenyl}cyclobutyl)carbamate | UPLC-MS (Method 3): RT = 1.77 min; m/z (rel intensity) 569 (100, (M + H)+). |

The following examples were prepared in a manner analogous to Intermediate Example Int-14 by reacting the appropriate carbamate with cyclopropylboronic acid

| Intermediate Example | Structure/Name | Characterization |
|---|---|---|
| Int-14.6 | tert-Butyl {1-[4-(6-chloro-8-cyclopropyl-3-phenylimidazo[1,2-b]pyridazin-2-yl)phenyl]cyclobutyl}carbamate | UPLC-MS (Method 3): RT = 1.70 min; m/z (rel intensity) 515 (100, (M + H)+). |

The following examples were prepared in a manner analogous to Intermediate Example Int-14 by reacting the appropriate carbamate with pyridin-4-ylboronic acid 100% EtOAc 4.5 min) to give 2-(4-{1-[(tert-butoxycarbonyl)amino]cyclobutyl}phenyl)-3-phenylimidazo[1,2-b]pyridazin-8-yl trifluoromethanesulfonate (0.15 mg, 34%):

| Intermediate Example | Structure/Name | Characterization |
|---|---|---|
| Int-14.7 | tert-butyl (1-{4-[6-bromo-3-phenyl-8-(pyridin-4-yl)imidazo[1,2-b]pyridazin-2-yl]phenyl}cyclobutyl)carbamate | UPLC-MS (Method 3): RT = 1.63 min; m/z (rel intensity) 596 (100, (M + H)+). 1H-NMR (d6-DMSO): δ 1.00-1.00-1.38 (m, 9H), 1.66-1.80 (br s, 1H), 1.85-2.00 (br m, 1H), 2.28-2.38 (m, 4H), 7.32 (d, J = 8.5 Hz, 2H), 7.47-7.58 (m, 8H), 7.94 (s, 1H), 8.39 (dm, J = 6.2 Hz, 2H), 8.81 (dm, J = 6.0 Hz, 2H). |

Intermediate Example Int-15

2-(4-{1-[(tert-Butoxycarbonyl)amino]cyclobutyl}phenyl)-3-phenylimidazo[1,2-b]pyridazin-8-yl trifluoromethanesulfonate

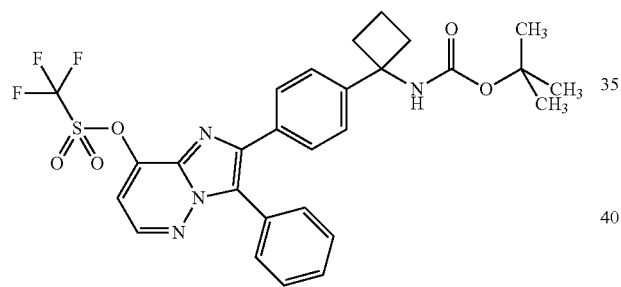

To a solution of tert-butyl {1-[4-(8-hydroxy-3-phenylimidazo[1,2-b]pyridazin-2-yl)phenyl]cyclobutyl}carbamate that was prepared in a manner analgous to that described for Intermediate Example Int-11.3 (0.34 g, 0.75 mmol) and triethylamine (0.25 mL, 1.73 mmol, 2.3 equiv.) in DCM (3 mL) at −20° C. under argon was added dropwise trifluoromethanesulfonic anhydride (0.15 mL, 0.90 mmol, 1.2 equiv.). The reaction mixture was allowed to slowly warm to room temperature, was stirred for 1 h, and was cooled to −10° C. Additional triethylamine (0.25 mL, 1.73 mmol, 2.3 equiv.) and trifluoromethanesulfonic anhydride (0.15 mL, 0.90 mmol, 1.2 equiv.) was added. The mixture was allowed to warm to room temperature and was stirred for 3 h. The mixture was treated with a 50% water/50% saturated NaHCO₃ solution (10 mL). The aqueous mixture was extracted with DCM (3×10 mL), dried (Na₂SO₄ anh.), and concentrated under reduced pressure. The resulting material was purified using MPLC (Biotage Isolera; Snap 10 g cartridge, 100% hexane 2.0 min, gradient to 80% hexane/20% EtOAc 1.0 min, 80% hexane/20% EtOAc 3.0 min, gradient to 50% hexane/50% EtOAc 3.5 min, 50% hexane/50% EtOAc 4.0 min, gradient to 100% EtOAc 3.5 min, UPLC-MS (Method 3): RT=1.63 min; m/z (rel intensity) 588 (40, (M+H)+); ES− m/z (rel intensity) 587 (20, (M−H)−).

1H-NMR (d6-DMSO): δ 1.00-1.36 (br m, 9H), 1.68-1.80 (br s, 1H), 1.88-2.00 (br m, 1H), 2.30-2.38 (m, 4H), 7.33 (d, J=8.6 Hz, 2H), 7.47-7.57 (m, 7H), 7.62, (d, J=5.3 Hz, 1H), 8.60 (d, J=5.3 Hz, 1H).

Intermediate Example Int-16 tert-Butyl {1-[4-(6-chloro-8-hydroxy-3-phenylimidazo[1,2-b]pyridazin-2-yl)-phenyl]cyclobutyl}carbamate

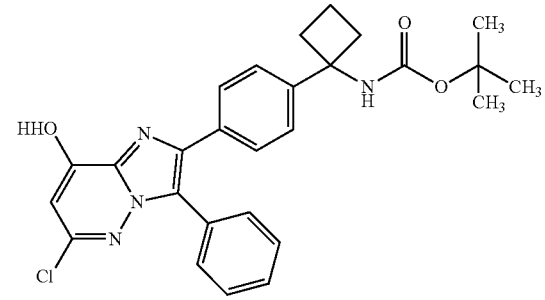

To a solution of tert-butyl {1-[4-(8-bromo-6-chloro-3-phenylimidazo[1,2-b]pyridazin-2-yl)phenyl]cyclobutyl}carbamate that was prepared in a manner analgous to that described for Intermediate Example Int-6.1 (2.49 g, 4.50 mmol) in DMF (63 mL) was added potassium acetate (2.21 g, 22.5 mmol, 5.0 equiv.), and the resulting mixture was irradiated in a microwave apparatus at 140° C. for 90 min. The resulting mixture was added to ice water (200 mL). The water mixture was extracted with a 4:1 DCM/isopropanol solution (4×50 mL). The combined organic phases were dried (Na₂SO₄ anh.), and concentrated under reduced pressure to give a brown oil (2.6 g). The oil was triturated with MeOH to give tert-butyl {1-[4-(6-chloro-8-hydroxy-3-phenylimidazo[1,2-b]pyridazin-2-yl)phenyl]cyclobutyl}carbamate as a yellow powder (0.60 g, 27%):

UPLC-MS (Method 3): RT=0.93 min; m/z (rel intensity) 491 (100, (M+H)⁺), 981 (80 (2M+H)⁺); ES− m/z (rel intensity) 489 (100, (M−H)⁻).

1H-NMR (d6-DMSO): δ 1.00-1.35 (br m, 9H), 1.65-1.80 (br s, 1H), 1.86-1.99 (br m, 1H), 2.25-2.39 (m, 5H), 6.45 (s, 1H), 7.29 (d, J=8.7 Hz, 2H), 7.42-7.52 (m, 8H).

Intermediate Example Int-17 tert-Butyl (1-{4-[8-(benzyloxy)-6-chloro-3-phenylimidazo[1,2-b]pyridazin-2-yl]phenyl}cyclobutyl)carbamate

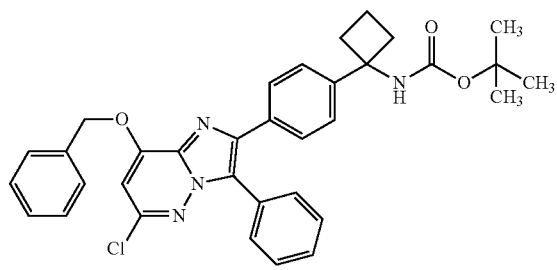 [SMILES: CC(C)(C)OC(=O)NC1(c2ccc(-c3nc4c(OCc5ccccc5)cc(Cl)nn4c3-c3ccccc3)cc2)CCC1]

To a solution of tert-butyl {1-[4-(6-chloro-8-hydroxy-3-phenylimidazo[1,2-b]pyridazin-2-yl)phenyl]cyclobutyl}carbamate that was in a manner analgous to that described for Intermediate Example Int-16 (1.90 g, 3.87 mmol) in DMF (50 mL) was added cesium carbonate (6.08 g, 11.6 mmol, 3.0 equiv.) and benzyl bromide (0.58 mL, 4.84 mmol, 1.25 equiv.), and the resulting mixture was irradiated in a microwave apparatus at 140° C. for 90 min. The resulting mixture stirred at room temperature for 16 h. The resulting mixture was added to ice water 100 mL). The aqueous mixture was extracted with a 4:1 DCM/isopropanol solution (3×50 mL). The combined organic phases were dried (Na₂SO₄ anh.), and concentrated under reduced pressure. The resulting oil was triturated with ethanol to give tert-butyl (1-{4-[8-(benzyloxy)-6-chloro-3-phenylimidazo[1,2-b]pyridazin-2-yl]phenyl}cyclobutyl)carbamate as a powder (0.93 g, 41%):

UPLC-MS (Method 3): RT=1.51 min; m/z (rel intensity) 581 (100, (M+H)⁺); ES− m/z (rel intensity) 579 (90, (M−H)⁻).

1H-NMR (d6-DMSO): δ 0.98-1.35 (br m, 9H), 1.64-1.78 (br s, 1H), 1.84-2.00 (br m, 1H), 2.25-2.37 (m, 4H), 5.48 (s, 2H), 7.08 (s, 1H), 7.26 (d, J=8.5 Hz, 2H), 7.37-7.57 (m, 13H).

Intermediate Example Int-18

Methyl 2-(4-{1-[(tert-butoxycarbonyl)amino]cyclobutyl}phenyl)-8-hydroxy-3-phenylimidazo[1,2-b]pyridazine-6-carboxylate

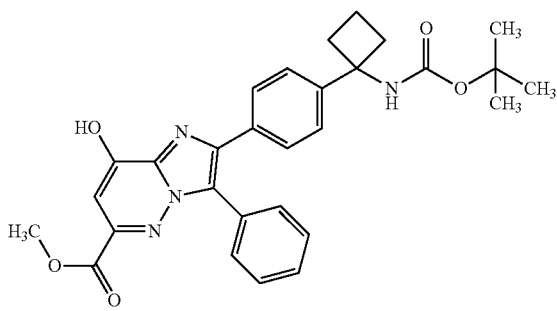 [SMILES: COC(=O)c1cc(O)c2nc(-c3ccc(C4(NC(=O)OC(C)(C)C)CCC4)cc3)c(-c3ccccc3)n2n1]

To a solution of tert-butyl (1-{4-[8-(benzyloxy)-6-chloro-3-phenylimidazo[1,2-b]pyridazin-2-yl]phenyl}cyclobutyl)carbamate that was prepared in a manner analgous to that described for Intermediate Example Int-17 (0.91 g, 1.48 mmol) in MeOH (20 mL) and THF (2 mL) in an autoclave was added 1,1'-bis(diphenylphosphino)ferrocenepalladium (II) dichloride (0.24 g, 0.30 mmol, 0.20 equiv) and triethylamine (0.23 mL, 1.63 mmol, 1.1 equiv.). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 100° C., and stirred at this temperature for 18 h. The resulting solution was concentrated under reduced pressure. The resulting material was purified using MPLC (Biotage Isolera; Snap 25 g cartridge, 100% hexane 2.0 min, gradient to 80% hexane/20% EtOAc 1.0 min, 80% hexane/20% EtOAc 3.0 min, gradient to 50% hexane/50% EtOAc 6.0 min, 50% hexane/50% EtOAc 6.5 min, gradient to 10% hexane/90% EtOAc 6.0 min, gradient to 100% EtOAc 2.7 min, 100% EtOAc 26.7 min) to give methyl 2-(4-{1-[(tert-butoxycarbonyl)amino]cyclobutyl}phenyl)-8-hydroxy-3-phenylimidazo[1,2-b]pyridazine-6-carboxylate (0.34 g, 44%):

UPLC-MS (Method 3): RT=0.89 min; m/z (rel intensity) 515 (100, (M+H)⁺); ES− m/z (rel intensity) 513 (100, (M−H)⁻).

Intermediate Example Int-19

Methyl 2-(4-{1-[(tert-butoxycarbonyl)amino]cyclobutyl}phenyl)-8-ethoxy-3-phenylimidazo[1,2-b]pyridazine-6-carboxylate

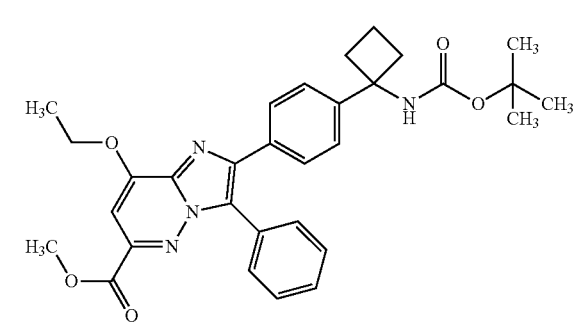 [SMILES: CCOc1cc(C(=O)OC)nn2c(-c3ccccc3)c(-c3ccc(C4(NC(=O)OC(C)(C)C)CCC4)cc3)nc12]

A mixture of methyl 2-(4-{1-[(tert-butoxycarbonyl)amino]cyclobutyl}phenyl)-8-hydroxy-3-phenylimidazo[1,2-b]pyridazine-6-carboxylate that was in a manner analgous to that described for Intermediate Example Int-18 (0.16 g, 0.32 mmol), ethyl iodide (0.50 mL, 0.63 mmol, 2.0 equiv.) and cesuim carbonate (0.31 g, 0.94 mmol, 3.0 equiv.) in DMF (6 mL) was stirred for 1 h at room temperature, followed by 3 h at 50° C. The reaction mixture was then added to ice water (20 mL). The aqueous mixture was extracted with a 4:1 DCM/isopropanol solution (2×25 mL). The combined organic phases were dried (Na₂SO₄ anh.) and concentrated under reduced pressure. The resulting material was purified using MPLC (Biotage Isolera; Snap 10 g cartridge, 80% hexane/20% EtOAc 3.0 min, gradient to 55% hexane/45% EtOAc 2.0 min, 55%/45% EtOAc 3.0 min, gradient to 4% hexane/96% EtOAc 5.5 min, gradient to 100% EtOAc 0.5 min, 100% EtOAc 7.2 min) to give methyl 2-(4-{1-[(tert-butoxycarbonyl)amino]cyclobutyl}phenyl)-8-ethoxy-3-phenylimidazo[1,2-b]pyridazine-6-carboxylate (0.072 g, 42%):

UPLC-MS (Method 3): RT=1.50 min; m/z (rel intensity) 543 (100, (M+H)⁺); ES– m/z (rel intensity) 541 (10, (M–H)⁻).

The following examples were prepared in a manner analogous to Intermediate Example Int-19 by reacting the appropriate phenol with 2-methoxyethyl bromide mL). The combined organics were dried (Na₂SO₄ anh.) and concentrated under reduced pressure. The resulting material was purified using MPLC (Biotage Isolera; Snap 25 g cartridge, 100% hexane 2.0 min, gradient to 50% hexane/ 20% EtOAc 3.5 min, 50% hexane/50% EtOAc 4.5 min, gradient to 100% EtOAc 5.0 min, 100% EtOAc 8.7 min) to give tert-butyl (1-{4-[6-chloro-8-(1H-imidazol-2-yl)-3-phenylimidazo[1,2-b]pyridazin-2-yl]phenyl}cyclobutyl)carbamate (0.28 g, 37%):

| Intermediate Example | Structure/Name | Characterization |
| --- | --- | --- |
| Int-19.1 | 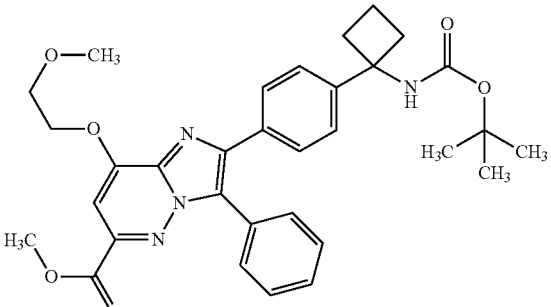<br>Methyl 2-(4-{1-[(tert-butoxycarbonyl)amino]cyclobutyl}phenyl)-8-(2-methoxyethoxy)-3-phenylimidazo[1,2-b]pyridazine-6-carboxylate | UPLC-MS (Method 3): RT = 1.48 min; m/z (rel intensity) 573 (100, (M + H)⁺); ES– m/z (rel intensity) 571 (20, (M – H)⁻). |

Intermediate Example Int-20 tert-Butyl (1-{4-[6-chloro-8-(1H-imidazol-2-yl)-3-phenylimidazo[1,2-b]-pyridazin-2-yl]phenyl}cyclobutyl)carbamate

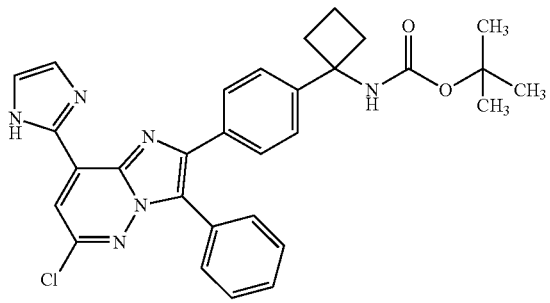 [SMILES: CC(C)(C)OC(=O)NC1(c2ccc(-c3nc4c(-c5ncc[nH]5)cc(Cl)nn4c3-c3ccccc3)cc2)CCC1]

A mixture of tert-butyl {1-[4-(8-bromo-6-chloro-3-phenylimidazo[1,2-b]pyridazin-2-yl)phenyl]cyclobutyl}carbamate that was prepared in a manner analogous to that described for Intermediate Example Int-7.1 (0.78 g, 1.42 mmol), 1H-imidazol-2-ylboronic acid (0.024 g, 2.13 mmol, 1.5 equiv.), 1,1'-bis(diphenylphosphino)ferrocenepalladium(II) dichloride CDM complex (0.12 g, 0.14 mmol, 0.1 equiv.) and cesium fluoride (0.65 g, 4.25 mmol, 3.0 equiv.) in dimethoxymethane (12 mL) was bubbled with Ar, then placed under an argon atmosphere in a sealed vial, and was heated at 100° C. for 3 days. The reaction mixture was then added to ice water (50 mL). The aqueous mixture was extracted with a 4:1 DCM/isopropanol solution (4×50

UPLC-MS (Method 3): RT=1.54 min; m/z (rel intensity) 541 (100, (M+H)⁺); ES– m/z (rel intensity) 539 (30, (M–H)⁻).

1H-NMR (d6-DMSO): δ 1.00-1.37 (br m, 9H), 1.68-1.80 (br s, 1H), 1.88-2.00 (br m, 1H), 2.27-2.39 (m, 4H), 7.27 (app q, J=0.8 Hz, 1H), 7.33 (d, J=8.6 Hz, 2H), 7.50-7.55 (m, 5H), 7.59 (d, J=8.6 Hz, 2H), 7.92 (s, 1H), 8.81 (app t, J=1.4 Hz, 1H), 9.28-9.29 (m, 1H).

Intermediate Example Int-21 tert-Butyl {1-[4-(6-carbamoyl-8-methoxy-3-phenylimidazo[1,2-b]pyridazin-2-yl)phenyl] cyclobutyl}carbamate (Approach 2)

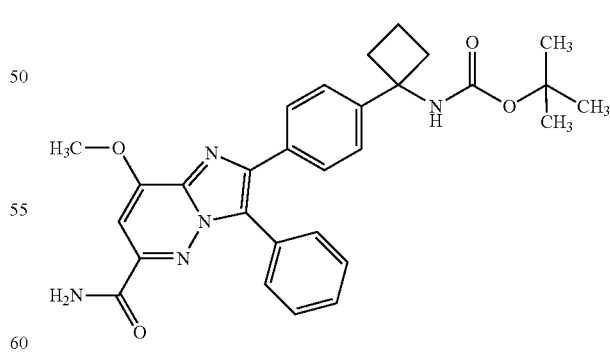

To a solution of tert-butyl {1-[4-(6-chloro-8-methoxy-3-phenylimidazo[1,2-b]pyridazin-2-yl)phenyl] cyclobutyl}carbamate that was prepared in a manner analogous to that described for Intermediate Example Int-7.3 (0.54 g, 1.00 mmol) in a solution of ammonia in MeOH (7N; 5.7 mL, 40 mmol, 40 equiv.) in an autoclave was added 1,1'-bis(diphenylphosphino)ferrocenepalladium(II) dichloride DCM complex (0.16 g, 0.20 mmol, 0.20 equiv). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 100° C., and stirred at this temperature for 18 h. The resulting material was filtered and concentrated under reduced pressure to give tert-butyl {1-[4-(6-carbamoyl-8-methoxy-3-phenylimidazo[1,2-b]pyridazin-2-yl)phenyl]cyclobutyl}carbamate (0.29 g, 57%):

UPLC-MS (Method 3): RT=1.29 min; m/z (rel intensity) 514 (70, (M+H)$^+$); ES− m/z (rel intensity) 512 (100, (M−H)$^-$).

Intermediate Example Int-22

Methyl 2-(4-{1-[(tert-butoxycarbonyl)amino]cyclobutyl}phenyl)-3-phenylimidazo[1,2-b]pyridazine-8-carboxylate

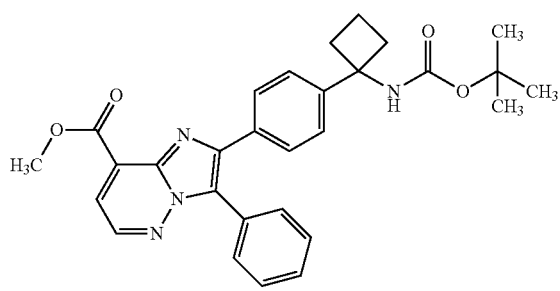 [SMILES: COC(=O)c1ccnn2c(-c3ccccc3)c(-c3ccc(C4(NC(=O)OC(C)(C)C)CCC4)cc3)nc12]

To a solution of 2-(4-{1-[(tert-butoxycarbonyl)amino]cyclobutyl}phenyl)-3-phenylimidazo[1,2-b]pyridazin-8-yl trifluoromethanesulfonate that was prepared in a manner analogous to that described for Intermediate Example Int-15 (0.15 g, 0.25 mmol) in MeOH (0.4 mL) and THF (0.04 mL) in an autoclave was added 1,1'-bis(diphenylphosphino)ferrocenepalladium(II) dichloride (0.040 g, 0.050 mmol, 0.20 equiv) and triethylamine (0.040 mL, 0.27 mmol, 1.1 equiv.). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 100° C., and stirred at this temperature for 18 h. The resulting solution was concentrated under reduced pressure. The resulting material was purified using MPLC (Biotage Isolera; Snap 10 g cartridge, 100% hexane 2.0 min, gradient to 80% hexane/20% EtOAc 2.5 min, gradient to 70% hexane/30% EtOAc 3.0 min, 70% hexane/30% EtOAc 2.5 min, gradient to 50% hexane/50% EtOAc 3.5 min, 50% hexane/50% EtOAc 4.0 min, gradient to 100% EtOAc 1.0 min, 100% EtOAc 5.8 min) to give methyl 2-(4-{1-[(tert-butoxycarbonyl)amino]cyclobutyl}phenyl)-3-phenylimidazo[1,2-b]pyridazine-8-carboxylate (0.081 g, 63%):

UPLC-MS (Method 3): RT=1.46 min; m/z (rel intensity) 499 (100, (M+H)$^+$), 997 (70, (2M+H)$^+$); ES− m/z (rel intensity) 497 (20, (M−H)$^-$).

1H-NMR (d6-DMSO): δ 1.00-1.36 (br m, 9H), 1.65-1.81 (br s, 1H), 1.86-2.02 (br m, 1H), 2.26-2.38 (m, 4H), 3.98 (s, 3H), 7.31 (d, J=8.5 Hz, 2H), 7.46-7.58 (m, 8H), 7.64 (d, J=4.5 Hz, 1H), 8.58 (d, J=4.7 Hz, 1H).

Intermediate Example Int-23

Dimethyl 2-(4-{1-[(tert-butoxycarbonyl)amino]cyclobutyl}phenyl)-3-phenylimidazo[1,2-b]pyridazine-6,8-dicarboxylate

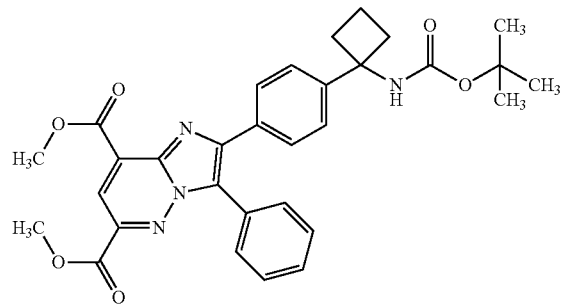 [SMILES: COC(=O)c1cc(C(=O)OC)c2nc(-c3ccc(C4(NC(=O)OC(C)(C)C)CCC4)cc3)c(-c3ccccc3)n2n1]

To a solution of tert-butyl (1-{4-[3-phenyl-6,8-dibromoimidazo[1,2-b]pyridazin-2-yl]phenyl}cyclobutyl)carbamate that was prepared in a manner analgous to that described for Intermediate Example Int-6 (0.51 g, 0.80 mmol) in MeOH (1.3 mL) and THF (0.13 mL) in an autoclave was added 1,1'-bis(diphenylphosphino)ferrocenepalladium(II) dichloride (0.13 g, 0.16 mmol, 0.20 equiv) and triethylamine (0.12 mL, 0.88 mmol, 1.1 equiv.). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 100° C., and stirred at this temperature for 18 h. The resulting solution was concentrated under reduced pressure. The resulting material was filtered and concentrated under reduced pressure to give dimethyl 2-(4-{1-[(tert-butoxycarbonyl)amino]cyclobutyl}phenyl)-3-phenylimidazo[1,2-b]pyridazine-6,8-dicarboxylate (0.45 g, 100%), which was used without further purification:

UPLC-MS (Method 3): RT=1.46 min; m/z (rel intensity) 557 (100, (M+H)$^+$).

Intermediate Example Int-24 tert-Butyl {1-[4-(6,8-dicarbamoyl-3-phenylimidazo[1,2-b]pyridazin-2-yl)-phenyl]cyclobutyl}carbamate (1) and 2-[4-(1-Aminocyclobutyl)phenyl]-3-phenylimidazo[1,2-b]pyridazine-6,8-dicarboxamide (2, Approach 1)

(1)

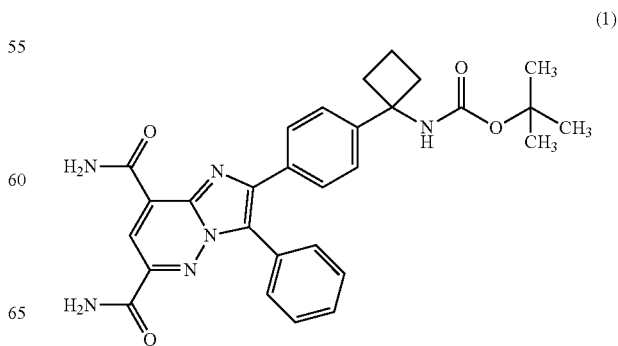

-continued (2)

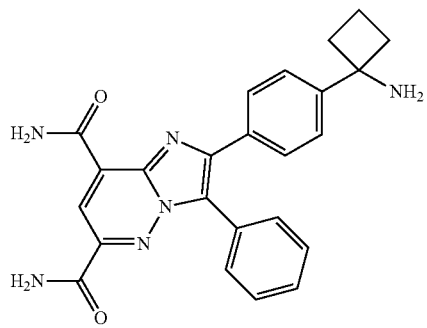

A solution of dimethyl 2-(4-{1-[(tert-butoxycarbonyl)amino]cyclobutyl}phenyl)-3-phenylimidazo[1,2-b]pyridazine-6,8-dicarboxylate that was prepared in a manner analgous to that described for Intermediate Example Int-23 (0.45 g, 0.81 mmol) in a solution of ammonia in MeOH (7N, 11.5 mL) was irradiated in a microwave apparatus at 130° C. for 90 min. The resulting mixture was concentrated under reduced pressure. The resulting material was purified using MPLC (Biotage Isolera; Snap 25 g cartridge, 100% DCM 4.5 min, gradient to 95% DCM/5% MeOH 1.0 min, 95% DCM/5% MeOH 5.0 min, gradient to 90% DCM/10% MeOH 1.0 min, 90% DCM/10% MeOH 8.1 min, gradient to 80% DCM/20% MeOH 2.0 min, 80% DCM/20% MeOH 8.2 min) to give tert-butyl {1-[4-(6,8-dicarbamoyl-3-phenylimidazo[1,2-b]pyridazin-2-yl)phenyl]cyclobutyl}carbamate (0.34 g, 8%) followed by 2-[4-(1-aminocyclobutyl)phenyl]-3-phenylimidazo[1,2-b]pyridazine-6,8-dicarboxamide (0.63 g, 18%).

tert-Butyl {1-[4-(6,8-dicarbamoyl-3-phenylimidazo[1,2-b]pyridazin-2-yl)phenyl]cyclobutyl}carbamate (1)

UPLC-MS (Method 3): RT=1.28 min; m/z (rel intensity) 527 (100, (M+H)$^+$); ES– m/z (rel intensity) 525 (60, (M–H)$^-$).

2-[4-(1-Aminocyclobutyl)phenyl]-3-phenylimidazo[1,2-b]pyridazine-6,8-dicarboxamide UPLC-MS (Method 3): RT=1.02 min; m/z (rel intensity) 410 (100 (M+H-17)$^+$), 427 (70, (M+H)$^+$), 853 (20, (2M+H)$^+$); ES– m/z (rel intensity) 425 (100, (M–H)$^-$), 851 (10, (M–H)$^-$).

Intermediate Example Int-25 tert-Butyl {1-[4-(6-acetamido-3-phenylimidazo[1,2-b]pyridazin-2-yl)-phenyl]cyclobutyl}carbamate

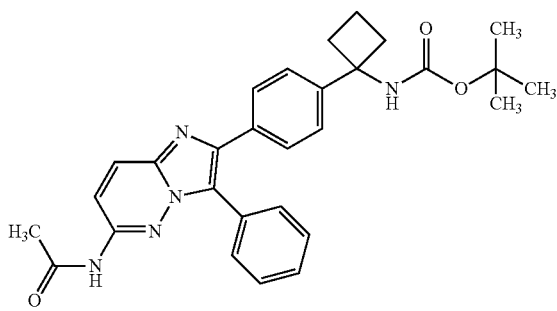 [SMILES: CC(=O)Nc1ccc2nc(-c3ccc(C4(NC(=O)OC(C)(C)C)CCC4)cc3)c(-c3ccccc3)n2n1]

To a solution of tert-butyl {1-[4-(6-amino-3-phenylimidazo[1,2-b]pyridazin-2-yl)phenyl]cyclobutyl}carbamate that was prepared in a manner analgous to that described for Intermediate Example Int-6.3 (0.10 g, 0.22 mmol) in DCM (4 mL) was added pyridine (0.036 mL, 0.44 mmol, 2 equiv) and acetic anhydride (0.027 mL, 0.29 mmol, 1.3 equiv). The reaction mixture was stirred for 24 h at room temperature, additional acetic anhydride (0.042 mL, 0.44 mmol, 2.0 equiv) was added and the reaction mixture was stirred at room temperature for an additional 24 h. The resulting mixture was concentrated under reduced pressure to give tert-butyl {1-[4-(6-acetamido-3-phenylimidazo[1,2-b]pyridazin-2-yl)phenyl]cyclobutyl}carbamate (0.11 g, 100%) which was used without further purification:

UPLC-MS (Method 3): RT=1.34 min; m/z (rel intensity) 498 (100, (M+H)$^+$), 995 (60, (M+H)$^+$); ES– m/z (rel intensity) 496 (50, (M–H)$^-$), 993 (10, (2M–H)$^-$).

The following examples were prepared in a manner analogous to Intermediate Example Int-25 by reacting tert-butyl {1-[4-(6-amino-3-phenylimidazo[1,2-b]pyridazin-2-yl)phenyl]cyclobutyl}carbamate (Intermediate Example Int-6.3) or tert-butyl {1-[4-(8-amino-3-phenylimidazo[1,2-b]pyridazin-2-yl)phenyl]cyclobutyl}carbamate (Intermediate Example Int-6.6) with the appropriate anhydride

| Intermediate Example | Structure/Name | Characterization |
| --- | --- | --- |
| Int-25.1 | ![structure] tert-Butyl [1-(4-{3-phenyl-6-[(trifluoroacetyl)amino]imidazo[1,2-b]pyridazin-2-yl}phenyl)cyclobutyl]carbamate | This material was used without characterization. |

| Intermediate Example | Structure/Name | Characterization |
|---|---|---|
| Int-25.2 | tert-Butyl [1-(4-{6-[(methylsulfonyl)amino]-3-phenylimidazo[1,2-b]pyridazin-2-yl}phenyl)cyclobutyl]carbamate | This material was used without characterization. |
| Int-25.3 | tert-Butyl {1-[4-(8-acetamido-3-phenylimidazo[1,2-b]pyridazin-2-yl)phenyl]cyclobutyl}carbamate | UPLC-MS (Method 3): RT = 1.47 min; m/z (rel intensity) 498 (90, (M + H)$^+$), 995 (20, (M + H)$^+$); ES-m/z (rel intensity) 496 (90, (M − H)$^-$). |

Intermediate Example Int-26 tert-Butyl (1-{4-[6-(methylsulfonyl)-3-phenylimidazo[1,2-b]pyridazin-2-yl]-phenyl}cyclobutyl)carbamate

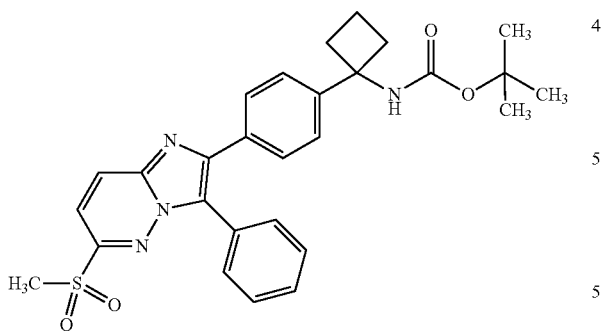

To a solution of tert-butyl (1-{4-[6-(methylsulfanyl)-3-phenylimidazo[1,2-b]pyridazin-2-yl]phenyl}cyclobutyl) carbamate that was prepared in a manner analgous to that described for Intermediate Example Int-6.4 (0.10 g, 0.21 mmol) in chloroform (4 mL) was added meta-chloroperoxybenzoic acid (70% pure, 0.10 g, 0.42 mmol, 2.0 equiv) portionwise. The resulting mixture was stirred at room temperature for 12 h, then was diluted with DCM (10 mL). The resulting mixture was washed with an aqueous NaOH solution (2N, 10 mL), dried (Na$_2$SO$_4$ anh.) and concentrated under reduced pressure to give tert-butyl (1-{4-[6-(methylsulfonyl)-3-phenylimidazo[1,2-b]pyridazin-2-yl]phenyl}cyclobutyl)carbamate (0.12 g, 100%) which was used without further purification:

UPLC-MS (Method 3): RT=1.38 min; m/z (rel intensity) 519 (100, (M+H)$^+$); ES− m/z (rel intensity) 517 (10, (M−H)$^-$).

Intermediate Example Int-27

2-(4-{1-[(tert-Butoxycarbonyl)amino]cyclobutyl}phenyl)-3-phenylimidazo[1,2-b]pyridazine-6-carboxylic acid

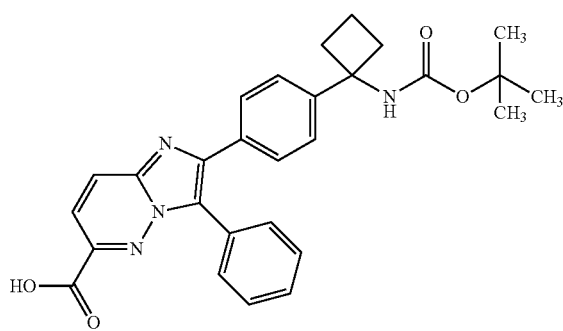 [SMILES: CC(C)(C)OC(=O)NC1(c2ccc(-c3nc4ccc(C(=O)O)nn4c3-c3ccccc3)cc2)CCC1]

To a solution of ethyl 2-(4-{1-[(tert-butoxycarbonyl)amino]cyclobutyl}phenyl)-3-phenylimidazo[1,2-b]pyridazine-6-carboxylate that was prepared in a manner analgous to that described for Intermediate Example Int-4 (2.00 g, 3.90 mmol) in MeOH (50 mL) was added an aqueous NaOH solution (10%, 10 mL). The resulting mixture was stirred at room temperature for 24 h, then was diluted with water (100 mL). The resulting mixture was adjusted to pH 4 using an aqueous HCl solution (2N). The resulting crystals were collected, washed with water, and dried at 40° C. to give 2-(4-{1-[(tert-butoxycarbonyl)amino]cyclobutyl}phenyl)-3-phenylimidazo[1,2-b]pyridazine-6-carboxylic acid (1.50 g, 79%) which was used without further purification:

UPLC-MS (Method 3): RT=0.77 min; m/z (rel intensity) 485 (100, (M+H)$^+$), 969 (40, (2M+H)$^+$); ES– m/z (rel intensity) 439 (60 (M–CO2H)$^-$), 483 (100, (M–H)$^-$), 967 (20, (M–H)$^-$).

Intermediate Example Int-28

Methyl 2-(4-{1-[(tert-butoxycarbonyl)amino]cyclobutyl}phenyl)-3-phenylimidazo[1,2-b]pyridazine-6-carboxylate

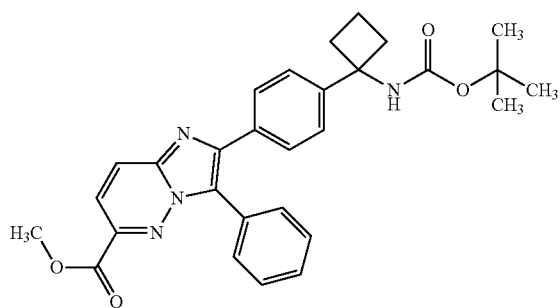 [SMILES: COC(=O)c1ccc2nc(-c3ccc(C4(NC(=O)OC(C)(C)C)CCC4)cc3)c(-c3ccccc3)n2n1]

A mixture of 2-(4-{1-[(tert-butoxycarbonyl)amino]cyclobutyl}phenyl)-3-phenylimidazo[1,2-b]pyridazine-6-carboxylic acid that was prepared in a manner analgous to that described for Intermediate Example Int-27 (0.075 g, 0.16 mmol), cesium carbonate (0.15 g, 0.46 mmol, 3.0 equiv) and methyl iodide (0.020 mL, 0.31 mmol, 2.0 equiv) in DMF (2 mL) was stirred at room temperature for 2 days, after which additional methyl iodide (0.020 mL, 0.31 mmol, 2.0 equiv) was added and the mixture was heated at 50° C. for 3 h. The resulting mixture was treated with water (25 mL). The aqueous mixture was extracted with EtOAc (3×10 mL). The combined organics were dried (Na$_2$SO$_4$ anh) and concentrated under reduced pressure to give methyl 2-(4-{1-[(tert-butoxycarbonyl)amino]cyclobutyl}phenyl)-3-phenylimidazo[1,2-b]pyridazine-6-carboxylate (0.087 g, 113%) which was used without further purification:

UPLC-MS (Method 3): RT=1.46 min; m/z (rel intensity) 499 (100, (M+H)$^+$), 997 (60, (2M+H)).

Intermediate Example Int-29 tert-Butyl (1-{4-[6,8-bis(4-fluorophenyl)-3-phenylimidazo[1,2-b]pyridazin-2-yl]phenyl}cyclobutyl)carbamate

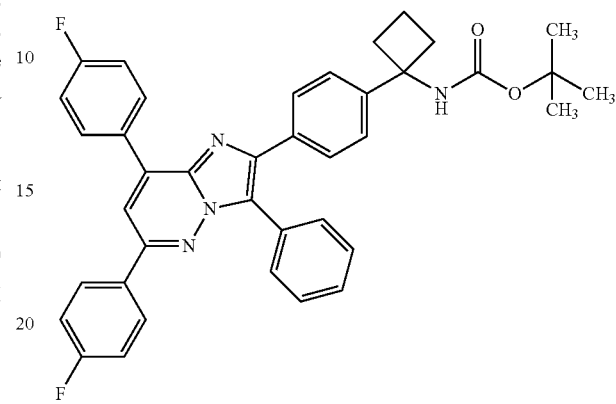

A mixture of tert-butyl (1-{4-[3-phenyl-6,8-dibromoimidazo[1,2-b]pyridazin-2-yl]phenyl}cyclobutyl)carbamate that was prepared in a manner analgous to that described for Intermediate Example Int-6 (0.25 g, 0.42 mmol), (4-fluorophenyl)boronic acid (0.12 g, 0.84 mmol, 2.0 equiv.), 1,1'-bis(diphenylphosphino)ferrocenepalladium(II) dichloride (0.034 g, 0.042 mmol, 0.1 equiv.) and sodium carbonate (0.13 g, 1.25 mmol, 3.0 equiv) in a mixture of water (0.6 mL) and dioxane (4.5 mL) was irradiated in a microwave apparatus at 110° C. for 60 min. The resulting reaction mixture was added to water (25 mL). The aqueous mixture was extracted with DCM (3×25 mL). The combined organic phases were washed with an aqueous NaOH solution (2N), dried (Na$_2$SO$_4$ anh.) and concentrated under reduced pressure to give impure tert-butyl (1-{4-[6,8-bis(4-fluorophenyl)-3-phenylimidazo[1,2-b]pyridazin-2-yl]phenyl}cyclobutyl)carbamate (0.39 g) which was used without further purification:

UPLC-MS (Method 3): RT=1.84 min; m/z (rel intensity) 629 (100, (M+H)$^+$); ES– m/z (rel intensity) 673 (100, (M–H+HCO$_2$H)$^-$).

Intermediate Example Int-30 tert-Butyl {1-[4-(6-{4-[methoxy(methyl)carbamoyl]phenyl}-3-phenylimidazo[1,2-b]pyridazin-2-yl)phenyl]cyclobutyl}carbamate

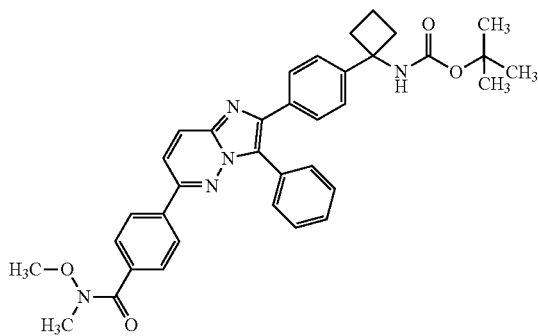 [SMILES: CON(C)C(=O)c1ccc(-c2ccc3nc(-c4ccc(C5(NC(=O)OC(C)(C)C)CCC5)cc4)c(-c4ccccc4)n3n2)cc1]

A mixture of 2-(4-{1-[(tert-butoxycarbonyl)amino]cyclobutyl}phenyl)-3-phenylimidazo[1,2-b]pyridazine-6-carboxylic acid that was prepared in a manner analgous to that described for Intermediate Example Int-27 (0.40 g, 0.82 mmol), O,N-dimethylhydroxylamine hydrochloride (0.12 g, 1.24 mmol, 1.5 equiv), PYBOP (0.54 g, 1.03 mmol, 1.25 equiv) and N,N-diisopropylethylamine (0.9 mL, 4.95 mmol, 6.0 equiv) in DMF (15 mL) was stirred at room temperature for 21 h. The resulting mixture was added to ice water (50 mL). The aqueous mixture was extracted with EtOAc (4×25 mL). The combined organic phases were sequentially washed with water (25 mL) and a saturated aqueous NaCl solution (25 mL), dried (Na$_2$SO$_4$ anh.) and concentrated under reduced pressure. The resulting brown oil (1.48 g) was purified using MPLC (Biotage Isolera; Snap 25 g cartridge, 100% hexane 2.0 min, gradient to 80% hexane/20% EtOAc 1.0 min, 80% hexane/20% EtOAc 3.0 min, gradient to 50% hexane/50% EtOAc 6.0 min, 50% hexane/50% EtOAc 6.5 min, gradient to 10% hexane/90% EtOAc 6.0 min, gradient to 100% EtOAc 2.7 min, 100% EtOAc 4.5 min) to give tert-butyl {1-[4-(6-{4-[methoxy(methyl)carbamoyl]phenyl}-3-phenylimidazo[1,2-b]pyridazin-2-yl)phenyl]cyclobutyl}carbamate (0.25 g, 57%):

UPLC-MS (Method 3): RT=1.40 min; m/z (rel intensity) 528 (100, (M+H)$^+$); ES− m/z (rel intensity) 526 (10, (M−H+HCO$_2$H)$^−$).

Intermediate Example Int-31 tert-Butyl (1-{4-[6-(4-acetylphenyl)-3-phenylimidazo[1,2-b]pyridazin-2-yl]-phenyl}cyclobutyl)carbamate

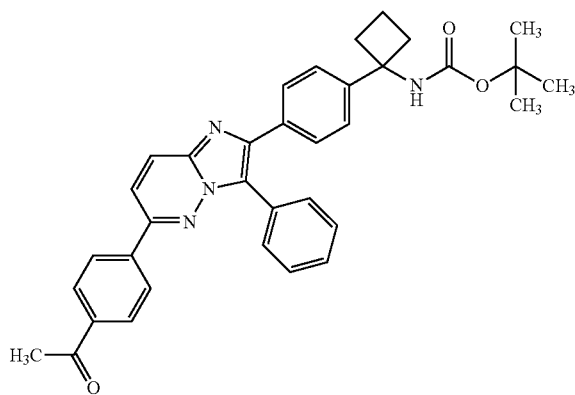 [SMILES: CC(=O)c1ccc(-c2ccc3nc(-c4ccc(C5(NC(=O)OC(C)(C)C)CCC5)cc4)c(-c4ccccc4)n3n2)cc1]

To a solution of tert-butyl {1-[4-(6-{4-[methoxy(methyl)carbamoyl]phenyl}-3-phenylimidazo[1,2-b]pyridazin-2-yl)phenyl]cyclobutyl}carbamate that was prepared in a manner analgous to that described for Intermediate Example Int-30 (0.25 g, 0.47 mmol) in THF (10 mL) at 0° C. under an argon atmosphere was added methylmagnesium chloride (3M in THF, 0.40 mL, 1.19 mmol, 2.5 equiv) portionwise through a septum. The resulting mixture was stirred at 0° C. and at room temperature for 5 h. Additional methylmagnesium chloride (3M in THF, 0.16 mL, 0.48 mmol, 1.0 equiv) was added and the resulting mixture was stirred for 12 h. The resulting mixture was added to a saturated aqueous ammonium chloride solution (25 mL). The aqueous mixture was extracted with EtOAc (3×25 mL). The combined organic phases were dried (Na$_2$SO$_4$ anh.) and concentrated under reduced pressure. The resulting yellow oil (0.23 g) was purified using MPLC (Biotage Isolera; Snap 10 g cartridge, 100% hexane 2.0 min, gradient to 50% hexane/50% EtOAc 2.0 min, 50% hexane/50% EtOAc 2.0 min, gradient to 100% EtOAc 5.0 min, 100% EtOAc 21.0 min) to give tert-butyl (1-{4-[6-(4-acetylphenyl)-3-phenylimidazo[1,2-b]pyridazin-2-yl]phenyl}cyclobutyl)carbamate (0.053 g, 23%):

UPLC-MS (Method 3): RT=1.51 min; m/z (rel intensity) 483 (100, (M+H)$^+$), 965 (80, (2M+H)$^+$); ES− m/z (rel intensity) 481 (10, (M−H)$^−$).

Intermediate Example Int-32 tert-Butyl {1-[4-(3-phenyl-8-propylimidazo[1,2-b]pyridazin-2-yl)phenyl]-cyclobutyl}carbamate

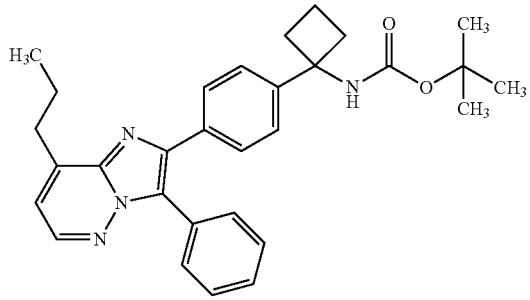 [SMILES: CCCc1ccnn2c(-c3ccccc3)c(-c3ccc(C4(NC(=O)OC(C)(C)C)CCC4)cc3)nc12]

To a mixture of tert-butyl {1-[4-(6-chloro-8-cyclopropyl-3-phenylimidazo[1,2-b]pyridazin-2-yl)phenyl]cyclobutyl}carbamate that was prepared in a manner analgous to that described for Intermediate Example Int-14.6 (0.136 g, 0.26 mmol) and 5% palladium on carbon (0.026 g) in DMF (1 mL) was added a solution of sodium formate (0.18 g, 2.6 mmol, 10.0 eq) in water (0.4 mL). The resulting mixture was stirred at 80° C. for 3 h, diluted with MeOH (10 mL) and stirred at room temperature for 1 h. The resulting solution was filtered through a membrane filter and concentrated under reduced pressure. The resulting material was purified using MPLC (Biotage Isolera; Snap 10 g cartridge, 100% hexane 2.0 min, gradient to 80% hexane/20% EtOAc 4.0 min, 80% hexane/20% EtOAc 2.5 min, gradient to 70% hexane/30% EtOAc 2.5 min, 70% hexane/30% EtOAc 9.6 min) to give tert-butyl {1-[4-(3-phenyl-8-propylimidazo[1,2-b]pyridazin-2-yl)phenyl]cyclobutyl}carbamate (0.12 g, 93%):

UPLC-MS (Method 3): RT=1.65 min; m/z (rel intensity) 483 (100, (M+H)$^+$), 965 (60, (M+H)$^+$); ES− m/z (rel intensity) 481 (10, (M−H)$^−$).

Intermediate Example Int-32 tert-Butyl {1-[4-(6-chloro-7,8-dimethyl-3-phenylimidazo[1,2-b]pyridazin-2-yl)phenyl]cyclobutyl}carbamate

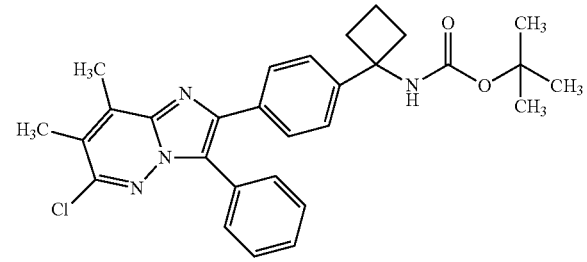 [SMILES: Cc1c(Cl)nn2c(-c3ccccc3)c(-c3ccc(C4(NC(=O)OC(C)(C)C)CCC4)cc3)nc2c1C]

A mixture of crude tert-butyl (1-{4-[bromo(phenyl)acetyl]phenyl}cyclobutyl)carbamate [that was prepared in a manner analgous to that described for Intermediate Example Int-1-A](237 mg, ~80% purity, 0.430 mmol, 1.0 eq), 6-chloro-4,5-dimethylpyridazin-3-amine (CAS-Nr. 76593-36-7, 67.2 mg, 0.430 mmol, 1.0 eq) and N,N-diisopropylethylamine (70 μL, 0.430 mmol, 1.0 eq) in butyronitrile (2.6 mL) was heated for 17 hours at 125° C. On cooling the mixture was partitioned between DCM and water, stirred vigorously and filtered through a silicone coated filter paper. The filtrate was concentrated in vacuo. The crude mixture was purified via MPLC (Biotage Isolera; 25 g SNAP cartridge: hexane/EtOAc 9/1→hexane/EtOAc 3/2) to give 185 mg (78% yield) of the title compound.

UPLC-MS (Method 2): RT=1.68 min; m/z=504 (M+H)⁺.

Intermediate Example Int-33

Methyl 6-amino-4,5-dimethylpyridazine-3-carboxylate

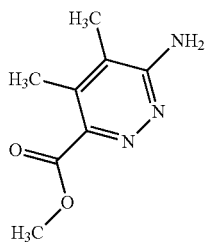

A mixture of 6-chloro-4,5-dimethylpyridazin-3-amine (CAS-Nr.76593-36-7, 1.00 g, 6.35 mmol, 1.0 eq), [1,1,-bis-(diphenylphosphino)ferrocene]-palladium(II) dichloride (1.04 g, 1.27 mmol, 0.2 eq) and triethylamine (973 μL, 6.98 mmol, 1.1 eq) was placed in 90 mL autoclave and dissolved in 11.3 mL MeOH/THF (10/1).

The autoclave was flushed with carbon monoxide (3×) and was then pressurized with carbon monoxide to 9 bar. The reaction mixture was stirred for 30 min at RT. The carbon monoxide was released and the autoclave was then degassed by the use of high vacuum. The autoclave was again pressurized to 9 bar with carbon monoxide and subsequently heated to 100° C. In the course of the reaction, carbon monoxide consumption was observed (decrease of CO pressure). The autoclave was cooled to rt, and after release of carbon monoxide flushed with inert gas. The reaction mixture was filtered through a small pad of Celite. The crude mixture was purified via MPLC (Biotage Isolera; 50 g SNAP cartridge: DCM→DCM/ethanol 95/5) to give 1.28 g (95% yield) of the title compound in 85% purity (UPLC, area-%).

UPLC-MS (Method 2): RT=0.62 min; m/z=182 (M+H)⁺.

Intermediate Example Int-34 tert-Butyl {1-[4-(6-methoxy-7,8-dimethyl-3-phenylimidazo[1,2-b]pyridazin-2-yl)phenyl]cyclobutyl}carbamate

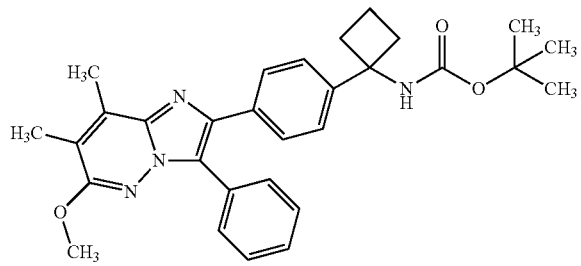 [SMILES: COc1nn2c(-c3ccccc3)c(-c3ccc(C4(NC(=O)OC(C)(C)C)CCC4)cc3)nc2c(C)c1C]

Step 1: 6-Methoxy-4,5-dimethylpyridazin-3-amine

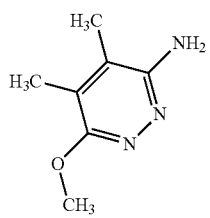

6-Chloro-4,5-dimethylpyridazin-3-amine (CAS-Nr. 76593-36-7, 500 mg, 3.17 mmol, 1.0 eq) in 14.51 mL of a 25% solution (w/w) of sodium methylate in MeOH was heated for 1 h at 130° C. in a single mode microwave oven. The reaction mixture was partitioned between DCM and water. The organic phase was washed with brine and dried (Na₂SO₄ anh.). Volatile components were removed by the use of a rotary evaporator and the crude mixture was purified via MPLC (Biotage Isolera; 25 g SNAP NH2 cartridge: hexane→hexane/EtOAc 1/1) to give 250 mg (49% yield) of the title compound.

1H-NMR (400 MHz, d6-DMSO): δ [ppm]=1.98 (s, 3H), 2.00 (s, 3H), 5.49 (s, 3H), N$\underline{H_2}$ not assigned.

Step 2: tert-Butyl {1-[4-(6-methoxy-7,8-dimethyl-3-phenylimidazo[1,2-b]-pyridazin-2-yl)phenyl]cyclobutyl}carbamate

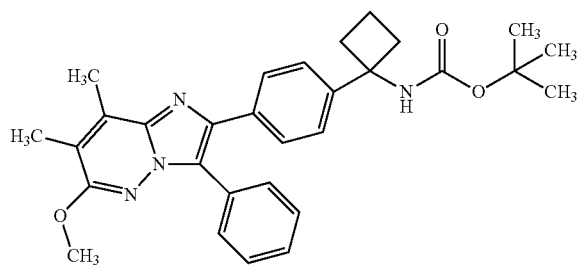

A mixture of crude tert-butyl (1-{4-[bromo(phenyl)acetyl]phenyl}cyclobutyl)carbamate [that was prepared in a manner analgous to that described for Intermediate Example Int-1-A](391 mg, ~80% purity, 0.710 mmol, 1.0 eq), 6-methoxy-4,5-dimethylpyridazin-3-amine (that was prepared in a manner analgous to that described for Intermediate Example Int-34, Step 1, 108 mg, 0.710 mmol, 1.0 eq) and N,N-diisopropylethylamine (140 μL, 0.780 mmol, 1.1 eq) in butyronitrile (4.9 mL) was heated for 3 hours at 120° C. On cooling the reaction mixture was concentrated in vacuo. The crude mixture was purified via MPLC (Biotage Isolera; 25 g SNAP cartridge: hexane/EtOAc 9/1→hexane/EtOAc 2/3) to give 105 mg (28% yield) of the title compound.

UPLC-MS (Method 2): RT=1.68 min; m/z=499 (M+H)+.

Intermediate Example Int-35 tert-Butyl (1-{4-[7,8-dimethyl-6-(methylsulfanyl)-3-phenylimidazo[1,2-b]-pyridazin-2-yl]phenyl}cyclobutyl)carbamate

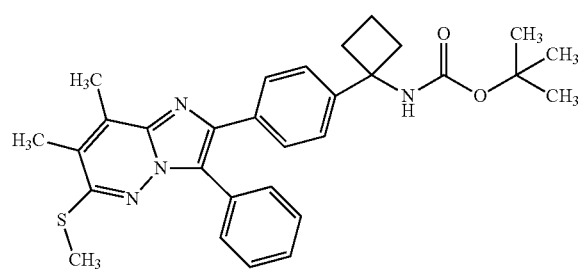 [SMILES: COc1nn2c(-c3ccccc3)c(-c3ccc(C4(NC(=O)OC(C)(C)C)CCC4)cc3)nc2c(C)c1C]

Step 1:
4,5-Dimethyl-6-(methylsulfanyl)pyridazin-3-amine

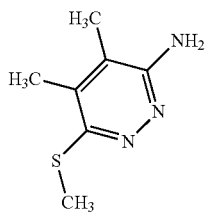

6-Chloro-4,5-dimethylpyridazin-3-amine (CAS-Nr. 76593-36-7, 400 mg, 2.54 mmol, 1.0 eq) and sodium methanethiolate (196 mg, 2.79 mmol, 1.1 eq) in 10.4 mL ethanol were heated for 1 h to 130° C. in a single mode microwave oven. The reaction mixture was partitioned between DCM and water. The organic phase was washed with brine and dried with sodium sulfate. The resulting mixture was filtered through a Whatman filter and the volatile components were removed in vacuo. The crude mixture was purified via MPLC (Biotage Isolera; 50 g SNAP cartridge: DCM/ethanol 95/5→DCM/ethanol 4/1) to give 182 mg (21% yield) of the title compound in 50% purity (UPLC, area-%).

UPLC-MS (Method 2): RT=0.76 min; m/z=170 (M+H)+.

Step 2: tert-Butyl (1-{4-[7,8-dimethyl-6-(methylsulfanyl)-3-phenylimidazo[1,2-b]pyridazin-2-yl]phenyl}cyclobutyl)carbamate

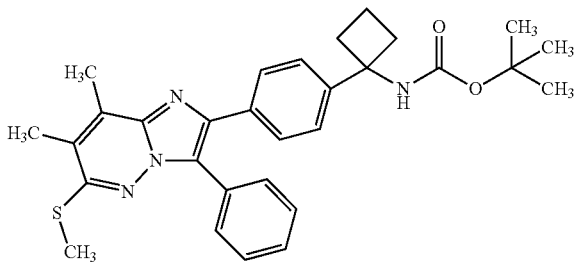 [SMILES: CSc1nn2c(-c3ccccc3)c(-c3ccc(C4(NC(=O)OC(C)(C)C)CCC4)cc3)nc2c(C)c1C]

A mixture of crude tert-butyl (1-{4-[bromo(phenyl)acetyl]phenyl}cyclobutyl)carbamate [that was prepared in a manner analgous to that described for Intermediate Example Int-1-A](540 mg, ~80% purity, 0.970 mmol, 1.0 eq), 4,5-dimethyl-6-(methylsulfanyl)-pyridazin-3-amine (that was prepared in a manner analgous to that described for Intermediate Example Int-35, Step 1, 181 mg, ~50% purity, 1.07 mmol, 1.1 eq) and N,N-diisopropylethylamine (170 μL, 0.970 mmol, 1.1 eq) in butyronitrile (4.7 mL) was heated for 4 hours at 125° C. On cooling the reaction mixture was concentrated in vacuo. The crude mixture was purified via reversed phase preparative HPLC to give 105 mg (19% yield) of the title compound.

UPLC-MS (Method 2): RT=1.74 min; m/z=516 (M+H)+.

Intermediate Example Int-36 tert-Butyl {1-[4-(6-ethoxy-7,8-dimethyl-3-phenylimidazo[1,2-b]pyridazin-2-yl)phenyl]cyclobutyl}carbamate

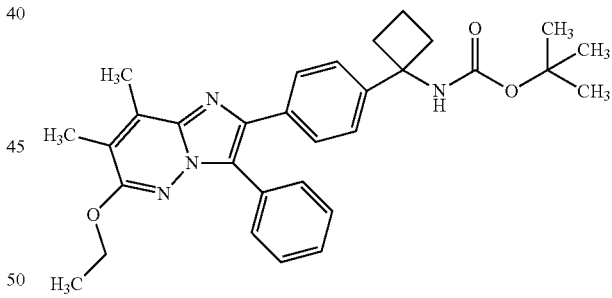

Step 1: 6-Ethoxy-4,5-dimethylpyridazin-3-amine

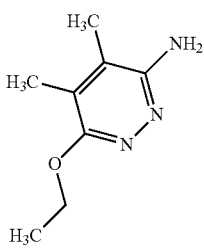

6-Chloro-4,5-dimethylpyridazin-3-amine (CAS-Nr. 76593-36-7, 500 mg, 3.17 mmol, 1.0 eq) and sodium ethanolate in ethanol (16 mL, 21 w/w-%, 53.9 mmol, 17 eq) were heated for 2 h to 130° C. in a single mode microwave oven. The reaction mixture was partitioned between DCM and water. The organic phase was washed with brine and dried with sodium sulfate. The resulting mixture was filtered through a Whatman filter and the volatile components were removed in vacuo. The crude mixture was purified via MPLC (Biotage Isolera; 28 g NH2-cartridge: hexane→hexane/EtOAc 1/1) to give 267 mg (50% yield) of the title compound.

UPLC-MS (Method 2): RT=0.78 min; m/z=168 (M+H)⁺.

Step 2: tert-Butyl {1-[4-(6-ethoxy-7,8-dimethyl-3-phenylimidazo[1,2-b]-pyridazin-2-yl)phenyl]cyclobutyl}carbamate

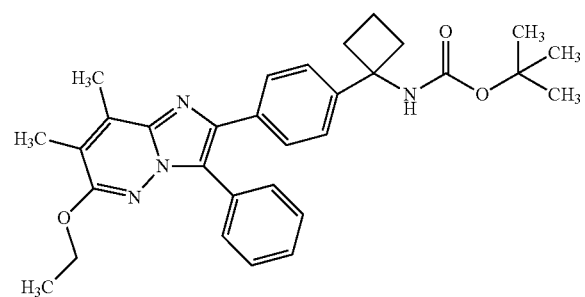 [SMILES: CCOc1nn2c(-c3ccccc3)c(-c3ccc(C4(NC(=O)OC(C)(C)C)CCC4)cc3)nc2c(C)c1C]

A mixture of crude tert-butyl (1-{4-[bromo(phenyl)acetyl]phenyl}cyclobutyl)carbamate [that was prepared in a manner analgous to that described for Intermediate Example Int-1-A](300 mg, ~80% purity, 0.540 mmol, 1.0 eq), 6-ethoxy-4,5-dimethylpyridazin-3-amine (that was prepared in a manner analgous to that described for Intermediate Example Int-36, Step 1, 124 mg, ~80% purity, 0,590 mmol, 1.1 eq) and N,N-diisopropylethylamine (100 µL, 0.590 mmol, 1.1 eq) in butyronitrile (3.3 mL) was heated for 3.5 hours at 125° C. On cooling the reaction mixture was concentrated in vacuo. The crude mixture was purified via preparative MPLC (Biotage Isolera; 50 g SNAP-cartridge: hexane/EtOAc 9/1→hexane/EtOAc 1/1) to give 220 mg (70% yield) of the title compound.

UPLC-MS (Method 2): RT=1.74 min; m/z=514 (M+H)⁺.

Example 1

1-[4-(6-Methyl-3-phenylimidazo[1,2-b]pyridazin-2-yl)phenyl]cyclobutanamine

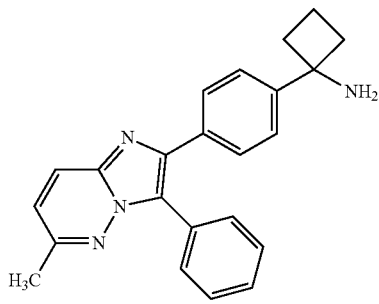

To a mixture of tert-butyl {1-[4-(6-methyl-3-phenylimidazo[1,2-b]pyridazin-2-yl)phenyl]-cyclobutyl}carbamate that was prepared in a manner analgous to that described for Intermediate Example Int-1 (200 mg, 0.440 mmol, 1.0 eq) in DCM (2.2 mL) and methanol (1.8 mL) was added a solution of 4M hydrogen chloride in dioxane (2.2 mL, 8.80 mmol, 20.0 eq) and the mixture was stirred for overnight at rt. The mixture was poured onto ice, made alkaline with aqueous sodium hydroxide (2N) and extracted with DCM. The combined organic phases were washed with brine, dried and concentrated in vacuo. Purification was achieved by crystallization from diisopropyl ether. The resulting solid was filtered and dried under high vacuum overnight to give 130 mg (83% yield) of the title compound.

UPLC-MS (Method 2): RT=1.20 min; m/z=355.68 (M+H).

1H-NMR (400 MHz, MeOD): δ [ppm]=1.96 (m, 1H), 2.24 (m, 1H), 2.54-2.64 (m, 2H), 2.67 (s, 3H), 2.70-2.84 (m, 2H), 7.49-7.65 (m, 7H), 7.66-7.71 (m, 2H), 7.80 (d, 1H), 8.32 (d, 1H), NH₂ not assigned.

Example 2

1-[4-(6-Ethyl-3-phenylimidazo[1,2-b]pyridazin-2-yl)phenyl]cyclobutanamine

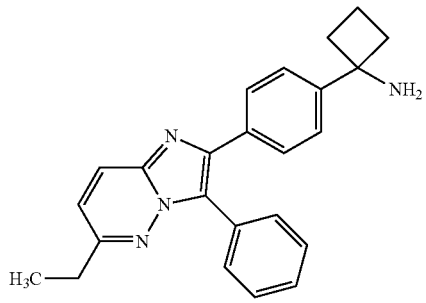 [SMILES: CCc1ccc2nc(-c3ccc(C4(N)CCC4)cc3)c(-c3ccccc3)n2n1]

To a mixture of tert-butyl {1-[4-(6-ethyl-3-phenylimidazo[1,2-b]pyridazin-2-yl)phenyl]cyclobutyl}carbamate that was prepared in a manner analgous to that described for Intermediate Example Int-2 (300 mg, 0.608 mmol, 1.0 eq) in DCM (3.9 mL) and MeOH (2.5 mL) was added a solution of 4M hydrogen chloride in dioxane (3.0 mL, 12.2 mmol, 20.0 eq) and the mixture was stirred for overnight at rt. The mixture was poured onto ice, made alkaline with aqueous sodium hydroxide (2N) and extracted with DCM. The combined organic phases were washed with brine, dried and concentrated in vacuo. Purification was achieved by crystallization from diisopropyl ether. The resulting solid was filtered and dried under high vacuum overnight to give 119 mg (52% yield) of the title compound.

UPLC-MS (Method 4): RT=1.37 min; m/z=369.29 (M+H).

1H-NMR (400 MHz, d6-DMSO): δ [ppm]=1.18 (t, 3H), 1.59 (m, 1H), 1.82-2.20 (m, 5H), 2.25-2.39 (m, 2H), 2.73 (q, 2H), 7.20 (d, 1H), 7.31-7.38 (m, 2H), 7.39-7.56 (m, 7H), 8.06 (d, 1H).

Example 3

1-{4-[3-Phenyl-6-(trifluoromethyl)imidazo[1,2-b]pyridazin-2-yl]phenyl}-cyclobutanamine

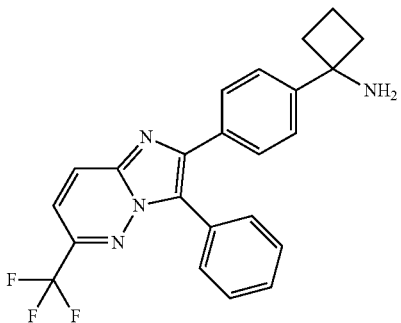 [SMILES: NC1(c2ccc(-c3nc4ccc(C(F)(F)F)nn4c3-c3ccccc3)cc2)CCC1]

To a mixture of tert-butyl (1-{4-[3-phenyl-6-(trifluoromethyl)imidazo[1,2-b]pyridazin-2-yl]phenyl}cyclobutyl)carbamate that was prepared in a manner analogous to that described for Intermediate Example Int-3 (680 mg, 1.177 mmol, 1.0 eq) in DCM (7.6 mL) and methanol (4.8 mL) was added a solution of 4M hydrogen chloride in dioxane (5.9 mL, 23.5 mmol, 20.0 eq) and the mixture was stirred for overnight at rt. The mixture was poured onto ice, made alkaline with aqueous sodium hydroxide (2N) and extracted with EtOAc (3×). The combined organic phases were washed with brine, dried and concentrated in vacuo. Purification was achieved by crystallization from diisopropyl ether. The resulting solid was filtered and dried under high vacuum overnight to give 440 mg (92% yield) of the title compound.

UPLC-MS (Method 4): RT=1.40 min; m/z=393.58 (M−NH$_2$)$^+$.

1H-NMR (400 MHz, d6-DMSO): δ [ppm]=1.60 (m, 1H), 1.85-2.25 (m, 5H), 2.27-2.39 (m, 2H), 7.40 (d, 2H), 7.45-7.61 (m, 7H), 7.67 (d, 1H), 8.46 (d, 1H).

Example 4

Ethyl 2-[4-(1-aminocyclobutyl)phenyl]-3-phenylimidazo[1,2-b]pyridazine-6-carboxylate

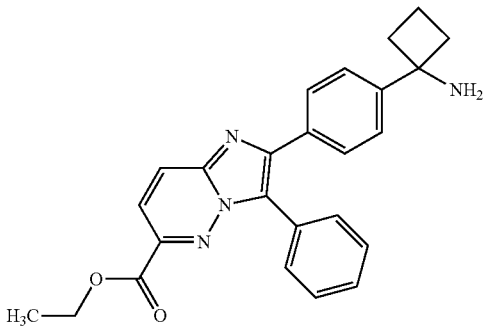 [SMILES: CCOC(=O)c1ccc2nc(-c3ccc(C4(N)CCC4)cc3)c(-c3ccccc3)n2n1]

To a mixture of ethyl 2-(4-{1-[(tert-butoxycarbonyl)amino]cyclobutyl}phenyl)-3-phenylimidazo[1,2-b]pyridazine-6-carboxylate that was prepared in a manner analogous to that described for Intermediate Example Int-4 (0.96 g, 1.87 mmol) in DCM (12.0 mL) and methanol (7.6 mL) was added a solution of 4M hydrochloric acid in dioxane (9.4 mL) and the mixture was stirred for 2 hours at rt. The mixture was poured onto ice, made alkaline with aqueous sodium hydroxide (2N) and extracted with DCM. The combined organic phases were washed with brine, dried and concentrated in vacuo. The reaction was repeated using 2.5 g of the carbamate and the crude product from both reactions were combined. Purification was achieved by chromatography on silica (gradient elution: 95:5 DCM:ethanol to 8:2 DCM:ethanol) to give two fractions of the title compound (0.8 g, 88% purity & 1.6 g, 93% purity).

UPLC-MS (Method 3): RT=0.97 min; m/z=413.44 (M+H).

Example 5

2-[4-(1-Aminocyclobutyl)phenyl]-3-phenylimidazo[1,2-b]pyridazine-6-carboxamide

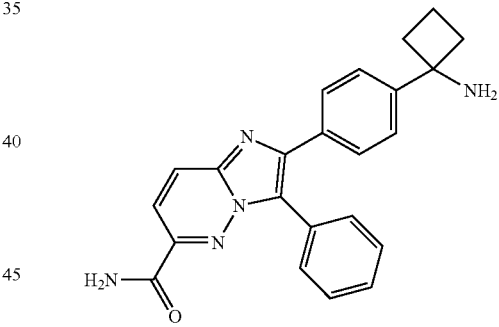

A mixture of ethyl 2-[4-(1-aminocyclobutyl)phenyl]-3-phenylimidazo[1,2-b]pyridazine-6-carboxylate that was prepared in a manner analogous to that described for Example 4, (1.00 g, 93% purity) and ammonia (17.3 mL of a 7M solution in methanol) was heated at 130° C. under microwave irradiation for 5 hours. The volatile components were removed by distillation under reduced pressure. Crystallization from methanol/diisopropyl ether gave the title compound (672 mg, 72% yield) as a yellow solid.

UPLC-MS (Method 2): RT=0.99 min; m/z=366.59 (M−NH$_2$).

1H-NMR (400 MHz, d6-DMSO): δ [ppm]=8.26 (d, 1H), 7.87 (br s, 1H), 7.69 (d, 1H), 7.61-7.63 (m, 2H), 7.55-7.57 (m, 3H), 7.44-7.53 (m, 3H), 7.39 (d, 2H), 2.29-2.36 (m, 2H), 1.89-2.06 (m, 5H), 1.55-1.65 (m, 1H).

Example 6

1-[4-(6-Methyloxy-3-phenylimidazo[1,2-b]pyridazin-2-yl)phenyl]cyclobutanamine

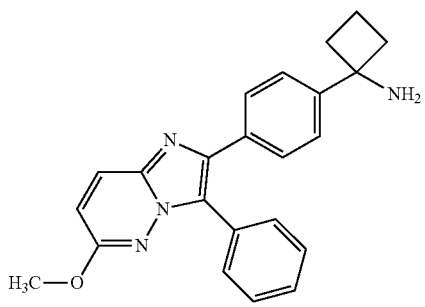 [SMILES: COc1ccc2nc(-c3ccc(C4(N)CCC4)cc3)c(-c3ccccc3)n2n1]

To a mixture of tert-butyl (1-{4-[3-phenyl-6-methoxyimidazo[1,2-b]pyridazin-2-yl]phenyl}cyclobutyl)carbamate that was prepared in a manner analgous to that described for Intermediate Example Int-5 (550 mg, 1.17 mmol) in DCM (7.5 mL) and MeOH (0.8 mL) was added a 4M hydrogen chloride solution in dioxane (5.8 mL, 23.4 mmol, 20.0 eq), and the resulting mixture was stirred at room temperature for 12 h. The resulting mixture was added to ice water, made alkaline with aqueous sodium hydroxide (2N), and extracted with EtOAc (3×25 mL). The combined organic phases were washed, dried ($Na_2SO_4$ anh.) and concentrated under reduced pressure. The resulting material was purified using MPLC (Biotage Isolera; 100 g SNAP cartridge: 100% DCM 3.5 min., gradient to 95% DCM/5% MeOH 1 min., 95% DCM/5% MeOH 3.5 min., gradient to 90% DCM/10% MeOH 1 min., 90% DCM/10% MeOH 4.5 min.) to give 1-[4-(6-methyloxy-3-phenylimidazo[1,2-b]pyridazin-2-yl)phenyl]cyclobutanamine (379 mg, 83% yield):

UPLC-MS (Method 3): RT=1.28 min; m/z (rel intensity) 371 (95, (M+H)$^+$).

1H-NMR (DMSO-$d_6$): δ [ppm]1.52-1.66 (m, 1H), 1.87-2.08 (m, 3H), 2.05-2.28 (br m, 2H), 2.28-2.38 (m, 2H), 3.79 (s, 3H), 6.91 (d, J=9.6 Hz, 1H), 7.35 (d, J=8.7 Hz, 2H), 7.40-7.53 (m, 3H), 7.49 (d, 8.5 Hz, 2H), 7.57 (ddm, J=8.3, 1.5 Hz, 2H), 8.05 (d, J=9.6 Hz).

Example 7

1-[4-(6-Bromo-8-methyloxy-3-phenylimidazo[1,2-b]pyridazin-2-yl)phenyl]-cyclobutanamine

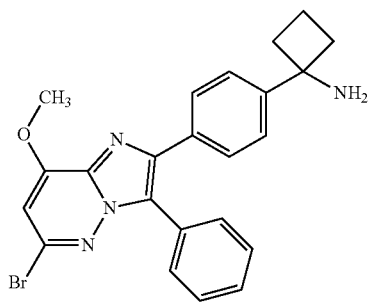 [SMILES: COc1cc(Br)nn2c(-c3ccccc3)c(-c3ccc(C4(N)CCC4)cc3)nc12]

To a solution of tert-butyl (1-{4-[3-phenyl-6-bromo-8-methoxyimidazo[1,2-b]pyridazin-2-yl]phenyl}cyclobutyl)carbamate that was prepared in a manner analgous to that described for Intermediate Example Int-7 (100 mg, 0.18 mmol) in dioxane (4 mL) was added trifluoromethanesulfonic acid (0.61 mL, 1.8 mmol, 10.0 eq), and the resulting mixture was stirred at room temperature for 12 h. The resulting mixture was added to ice water, made alkaline with aqueous sodium hydroxide (2N), and extracted with EtOAc (3×25 mL). The combined organic phases were washed, dried ($Na_2SO_4$ anh.) and concentrated under reduced pressure. The resulting material was purified using MPLC (Biotage Isolera; SNAP 10 g cartridge: 100% DCM 4.0 min., gradient to 95% DCM/5% MeOH 1 min., 95% DCM/5% MeOH 3.5 min., gradient to 90% DCM/10% MeOH 1 min., 90% DCM/10% MeOH 3.5 min., gradient to 80% DCM/20% MeOH 6 min., 80% DCM/20% MeOH 4.7 min.) to give material (40 mg) which was further purified by preparative HPLC (Waters Autopurification System equipped with pump 254, Sample Manager 2767, CFO, DAD 2996, ELSD 2424 and SQD 3001 using a Xselect CSH C18 5 uM 100×30 mm column; 60% water with 1% $HCO_2H$/40% methanol 1 min., gradient to 10% water with 1% $HCO_2H$/90% methanol 7 min) to give 1-[4-(6-bromo-8-methyloxy-3-phenylimidazo[1,2-b]pyridazin-2-yl)phenyl]cyclobutanamine (15 mg, 18%):

UPLC-MS (Method 3): RT=1.32 min; m/z (rel intensity) 432 (95, (M+H-17)$^+$), 449 (60, (M+H)$^+$).

1H-NMR (DMSO-$d_6$): δ [ppm]1.55-1.65 (m, 1H), 1.90-2.00 (m, 1H), 2.03-2.11 (m, 2H), 2.30-2.38 (m, 2H), 4.10 (s, 3H), 7.03 (s, 1H), 7.36 (d, J=8.6 Hz, 2H), 7.45-7.54 (m, 7H).

Example 8

2-[4-(1-Aminocyclobutyl)phenyl]-3-phenylimidazo[1,2-b]pyridazine-6-carboxylic acid

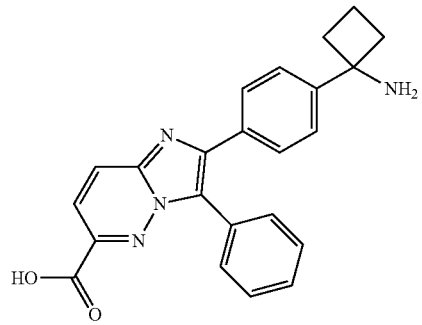 [SMILES: NC1(c2ccc(-c3nc4ccc(C(=O)O)nn4c3-c3ccccc3)cc2)CCC1]

To a solution of ethyl 2-[4-(1-aminocyclobutyl)phenyl]-3-phenylimidazo[1,2-b]pyridazine-6-carboxylate that was prepared in a manner analgous to that described for Example 4 (260 mg, 0.63 mmol) in methanol (1.5 mL) was added aqueous sodium hydroxide (3N, 0.63 mL, 1.89 mmol, 3.0 eq), and the resulting mixture was stirred at 50° C. for 1 h. The resulting mixture was added to ice water, made slightly acidic with aqueous citric acid (10%), and washed with DCM (3×25 mL). The aqueous phase was made alkaline and adjusted to pH4 using hydrochloric acid (1N). The precipitate was collected by filtration, washed with water and dried under high vacuum overnight to yield 218 mg (88% yield) of the title compound.

UPLC-MS (Method 1): RT=0.71 min; m/z (ES$_{neg}$)=383 (M−H)$^-$.

1H-NMR (DMSO-d$_6$, +1 drop TFA-d): δ [ppm]1.77 (m, 1H), 1.10 (m, 1H), 2.40-2.64 (m, 4H, partially obscured by solvent signal), 7.40-7.60 (d, 7H), 7.68 (d, 2H), 7.78 (d, 1H), 8.30 (d, 1H), 8.50 (m, 1H).

Example 9

1-[4-(6,8-Dimethyloxy-3-phenylimidazo[1,2-b]pyridazin-2-yl)phenyl]-cyclobutanamine

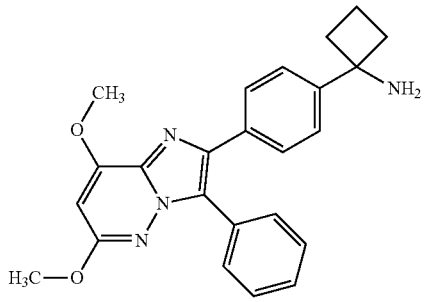 [SMILES: COc1cc(OC)c2nc(-c3ccc(C4(N)CCC4)cc3)c(-c3ccccc3)n2n1]

To a solution of tert-butyl (1-{4-[3-phenyl-6,8-dimethoxyimidazo[1,2-b]pyridazin-2-yl]phenyl}cyclobutyl)carbamate that was prepared in a manner analogous to that described for Intermediate Example Int-7 (0.18 g, 0.37 mmol) in methanol (2.2 mL) and DCM (3.5 mL) was added hydrogen chloride (4M in dioxane, 1.8 mL, 7.3 mmol, 20.0 eq), and the resulting mixture was stirred at room temperature for 20 h. The resulting mixture was added to ice water, made alkaline with aqueous sodium hydroxide (2N), and extracted with EtOAc (3×25 mL). The combined organic phases were dried (Na$_2$SO$_4$) and concentrated under reduced pressure. The resulting material was purified using MPLC (Biotage Isolera; 10 g SNAP cartridge: 100% DCM 6.0 min., gradient to 95% DCM/5% MeOH 4 min., 95% DCM/5% MeOH 5 min., gradient to 90% DCM/10% MeOH 3.5 min.) to give 1-[4-(6,8-dimethyloxy-3-phenylimidazo[1,2-b]pyridazin-2-yl)phenyl]cyclobutanamine (0.11 g, 79%):

UPLC-MS (Method 3): RT=1.31 min; m/z (rel intensity) 384 (100, (M+H-17)$^+$), 401 (70, (M+H)$^+$).

1H-NMR (DMSO-d$_6$): δ [ppm]1.52-1.65 (m, 1H), 1.88-2.07 (m, 5H), 2.27-2.38 (m, 2H), 3.77 (s, 3H), 4.03 (s, 3H), 6.40 (s, 1H), 7.34 (d, J=8.5 Hz, 2H), 7.39-7.50 (m, 5H), 7.51-7.56 (m, 2H).

Example 10

2-[4-(1-Aminocyclobutyl)phenyl]-8-methoxy-3-phenylimidazo[1,2-b]-pyridazine-6-carboxamide

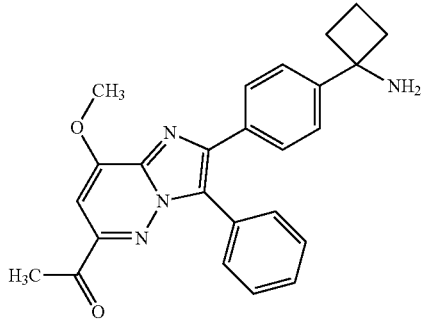 [SMILES: COc1cc(C(C)=O)nn2c(-c3ccccc3)c(-c3ccc(C4(N)CCC4)cc3)nc12]

To a solution of 2-(4-{1-[(tert-butoxycarbonyl)amino]cyclobutyl}phenyl)-8-methoxy-3-phenylimidazo[1,2-b]pyridazine-6-carboxylamide that was prepared in a manner analgous to that described for Intermediate Example Int-10 (0.095 g, 0.18 mmol) in MeOH (1 mL) and DCM (1.8 mL) was added hydrogen chloride (4M in dioxane, 0.9 mL, 3.7 mmol, 20.0 eq), and the resulting mixture was stirred at room temperature for 3 days. The resulting mixture was added to ice water, made alkaline with aqueous sodium hydroxide (2N), and extracted with EtOAc (3×50 mL). The combined organic phases were dried (Na$_2$SO$_4$ anh.) and concentrated under reduced pressure. The resulting material was purified using preparative HPLC (Waters Autopurification System equipped with pump 254, Sample Manager 2767, CFO, DAD 2996, ELSD 2424 and SQD 3001 using a Xselect CSH C18 5 uM 100×30 mm column; 60% water with 1% HCO$_2$H/40% MeOH 1 min., gradient to 10% water with 1% HCO$_2$H/90% MeOH 7 min) to give 2-[4-(1-aminocyclobutyl)phenyl]-8-methoxy-3-phenylimidazo[1,2-b]pyridazine-6-carboxamide (0.020 g, 31%):

UPLC-MS (Method 3): RT=1.03 min; m/z (rel intensity) 397 (100, (M+H-17)$^+$), 414 (50, (M+H)$^+$); ES− m/z (rel intensity) 412 (70, (M−H)$^-$).

1H-NMR (DMSO-d$_6$): δ [ppm]1.53-1.66 (m, 1H), 1.89-2.07 (m, 5H), 2.12 (br s, 2H). 2.28-2.38 (m, 2H), 4.07 (s, 3H), 7.15 (s, 1H), 7.37 (d, J=8.5 Hz, 2H), 7.42-7.56 (m, 6H), 7.56-7.62 (m, 2H), 7.82 (br s, 1H).

Example 11

1-[4-(8-Methoxy-3-phenylimidazo[1,2-b]pyridazin-2-yl)phenyl]cyclobutanamine

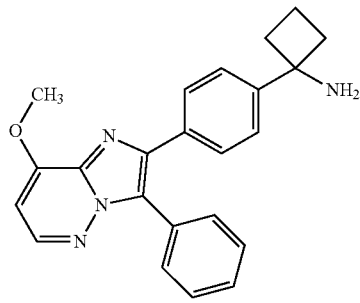 [SMILES: COc1ccnn2c(-c3ccccc3)c(-c3ccc(C4(N)CCC4)cc3)nc12]

To a solution of tert-butyl {1-[4-(8-methoxy-3-phenylimidazo[1,2-b]pyridazin-2-yl)phenyl]cyclobutyl}carbamate that was prepared in a manner analogous to that described for Intermediate Example Int-11 (0.055 g, 0.12 mmol) in a mixture of MeOH (0.7 mL) and DCM (1.1 mL) was added a concentrated aqueous HCl solution (approximately 12N, 0.6 mL). The resulting mixture was stirred at room temperature for 60 h, then poured onto ice water (15 mL). The resulting mixture was made basic with a 2N NaOH solution, then was extracted with EtOAc (3×20 mL). The combined organic phases were dried (Na$_2$SO$_4$ anh.) and concentrated under reduced pressure. The resulting oil (34 mg) was purified using preparative HPLC (Agilent Prep 1200 equipped with 2× Prep Pump, DLA, MWD, ELSD and Prep FC using an XBrigde C18 5 μm 100×30 mm column; gradient from 70% water with 0.2% NH$_3$/30% CH$_3$CN to 40% water with 0.2% NH$_3$/60% CH$_3$CN over 17.5 min, gradient from 40% water with 0.2% NH$_3$/60% CH$_3$CN to 100% CH₃CN over 2.5 min) to give 1-[4-(8-methoxy-3-phenylimidazo[1,2-b]pyridazin-2-yl)phenyl]cyclobutanamine (0.021 g, 48% yield): UPLC-MS (Method 3): RT=1.18 min; m/z (rel intensity) 371 (30, (M+H)⁺).

1H-NMR (DMSO-d₆): δ [ppm]1.52-1.65 (m, 1H), 1.87-2.13 (m, 5H), 2.12 (br s, 2H), 2.28-2.37 (m, 2H), 4.06 (s, 3H), 6.73 (d, J=5.7 Hz 1H), 7.35 (d, J=8.7 Hz, 2H), 7.43-7.50 (m, 5H), 7.53, (d, J=8.7 Hz, 2H).

The following examples were prepared in a manner analogous to Example 11 by reacting the corresponding carmabate intermediates with a concentrated aqueous HCl solution

| Example | Structure/Name | Characterization |
| --- | --- | --- |
| 12 | Methyl 2-[4-(1-aminocyclobutyl)phenyl]-8-methoxy-3-phenylimidazo[1,2-b]pyridazine-6-carboxylate | UPLC-MS (Method 3): RT = 1.21 min; m/z (rel intensity) 429 (70, (M + H)⁺).<br>1H-NMR (DMSO-d₆): δ [ppm] 1.55-1.64 (m, 1H), 1.89-2.05 (m, 4H), 2.12 (br s, 2H), 2.30-2.36 (m, 2H), 3.85 (s, 3H), 4.15 (s, 3H), 7.18 (s, 1H), 7.36 (d, J = 8.6 Hz, 2H), 7.46-7.55 (m, 7H). |
| 13 | 1-[4-(6-Ethyl-8-methoxy-3-phenylimidazo[1,2-b]pyridazin-2-yl)phenyl]cyclobutanamine | UPLC-MS (Method 3): RT = 1.34 min; m/z (rel intensity) 399 (50, (M + H)⁺).<br>1H-NMR (DMSO-d₆): δ [ppm] 1.19 (t, J = 7.5 Hz, 3H), 1.53-1.65 (m, 1H), 1.87-2.10 (m, 5H), 2.27-2.37 (m, 2H), 2.68 (q, J = 7.5 Hz, 2H), 4.05 (s, 3H), 6.70 (s, 1H), 7.34 (d, J = 8.5 Hz, 2H), 7.42-7.52 (m, 7H). |
| 14 | 1-{4-[6-Methoxy-3-phenyl-8-(pyridin-3-yl)imidazo[1,2-b]pyridazin-2-yl]phenyl}cyclobutanamine | UPLC-MS (Method 3): RT = 1.41 min; m/z (rel intensity) 431 (100, (M + H − 17)⁺), 448 (70, (M + H)⁺).<br>1H-NMR (DMSO-d₆): δ [ppm] 1.55-1.65 (m, 1H), 1.87-2.20 (m, 5H), 2.29-2.39 (m, 2H), 3.85 (s, 3H), 7.35 (s, 1H), 7.38 (d, J = 8.5 Hz, 2H), 7.43-7.54 (m, 5H), 7.58-7.63 (m, 3H), 8.70-8.77 (m, 2H), 9.50 (dm, J = 2.2 Hz, 1H). |

| Example | Structure/Name | Characterization |
| --- | --- | --- |
| 15 | 1-{4-[6-Methoxy-3-phenyl-8-(1H-pyrazol-4-yl)imidazo[1,2-b]pyridazin-2-yl]phenyl}cyclobutanamine HCl salt | UPLC-MS (Method 3): RT = 1.34 min; m/z (rel intensity) 420 (100, (M + H − 17)$^+$), 437 (50, (M + H)$^+$). 1H-NMR (DMSO-$d_6$): δ [ppm] 1.56-1.64 (m, 1H), 1.89-2.12 (m, 4H), 2.33-2.38 (m, 3H), 3.78 (s, 3H), 7.23 (s, 1H), 7.36-7.41 (m, 3H), 7.44-7.50 (m, 4H), 7.54-7.62 (m, 4H), 9.22 (s, 1H), 8.60-8.93 (br m, 2H). |
| 16 | 1-[4-(6,8-Diethyl-3-phenylimidazo[1,2-b]pyridazin-2-yl)phenyl]cyclobutanamine | UPLC-MS (Method 3): RT = 1.52 min; m/z (rel intensity) 380 (90, (M + H − 17)$^+$), 397 (100, (M + H)$^+$). 1H-NMR (CD$_3$OD): δ [ppm] 1.33 (t, J = 7.6 Hz, 3H), 1.47 (t, J = 7.6 Hz, 3H), 1.76-1.82 (m, 1H), 2.06-2.15 (m, 2H), 2.24-2.32 (m, 2H), 2.57-2.63 (m, 2H), 2.85 (q, J = 7.6 Hz, 2H), 3.14 (qd, J = 7.6, 1.0 Hz, 2H), 7.08 (s, 1H), 7.42-7.49 (m, 5H), 7.55 (dd, J = 7.9, 1.3 Hz), 7.61 (d, J = 8.5 Hz, 2H). |

Example 17

1-[4-(6-Chloro-3-phenylimidazo[1,2-b]pyridazin-2-yl)phenyl]cyclobutanamine

To a solution of tert-butyl {1-[4-(6-chloro-3-phenylimidazo[1,2-b]pyridazin-2-yl)phenyl]cyclobutyl}carbamate that was prepared in a manner analgous to that described for Intermediate Example Int-6.2 (0.075 g, 0.15 mmol) in MeOH (0.65 mL) and DCM (1.0 mL) was added hydrogen chloride (4M in dioxane, 0.8 mL, 3.2 mmol, 20.0 eq), and the resulting mixture was stirred at room temperature for 19 h. The resulting mixture was added to ice water (50 mL), made alkaline with aqueous sodium hydroxide (2N), and extracted with EtOAc (2×50 mL). The combined organic phases were dried (Na$_2$SO$_4$ anh.) and concentrated under reduced pressure. The resulting material was recrystallized using diisopropyl ether to give 1-[4-(6-chloro-3-phenylimidazo[1,2-b]pyridazin-2-yl)phenyl]cyclobutanamine (0.040 g, 68%):

UPLC-MS (Method 3): RT=1.32 min; m/z (rel intensity) 358 (100, (M+H-17)$^+$), 375 (60, (M+H)$^+$).

1H-NMR (DMSO-$d_6$): δ [ppm]1.52-1.65 (m, 1H), 1.87-2.07 (m, 3H), 2.16 (br s, 2H). 2.27-2.37 (m, 2H), 7.35-7.40 (m, 3H), 7.48-7.56 (m, 7H), 8.25 (d, J=9.4 Hz, 1H).

Example 18

1-[4-(8-Methoxy-3-phenyl-6-vinylimidazo[1,2-b]pyridazin-2-yl)phenyl]-cyclobutanamine To a solution of tert-butyl {1-[4-(8-methoxy-3-phenyl-6-vinylimidazo[1,2-b]pyridazin-2-yl)phenyl]cyclobutyl}carbamate that was prepared in a manner analgous to that described for Intermediate Example Int-12 (40 mg, 0.081 mmol) in dioxane (1.7 mL) was added trifluoromethanesulfonic acid (0.61 mL, 1.8 mmol, 10.0 eq), and the resulting mixture was stirred at room temperature for 12 h. The resulting mixture was added to ice water, made alkaline with aqueous sodium hydroxide (2N), and extracted with EtOAc (3×25 mL). The combined organic phases were washed, dried (Na$_2$SO$_4$ anh.) and concentrated under reduced pressure. The resulting material was purified using MPLC (Biotage Isolera; 10 g SNAP cartridge: 100% DCM 3.0 min., gradient to 95% DCM/5% MeOH 1 min., 95% DCM/5% MeOH 2.5 min., gradient to 90% DCM/10% MeOH 3 min., 90% DCM/10% MeOH 3.5 min.) to give 1-[4-(8-methoxy-3-phenyl-6-vinylimidazo[1,2-b]pyridazin-2-yl)phenyl]cyclobutanamine (0.022 g, 70%):

UPLC-MS (Method 3): RT=1.32 min; m/z (rel intensity) 380 (95, (M+H-17)$^+$), 397 (70, (M+H)$^+$).

1H-NMR (DMSO-d$_6$): δ [ppm]1.54-1.64 (m, 1H), 1.89-2.10 (m, 5H), 2.28-2.36 (m, 2H), 4.11 (s, 3H), 5.63 (d, J=11.4 Hz, 1H), 6.27 (d, J=17.7 Hz, 1H), 6.64 (dd, J=17.7, 11.1 Hz, 1H), 7.06 (s, 1H), 7.35 (d, J=8.3 Hz, 2H), 7.42-7.53 (m, 8H).

The following examples were prepared in a manner analogous to Example 18 by reacting the corresponding carbamate intermediates with trifluoromethanesulfonic acid

| Example | Structure/Name | Characterization |
|---|---|---|
| 19 | 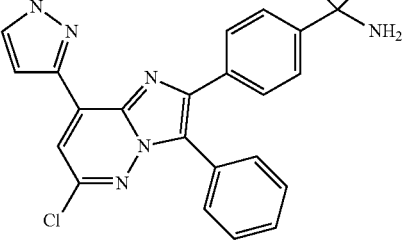<br>1-{4-[6-Chloro-3-phenyl-8-(1H-pyrazol-3-yl)imidazo[1,2-b]pyridazin-2-yl]phenyl}cyclobutanamine | UPLC-MS (Method 3): RT = 1.39 min; m/z (rel intensity) 424 (90 (M + H − 17)$^+$), 441 (100, (M + H)$^+$); ES-m/z (rel intensity) 438 (100, (M − H)$^-$).<br>1H-NMR (DMSO-d$_6$): δ [ppm] 1.55-1.66 (m, 1H), 1.90-1.99 (m, 1H), 2.00-2.09 (m, 2H), 2.31-2.39 (m, 2H), 7.41 (d, J = 8.3 Hz, 2H), 7.49-7.56 (m, 5H), 7.62 (d, J = 8.3 Hz, 2H), 7.74-7.76 (m, 2H), 7.97 (d, J = 2 Hz, 1H). |
| 20 | 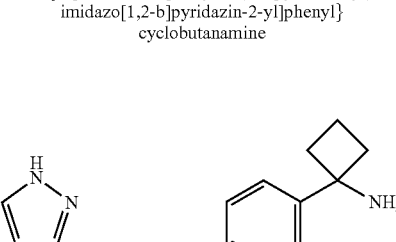<br>1-{4-[3-Phenyl-8-(1H-pyrazol-3-yl)-6-vinylimidazo[1,2-b]pyridazin-2-yl]phenyl}cyclobutanamine | UPLC-MS (Method 3): RT = 1.39 min; m/z (rel intensity) 416 (90 (M + H − 17)$^+$), 433 (100, (M + H)$^+$), 865 (10 (2M + H)$^+$); ES-m/z (rel intensity) 431 (100, (M − H)$^-$).<br>1H-NMR (DMSO-d$_6$): δ [ppm] 1.53-1.67 (m, 1H), 1.88-2.21 (m, 5H), 2.29-2.39 (m, 3H), 5.66 (d, J = 11.1 Hz, 1H), 6.24 (d, J = 17.7 Hz, 1H), 6.76 (dd, J = 17.7, 11.1 Hz, 1H), 7.39 (d, J = 8.3 Hz, 2H), 7.47-7.57 (m, 5H), 7.63 (d, J = 8.5 Hz, 2H), 7.72 (d, J = 1.5 Hz, 1H), 7.93 (br s, 1H), 8.03 (s, 1H). |
| 21 | 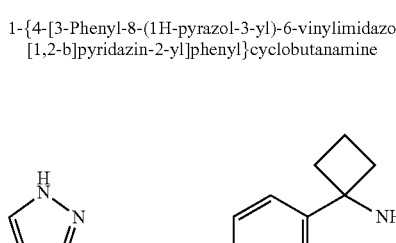<br>1-{4-[6-Ethyl-3-phenyl-8-(1H-pyrazol-3-yl)imidazo[1,2-b]pyridazin-2-yl]phenyl}cyclobutanamine | UPLC-MS (Method 3): RT = 1.42 min; m/z (rel intensity) 418 (90 (M + H − 17)$^+$), 435 (100, (M + H)$^+$), 891 (10 (2M + Na)$^+$); ES-m/z (rel intensity) 433 (100, (M − H)$^-$).<br>1H-NMR (DMSO-d$_6$): δ [ppm] 1.23 (t, J = 7.6 Hz, 3H), 1.55-1.65 (m, 1H), 1.88-1.98 (m, 1H), 2.00-2.20 (m, 3H), 2.31-2.38 (m, 2H), 2.79 (q, J = 7.6 Hz, 2H), 7.39 (d, J = 8.3 Hz, 2H), 7.43-7.57 (m, 5H), 7.68 (s, 1H), 7.69 (br s, 1H)), 7.91 (br s, 1H). |

| Example | Structure/Name | Characterization |
|---------|----------------|------------------|
| 22 | 2-[4-(1-Aminocyclobutyl)phenyl]-8-ethoxy-N-methyl-3-phenylimidazo[1,2-b]pyridazine-6-carboxamide | UPLC-MS (Method 3): RT = 1.17 min; m/z (rel intensity) 425 (100 (M + H − 17)$^+$), 442 (70, (M + H)$^+$), 883 (30 (2M + H)$^+$); ES-m/z (rel intensity) 440 (60, (M − H)$^-$).<br>1H-NMR (DMSO-d$_6$): δ [ppm] 1.47 (t, J = 7.1 Hz, 3H), 1.55-1.65 (m, 1H), 1.89-2.06 (m, 6H), 2.28-2.37 (m, 2H), 2.77 (d, J = 4.6 Hz, 3H), 4.45 (q, J = 7.1 Hz, 2H), 7.10 (s, 1H), 7.37 (d, J = 8.3 Hz, 2H), 7.43-7.53 (m, 6H), 7.55-7.59 (m, 2H), 8.09 (q, J = 4.8 Hz, 1H). |
| 23 | 1-{4-[6-Chloro-8-(1-methyl-1H-pyrazol-5-yl)-3-phenylimidazo[1,2-b]pyridazin-2-yl]phenyl}cyclobutanamine | UPLC-MS (Method 3): RT = 1.39 min; m/z (rel intensity) 438 (100 (M + H − 17)$^+$), 455 (40, (M + H)$^+$).<br>1H-NMR (DMSO-d$_6$): δ [ppm] 1.70-1.82 (m, 1H), 2.03-2.14 (m, 1H), 2.51-2.59 (m, 2H, partially obscured by solvent signal), 4.06 (s, 3H), 7.01 (d, J = 2.0 Hz, 1H), 7.46 (d, J = 8.3 Hz, 2H), 7.51-7.57 (m, 5H), 7.58 (s, 1H), 7.64-7.68 (m, 3H). |
| 24 | 1-{4-[6-Chloro-8-(1H-imidazol-2-yl)-3-phenyl-imidazo[1,2-b]pyridazin-2-yl]phenyl}cyclobutanamine | UPLC-MS (Method 3): RT = 1.33 min; m/z (rel intensity) 424 (100 (M + H − 17)$^+$), 441 (70, (M + H)$^+$), 881 (20, (M + H)$^+$).<br>1H-NMR (DMSO-d$_6$): δ [ppm] 1.54-1.66 (m, 1H), 1.86-2.09 (m, 3H), 2.29-2.39 (m, 2H), 4.06 (s, 3H), 7.28 (s, 1H), 7.41 (d, J = 8.5 Hz, 2H), 7.50-7.57 (m, 4H), 7.60 (d, J = 8.5 Hz, 2H), 7.93 (s, 1H), 8.51 (t, J = 1.4 Hz, 1H), 9.29 (s, 1H). |
| 25 | 1-[4-(3-Phenylimidazo[1,2-b]pyridazin-2-yl)phenyl]cyclobutanamine | UPLC-MS (Method 3): RT = 1.06 min; m/z (rel intensity) 324 (100 (M + H − 17)$^+$), 341 (40, (M + H)$^+$); ES-m/z (rel intensity) 339 (100, (M − H)$^-$).<br>1H-NMR (DMSO-d$_6$): δ [ppm] 1.55-1.67 (m, 1H), 1.86-2.09 (m, 3H), 2.29-2.39 (m, 2H), 4.06 (s, 3H), 7.25 (dd, J = 9.2, 4.3 Hz, 1H), 7.37 (d, J = 8.5 Hz, 2H), 7.43-7.52 (m, 5H), 7.57 (d, J = 8.5 Hz, 2H), 8.16 (dd, J = 9.2, 1.5 Hz, 1H), 8.43 (dd, J = 4.5, 1.7 Hz, 1H). |

-continued

| Example | Structure/Name | Characterization |
|---|---|---|
| 26 | 2-[4-(1-Aminocyclobutyl)phenyl]-8-methoxy-N-methyl-3-phenylimidazo[1,2-b]pyridazine-6-carboxamide | UPLC-MS (Method 3): RT = 1.15 min; m/z (rel intensity) 411 (80 (M + H − 17)+), 427 (60, (M + H)+), 853 (70, (2M + H)+); ES-m/z (rel intensity) 425 (40, (M − H)−).<br>1H-NMR (DMSO-d6): δ [ppm] 1.55-1.65 (m, 1H), 1.89-2.10 (m, 5H), 2.28-2.37 (m, 2H), 2.77 (d, J = 4.8 Hz, 3H), 4.34 (s, 3H), 7.13 (s, 1H), 7.37 (d, J = 8.3 Hz, 2H), 7.46-7.53 (m, 5H), 7.58 (dm, J = 8.3 Hz, 2H), 8.10 (q, J = 4.8 Hz, 1H). |
| 27 | 1-{4-[3-Phenyl-8-(1H-pyrazol-3-yl)imidazo[1,2-b]pyridazin-2-yl]phenyl}cyclobutanamine | UPLC-MS (Method 3): RT = 1.25 min; m/z (rel intensity) 390 (100 (M + H − 17)+), 407 (80, (M + H)+), 813 (10, (2M + H)+); ES-m/z (rel intensity) 405 (100, (M − H)−), 811 (10, (2M − H)−).<br>1H-NMR (DMSO-d6): δ [ppm] 1.54-1.67 (m, 1H), 1.87-2.17 (m, 5H), 2.29-2.38 (m, 2H), 7.40 (d, J = 8.1 Hz, 2H), 7.46-7.57 (m, 5H), 7.64 (d, J = 8.1 Hz, 2H), 7.70-7.75 (m, 2H), 7.93, br s, 1H), 8.46 (d, J = 4.7 Hz, 1H). |
| 28 | 2-[4-(1-Aminocyclobutyl)phenyl]-8-(2-methoxy-ethoxy)-3-phenylimidazo[1,2-b]pyridazine-6-carboxamide | UPLC-MS (Method 3): RT = 1.07 min; m/z (rel intensity) 441 (90 (M + H − 17)+), 458 (100, (M + H)+), 915 (30, (2M + H)+); ES-m/z (rel intensity) 456 (100, (M − H)−), 913 (10, (2M − H)−).<br>1H-NMR (DMSO-d6): δ [ppm] 1.56-1.68 (m, 1H), 1.88-2.10 (m, 4H), 2.29-2.39 (m, 3H), 3.34 (s, 3H), 3.77-3.82 (m, 2H), 4.51-4.56 (m, 2H), 7.16 (s, 1H), 7.38 (d, J = 8.5 Hz, 2H), 7.43-7.61 (m, 9H), 7.82 (br s, 1H). |
| 29 | 1-{4-[8-(Benzyloxy)-6-chloro-3-phenylimidazo[1,2-b]pyridazin-2-yl]phenyl}cyclobutanamine | UPLC-MS (Method 3): RT = 1.52 min; m/z (rel intensity) 464 (100 (M + H − 17)+), 481 (80, (M + H)+), 961 (50, (2M + H)+).<br>1H-NMR (DMSO-d6): δ [ppm] 1.55-1.66 (m, 1H), 1.89-1.98 (m, 1H), 2.00-2.08 (m, 2H), 2.28-2.36 (m, 2H), 5.48 (s, 2H), 7.08 (s, 1H), 7.34 (d, J = 8.6 Hz, 2H), 7.40-7.56 (m, 13H). |

-continued

| Example | Structure/Name | Characterization |
|---------|----------------|------------------|
| 30 | 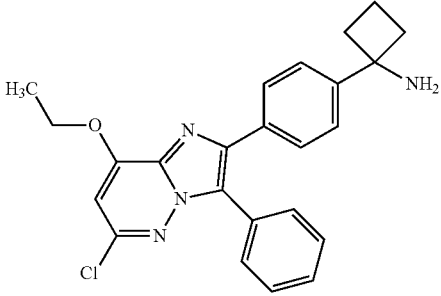 [SMILES: CCOc1cc(Cl)nn2c(-c3ccccc3)c(-c3ccc(C4(N)CCC4)cc3)nc12]<br>1-[4-(6-Chloro-8-ethoxy-3-phenylimidazo[1,2-b]pyridazin-2-yl)phenyl]cyclobutanamine | UPLC-MS (Method 3): RT = 1.39 min; m/z (rel intensity) 402 (100 (M + H − 17)$^+$), 419 (80, (M + H)$^+$), 837 (10, (2M + H)$^+$). 1H-NMR (DMSO-d$_6$): δ [ppm] 1.46 (t, J = 7.0 Hz, 3H), 1.54-1.65 (m, 1H), 1.87-2.07 (m, 5H), 2.27-2.36 (m, 2H), 4.43 (q, J = 7.2 Hz, 2H), 6.93 (s, 1H), 7.35 (d, J = 8.5 Hz, 2H), 7.44-7.54 (m, 7H). |
| 31 | 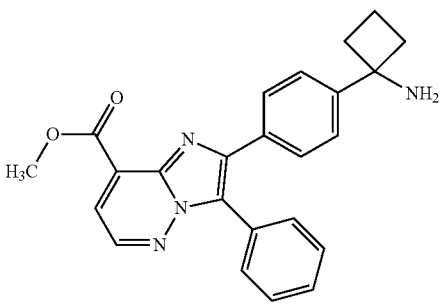 [SMILES: COC(=O)c1ccnn2c(-c3ccccc3)c(-c3ccc(C4(N)CCC4)cc3)nc12]<br>Methyl 2-[4-(1-aminocyclobutyl)phenyl]-3-phenylimidazo[1,2-b]pyridazine-8-carboxylate | UPLC-MS (Method 3): RT = 1.22 min; m/z (rel intensity) 382 (80 (M + H − 17)$^+$), 399 (100, (M + H)$^+$). 1H-NMR (DMSO-d$_6$): δ [ppm] 1.55-1.68 (m, 1H), 1.86-2.10 (m, 3H), 2.29-2.40 (m, 2H), 3.98 (s, 3H), 7.39 (d, J = 8.7 Hz, 2H), 7.48-7.53 (m, 5H), 7.57 (d, J = 8.5 Hz, 2H), 7.64 (d, J = 4.5 Hz, 1H), 8.58 (d, J = 4.5 Hz, 1H). |
| 32 | 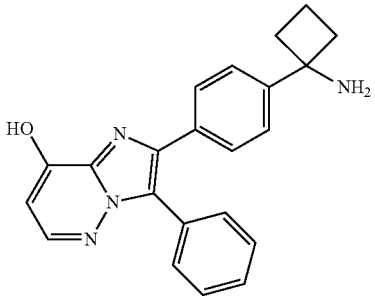 [SMILES: NC1(c2ccc(-c3nc4c(O)ccnn4c3-c3ccccc3)cc2)CCC1]<br>2-[4-(1-Aminocyclobutyl)phenyl]-3-phenylimidazo[1,2-b]pyridazin-8-ol | UPLC-MS (Method 3): RT = 0.69 min; m/z (rel intensity) 340 (70 (M + H − 17)$^+$), 357 (100, (M + H)$^+$), 713 (20, (M + H)$^+$); ES-m/z (rel intensity) 355 (80, (M − H)$^-$). 1H-NMR (DMSO-d$_6$): δ [ppm] 1.67-1.81 (m, 1H), 2.03-2.19 (m, 1H), peak obscured by solvent signal, 5.84 (d, J = 5.8 Hz, 1H), 7.32 (d, J = 8.5 Hz, 2H), 7.35-7.50 (m, 7H), 7.74 (d, J = 5.8 Hz, 1H). |
| 33 | 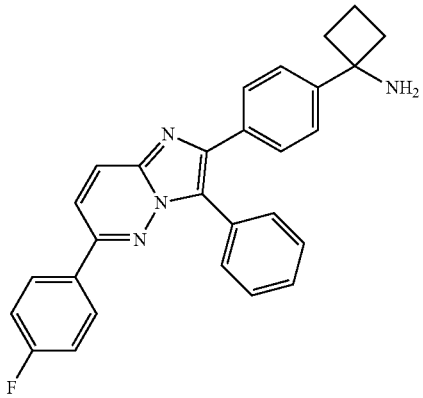 [SMILES: NC1(c2ccc(-c3nc4ccc(-c5ccc(F)cc5)nn4c3-c3ccccc3)cc2)CCC1]<br>1-{4-[6-(4-Fluorophenyl)-3-phenylimidazo[1,2-b]pyridazin-2-yl]phenyl}cyclobutanamine | UPLC-MS (Method 3): RT = 1.05 min; m/z (rel intensity) 418 (40 (M + H − 17)$^+$), 435 (20, (M + H)$^+$); ES-m/z (rel intensity) 479 (80, (M − H + HCO$_2$H)$^-$). 1H-NMR (DMSO-d$_6$): δ [ppm] 1.55-1.69 (m, 1H), 1.86-2.12 (m, 3H), 2-31-2.41 (m, 2H), 5.84 (d, J = 5.8 Hz, 1H), 7.34 (t, J = 8.9 Hz, 2H), 7.39 (d, J = 8.5 Hz, 2H), 7.45-7.63 (m, 7H), 7.85 (d, J = 9.4 Hz, 1H), 8.01 (dd, J = 8.9, 5.5 Hz, 2H), 8.25 (d, J = 9.4 Hz, 1H). |

| Example | Structure/Name | Characterization |
|---|---|---|
| 34 | 2-[4-(1-Aminocyclobutyl)phenyl]-3-phenylimidazo[1,2-b]pyridazine-6,8-dicarboxamide (Approach 2) | UPLC-MS (Method 3): RT = 1.03 min; m/z (rel intensity) 410 (90 (M + H − 17)$^+$), 427 (100, (M + H)$^+$); ES-m/z (rel intensity) 425 (30, (M − H)$^-$), 851 (10, (2M − H)$^-$).<br>1H-NMR (DMSO-d$_6$): δ [ppm] 1.56-1.72 (m, 1H), 1.92-2.04 (m, 1H), 2.07-2.18 (m, 2H), 2.33-2.42 (m, 2H partially obscured by solvent signal), 7.44 (d, J = 8.5 Hz, 2H), 7.48-7.57 (m, 3H), 7.59-7.67 (m, 5H), 7.96 (br s, 1H), 8.20 (d, J = 2.6 Hz, 2H), 8.47 (br s, 1H), 9.17 (br s, 1H). |
| 35 | 2-[4-(1-Aminocyclobutyl)phenyl]-3-phenylimidazo[1,2-b]pyridazin-6-amine | UPLC-MS (Method 3): RT = 1.05 min; m/z (rel intensity) 339 (70 (M + H − 17)$^+$), 356 (100, (M + H)$^+$); ES-m/z (rel intensity) 337 (30, (M − H − 17)$^-$), 851 (10, (2M − H)$^-$).<br>1H-NMR (DMSO-d$_6$): δ [ppm] 1.55-1.66 (m, 1H), 1.90-1.99 (m, 1H), 2.03-2.11 (m, 2H), 2.30-2.48 (m, 2H), 6.27 (s, 2H), 6.64 (d, J = 9.6 Hz, 1H), 7.30 (d, J = 8.6 Hz, 2H), 7.38-7.48 (m, 7H), 7.75 (d, J = 9.6 Hz, 1H), 8.27 (br s, 0.5H). |
| 36 | 1-{4-[6-(Methylsulfanyl)-3-phenylimidazo[1,2-b]pyridazin-2-yl]phenyl}cyclobutanamine | UPLC-MS (Method 3): RT = 1.39 min; m/z (rel intensity) 370 (100 (M + H − 17)$^+$), 387 (80, (M + H)$^+$).<br>1H-NMR (DMSO-d$_6$): δ [ppm] 1.53-1.66 (m, 1H), 1.86-2.09 (m, 5H), 2.28-2.38 (m, 2H), 2.42 (s, 3H), 7.18 (d, J = 9.4 Hz, 1H), 7.37 (d, J = 8.5 Hz, 2H), 7.42-7.59 (m, 7H), 7.98 (d, J = 9.4 Hz, 1H). |
| 37 | N-{2-[4-(1-Aminocyclobutyl)phenyl]-3-phenylimidazo[1,2-b]pyridazin-6-yl}acetamide | UPLC-MS (Method 3): RT = 1.08 min; m/z (rel intensity) 381 (80 (M + H − 17)$^+$), 398 (100, (M + H)$^+$); ES-m/z (rel intensity) 396 (100, (M − H)$^-$).<br>1H-NMR (DMSO-d$_6$): δ [ppm] 1.53-1.67 (m, 1H), 1.88-2.10 (m, 3H), 2.05 (s, 3H), 2.28-2.39 (m, 2H), 7.34 (d, J = 8.5 Hz, 2H), 7.42-7.54 (m, 7H), 7.92 (br d, J = 9.8 Hz, 1H), 8.12 (d, J = 9.8 Hz, 1H), 10.69 (br s, 1H). |

| Example | Structure/Name | Characterization |
|---|---|---|
| 38 | 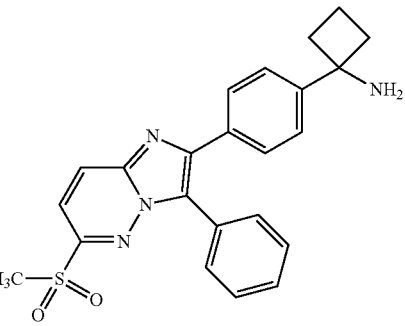<br>N-{2-[4-(1-1-{4-[6-(Methylsulfonyl)-3-phenylimidazo[1,2-b]pyridazin-2-yl]phenyl}cyclobutanamine | UPLC-MS (Method 3): RT = 1.13 min; m/z (rel intensity) 402 (100 (M + H − 17)⁺), 419 (60, (M + H)⁺), 837 (10, (2M + H)⁺).<br>1H-NMR (DMSO-d₆): δ [ppm] 1.65-1.80 (m, 1H), 1.98-2.13 (m, 1H), 2.28-2.39 (m, 2H), 3.35 (s, 3H), 7.16 (br s, 2H), 7.47 (d, J = 8.7 Hz, 2H), 7.51-7.62 (m, 5H), 7.68 (d, J = 8.5 Hz, 2H), 7.77 (d, J = 9.4 Hz, 1H), 8.50 (d, J = 9.4 Hz, 1H). |
| 39 | 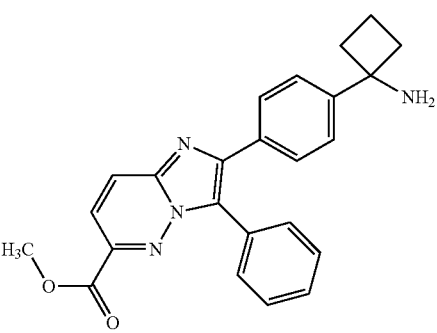 [SMILES: COC(=O)c1ccc2nc(-c3ccc(C4(N)CCC4)cc3)c(-c3ccccc3)n2n1]<br>Methyl 2-[4-(1-aminocyclobutyl)phenyl]-3-phenylimidazo[1,2-b]pyridazine-6-carboxylate | UPLC-MS (Method 3): RT = 1.22 min; m/z (rel intensity) 382 (100 (M + H − 17)⁺), 399 (50, (M + H)⁺).<br>1H-NMR (DMSO-d₆): δ [ppm] 1.60-1.75 (m, 1H), 1.93-2.08 (m, 1H), 2.15-2.26 (m, 2H), peak obscured by solvent signal, 3.86 (s, 3H), 7.42 (d, J = 8.5 Hz, 2H), 7.50-7.56 (m, 5H), 7.62 (d, J = 8.5 Hz, 2H), 7.75 (d, J = 9.4 Hz, 1H), 8.31 (d, J = 9.4 Hz, 1H). |
| 40 | 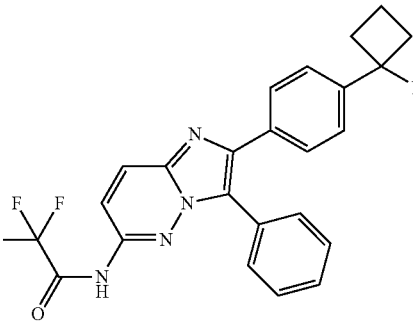<br>N-{2-[4-(1-Aminocyclobutyl)phenyl]-3-phenylimidazo[1,2-b]pyridazin-6-yl}-2,2,2-trifluoroacetamide | UPLC-MS (Method 3): RT = 0.70 min; m/z (rel intensity) 435 (100 (M + H − 17)⁺), 452 (70, (M + H)⁺); ES-m/z (rel intensity) 450 (100, (M − H)⁻).<br>1H-NMR (CD₃OD): δ [ppm] 1.82-1.90 (m, 1H), 2.11-2.19 (m, 1H), 2.64-2.70 (m, 2H), 6.80 (d, J = 9.8 Hz, 1H), 7.42 (d, J = 8.3 Hz, 2H), 7.43-7.48 (m, 3H), 7.52 (dm, J = 7.5 Hz, 2H), 7.58 (d, J = 8.3 Hz, 1H), 7.72 (d, J = 9.8 Hz, 1H). |
| 41 | 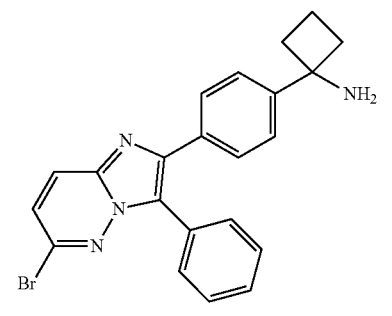<br>1-[4-(6-Bromo-3-phenylimidazo[1,2-b]pyridazin-2-yl)phenyl]cyclobutanamine | UPLC-MS (Method 3): RT = 1.33 min; m/z (rel intensity) 402 (100 (M + H − 17)⁺), 419 (80, (M + H)⁺).<br>1H-NMR (DMSO-d₆): δ [ppm] 1.62-1.69 (m, 1H), 1.95-2.02 (m, 1H), 2.06-2.11 (m, 2H), 2.35-2.41 (m, 2H), 7.42 (d, J = 8.7 Hz, 1H), 7.49 (d, J = 9.4 Hz, 1H), 7.52-7.60 (m, 7H), 8.19 (d, J = 9.4 Hz, 1H). |

-continued

| Example | Structure/Name | Characterization |
|---|---|---|
| 42 | 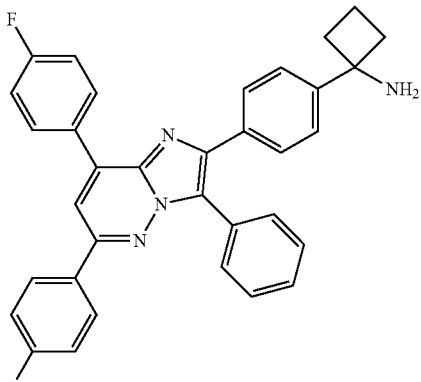<br>1-{4-[6,8-Bis(4-fluorophenyl)-3-phenylimidazo[1,2-b]pyridazin-2-yl]phenyl}cyclobutanamine | UPLC-MS (Method 3): RT = 1.74 min; m/z (rel intensity) 512 (100 (M + H − 17)$^+$), 529 (90, (M + H)$^+$).<br>1H-NMR (DMSO-d$_6$): δ [ppm] 1.62-1.69 (m, 1H), 1.95-2.02 (m, 1H), 2.06-2.11 (m, 2H), 2.37-2.42 (m, 2H), 7.40 (t, J = 8.7 Hz, 2H), 7.45 (d, J = 8.3 Hz, 2H), 7.49-7.55 (m, 3H), 7.59 (t, J = 7.53 Hz, 2H), 7.64 (d, J = 8.3 Hz, 2H), 7.69 (2, J = 7.2 Hz, 2H), 8.12 (s, 1H), 8.18 (dd, J = 9.0, 5.7 Hz, 2H), 8.69 (dd, J = 9.0, 5.7 Hz, 2H). |
| 43 | 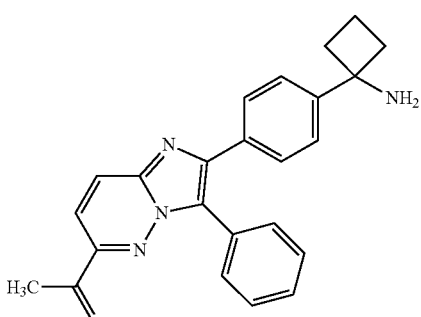<br>1-{2-[4-(1-Aminocyclobutyl)phenyl]-3-phenylimidazo[1,2-b]pyridazin-6-yl}ethanone | UPLC-MS (Method 3): RT = 1.28 min; m/z (rel intensity) 366 (100 (M + H − 17)$^+$), 383 (90, (M + H)$^+$), 765 (5, (2M + H)$^+$).<br>1H-NMR (DMSO-d$_6$): δ [ppm] 1.62-1.70 (m, 1H), 1.96-2.04 (m, 1H), 2.07-2.12 (m, 2H), 2.37-2.43 (m, 2H), 2.56 (s, 3H), 7.46 (d, J = 8.7 Hz, 2H), 7.52-7.55 (m, 1H), 7.57-7.60 (m, 2H), 7.65-7.69 (m, 4H), 7.74 (d, J = 9.4 Hz, 1H), 7.82 (d, J = 9.4 Hz, 1H). |
| 44 | 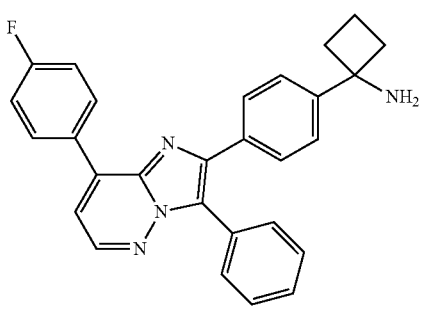 [SMILES: NC1(c2ccc(-c3nc4c(-c5ccc(F)cc5)ccnn4c3-c3ccccc3)cc2)CCC1]<br>1-{4-[8-(4-Fluorophenyl)-3-phenylimidazo[1,2-b]pyridazin-2-yl]phenyl}cyclobutanamine | UPLC-MS (Method 3): RT = 1.53 min; m/z (rel intensity) 418 (100 (M + H − 17)$^+$), 435 (80, (M + H)$^+$). |

| Example | Structure/Name | Characterization |
|---|---|---|
| 45 | N-{2-[4-(1-Aminocyclobutyl)phenyl]-3-phenylimidazo[1,2-b]pyridazin-6-yl}methanesulfonamide | UPLC-MS (Method 3): RT = 0.69 min; m/z (rel intensity) 417 (100 (M + H − 17)⁺), 434 (80, (M + H)⁺); ES-m/z (rel intensity) 432 (100, (M − H)⁻). 1H-NMR (DMSO-d₆): δ [ppm] 1.64-1.81 (m, 1H), 1.99-2.12 (m, 1H), 2.29-2.41 (m, 2H), peak obscured by solvent signal, 6.60 (d, J = 9.6 Hz, 1H), 7.33-7.44 (m, 5H), 7.53-7.61 (m, 4H), 7.65-7.69 (m, 4H), 7.67 (d, J = 9.6 Hz, 1H). |
| 46 | 1-[4-(6-Chloro-8-cyclopropyl-3-phenylimidazo[1,2-b]pyridazin-2-yl)phenyl]cyclobutanamine | UPLC-MS (Method 3): RT = 1.53 min; m/z (rel intensity) 398 (100 (M + H − 17)⁺). 1H-NMR (DMSO-d₆): δ [ppm] 1.23-1.30 (m, 2H), 1.34-1.41 (m, 2H), 1.59-1.70 (m, 1H), 1.92-2.03 (m, 1H), 2.09-2.20 (m, 2H), 2.33-2.39 (m, 1.6H, partially obscured by solvent signal), 2.56-2.64 (m, 1.9H, partially obscured by solvent signal), 7.01 (s, 1H), 7.39 (d, J = 8.5 Hz, 2H), 7.44-7.53 (m, 5H), 7.56 (d, J = 8.3 Hz, 2H). |
| 47 | 1-[4-(3-Phenyl-8-propylimidazo[1,2-b]pyridazin-2-yl)phenyl]cyclobutanamine | UPLC-MS (Method 3): RT = 1.44 min; m/z (rel intensity) 366 (80 (M + H − 17)⁺), 383 (100 (M + H − 17)⁺). 1H-NMR (DMSO-d₆): δ [ppm] 0.98 (t, J = 7.4 Hz, 3H), 1.52-1.66 (m, 1H), 1.84 (apparent sext, J = 7.6 Hz, 2H), 1.90-2.09 (m, 5H), 2.28-2.38 (m, 2H), 2.99 (q, J = 7.5 Hz, 2H), 7.08 (d, J = 4.7 Hz, 1H), 7.37 (d, J = 8.5 Hz, 2H), 7.43-7.57 (m, 8H). |
| 48 | 2-[4-(1-Aminocyclobutyl)phenyl]-3-phenylimidazo[1,2-b]pyridazin-8-amine | UPLC-MS (Method 3): RT = 1.13 min; m/z (rel intensity) 339 (70 (M + H − 17)⁺), 356 (100 (M + H − 17)⁺); ES-m/z (rel intensity) 354 (20, (M − H)⁻). 1H-NMR (DMSO-d₆): δ [ppm] 1.54-1.65 (m, 1H), 1.88-2.07 (m, 3H), 2.28-2.38 (m, 2H), 6.13 (d, J = 5.5 Hz, 1H), 6.92 (br s, 2H), 7.34 (d, J = 8.5 Hz, 2H), 7.39-7.49 (m, 5H), 7.52 (d, J = 8.3 Hz, 2H), 7.89 (d, J = 5.5 Hz, 1H). |

| Example | Structure/Name | Characterization |
|---|---|---|
| 49 | N-{2-[4-(1-Aminocyclobutyl)phenyl]-3-phenylimidazo[1,2-b]pyridazin-8-yl}acetamide | UPLC-MS (Method 3): RT = 1.23 min; m/z (rel intensity) 381 (100 (M + H − 17)$^+$), 398 (100 (M + H − 17)$^+$); ES-m/z (rel intensity) 396 (100, (M − H)$^-$). 1H-NMR (DMSO-d$_6$): δ [ppm] 1.53-1.66 (m, 1H), 1.88-2.15 (m, 5H), 2.28-2.38 (m, 2H), 2.30 (s, 3H), 7.38 (d, J = 8.5 Hz, 2H), 7.43-7.52 (m, 5H), 7.59 (d, J = 8.3 Hz, 2H), 7.90 (d, J = 5.5 Hz, 1H), 8.29 (d, J = 5.3 Hz, 1H). |

Example 50

1-[4-(6-Chloro-7,8-dimethyl-3-phenylimidazo[1,2-b]pyridazin-2-yl)phenyl]-cyclobutanamine

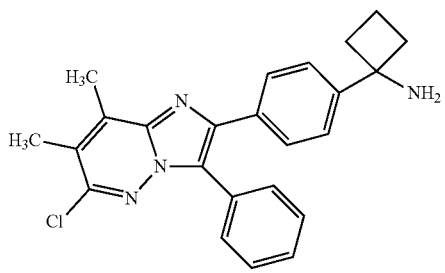 [SMILES: Cc1c(Cl)nn2c(-c3ccccc3)c(-c3ccc(C4(N)CCC4)cc3)nc2c1C]

To a mixture of the tert-butyl {1-[4-(6-chloro-7,8-dimethyl-3-phenylimidazo[1,2-b]pyridazin-2-yl)phenyl]cyclobutyl}carbamate that was prepared in a manner analgous to that described for Intermediate Example Int-32 (179 mg, 0.360 mmol, 1.0 eq) in DCM (2.29 mL) and MeOH (1.44 mL) was added a solution of 4M hydrogen chloride in dioxane (1.78 mL, 7.12 mmol, 20.0 eq) and the mixture was stirred overnight at rt. The mixture was poured onto ice, made alkaline with aqueous sodium hydroxide (2N) and extracted with DCM. The combined organic phases were washed with brine, dried and concentrated in vacuo. The crude mixture was purified via MPLC (Biotage Isolera; 10 g SNAP cartridge: DCM→DCM/ethanol 95/5) to give 64 mg (44% yield) of the title compound.

UPLC-MS (Method 2): RT=1.48 min; m/z=403 (M+H)$^+$.

1H-NMR (400 MHz, d6-DMSO): δ [ppm]=1.59 (m, 1H), 1.93 (m, 1H), 2.02 (m, 2H), 2.11 (br s, 2H), 2.31 (m, 2H), 2.35 (s, 3H), 2.64 (s, 3H), 7.37 (d, 2H), 7.46-7.52 (m, 5H), 7.54 (d, 2H).

Example 51

Methyl 2-[4-(1-aminocyclobutyl)phenyl]-7,8-dimethyl-3-phenylimidazo[1,2-b]pyridazine-6-carboxylate

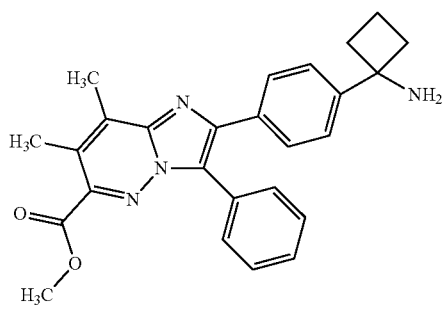 [SMILES: COC(=O)c1nn2c(-c3ccccc3)c(-c3ccc(C4(N)CCC4)cc3)nc2c(C)c1C]

A mixture of crude tert-butyl (1-{4-[bromo(phenyl)acetyl]phenyl}cyclobutyl)carbamate [that was prepared in a manner analogous to that described for Intermediate Example Int-1-A] (630 mg, ~90% purity, 1.28 mmol, 1.0 eq), methyl 6-amino-4,5-dimethylpyridazine-3-carboxylate [that was prepared in a manner analgous to that described for Intermediate Example Int-34] (257 mg, 1.28 mmol, 1.0 eq), N,N-diisopropylethylamine (220 μL, 1.28 mmol, 1.0 eq) in butyronitrile (2.6 mL) was heated for 17 hours at 125° C. On cooling the mixture was partitioned between DCM and water, stirred vigorously and filtered through a silicone coated filter paper. The filtrate was concentrated in vacuo. The crude mixture was purified via preparative reversed phase HPLC to give 89 mg (16% yield) of the title compound directly as the free amine.

UPLC-MS (Method 2): RT=1.35 min; m/z=427 (M+H)$^+$.

1H-NMR (400 MHz, MeOD): δ [ppm]=1.75 (m, 1H), 2.06 (m, 1H), 2.24 (m, 2H), 2.44 (s, 3H), 2.56 (m, 2H), 2.71 (s, 3H), 3.93 (s, 3H), 7.38-7.47 (m, 5H), 7.48-7.54 (m, 2H), 7.60 (d, 2H).

Example 52

2-[4-(1-Aminocyclobutyl)phenyl]-7,8-dimethyl-3-phenylimidazo[1,2-b]-pyridazine-6-carboxamide

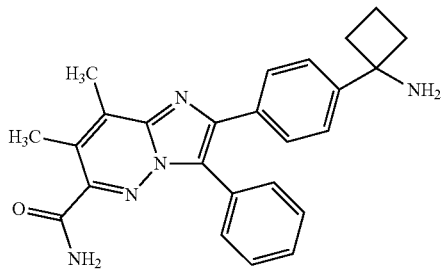 [SMILES: Cc1c(C(N)=O)nn2c(-c3ccccc3)c(-c3ccc(C4(N)CCC4)cc3)nc2c1C]

A solution of methyl 2-[4-(1-aminocyclobutyl)phenyl]-7,8-dimethyl-3-phenylimidazo[1,2-b]pyridazine-6-carboxylate [that was prepared in a manner analgous to that described for Example 51] (80 mg, ~90% purity, 0.170 mmol, 1.0 eq) in 2.41 ml 7N ammonia in MeOH (~100 eq of NH$_3$) was heated for 2 hours at 130° C. by the use of a single mode microwave oven (Biotage). On cooling the volatile components were removed in vacuo. The crude mixture was purified via MPLC (Biotage Isolera; 11 g SNAP NH2 cartridge: hexane/EtOAc 1:1→EtOAc) to give 54 mg (77% yield) of the title compound.

UPLC-MS (Method 2): RT=1.22 min; m/z=412 (M+H)$^+$.

1H-NMR (400 MHz, MeOD): δ [ppm]=1.74 (m, 1H), 2.06 (m, 1H), 2.24 (m, 2H), 2.48 (s, 3H), 2.55 (m, 2H), 2.70 (s, 3H), 7.38-7.48 (m, 5H), 7.52-7.57 (m, 2H), 7.60 (d, 2H).

Example 53

1-[4-(6-Methoxy-7,8-dimethyl-3-phenylimidazo[1,2-b]pyridazin-2-yl)phenyl]-cyclobutanamine

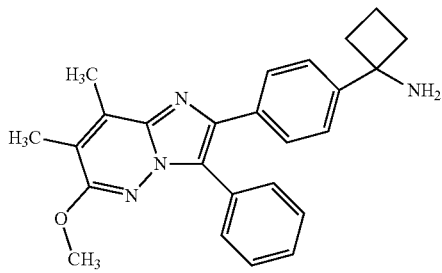 [SMILES: CSc1nn2c(-c3ccccc3)c(-c3ccc(C4(N)CCC4)cc3)nc2c(C)c1C]

To a solution of methyl tert-butyl {1-[4-(6-methoxy-7,8-dimethyl-3-phenylimidazo[1,2-b]pyridazin-2-yl)phenyl]cyclobutyl}carbamate [that was prepared in a manner analgous to that described for Intermediate Example Int-34] (80 mg, ~80% purity, 0.160 mmol, 1.0 eq) in DCM (1.03 mL) and MeOH (0.65 mL) was added a solution of 4M hydrogen chloride in dioxane (0.80 mL, 3.21 mmol, 20.0 eq) and the mixture was stirred for overnight at rt. The mixture was poured onto ice, made alkaline with aqueous sodium hydroxide (2N) and extracted with DCM. The combined organic phases were washed with brine, dried and concentrated in vacuo. The crude mixture was purified via preparative HPLC to give 44 mg (62% yield) of the title compound.

UPLC-MS (Method 2): RT=1.48 min; m/z=399 (M+H)$^+$.

1H-NMR (400 MHz, d6-DMSO): δ [ppm]=1.61 (m, 1H), 1.94 (m, 1H), 2.05 (m, 2H), 2.16 (s, 3H), 2.34 (m, 2H), 2.52 (s, 3H), 3.81 (s, 3H), 7.32-7.42 (m, 3H), 7.45 (m, 2H), 7.51 (m, 2H), 7.55 (m, 2H), NH2 not assigned.

Example 54

1-{4-[7,8-Dimethyl-6-(methylsulfanyl)-3-phenylimidazo[1,2-b]pyridazin-2-yl]-phenyl}cyclobutanamine

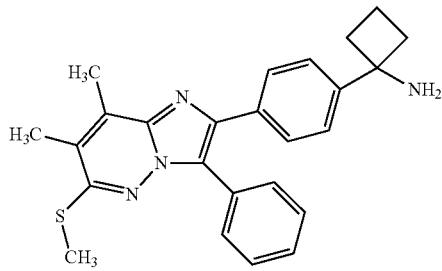

To a mixture of the tert-butyl (1-{4-[7,8-dimethyl-6-(methylsulfanyl)-3-phenylimidazo[1,2-b]pyridazin-2-yl]phenyl}cyclobutyl)carbamate that was prepared in a manner analgous to that described for Intermediate Example Int-35 (95 mg, 0.190 mmol, 1.0 eq) in DCM (1.19 mL) and MeOH (0.75 mL) was added a solution of 4M hydrogen chloride in dioxane (0.92 mL, 3.69 mmol, 20.0 eq) and the mixture was stirred overnight at rt. The mixture was poured onto ice, made alkaline, treated with DCM and filtered through a phase separator. The volatile components of the organic phase were removed in vacuo to give 75 mg (94% yield) of the title compound.

UPLC-MS (Method 2): RT=1.55 min; m/z=415 (M+H)$^+$.

1H-NMR (400 MHz, d6-DMSO): δ [ppm]=1.60 (m, 1H), 1.87-2.09 (m, 3H), 2.12 (br s, 2H), 2.22 (s, 3H), 2.33 (m, 2H), 2.38 (s, 3H), 2.55 (s, 3H), 7.33-7.50 (m, 5H), 7.51-7.60 (m, 4H).

Example 55

1-[4-(6-Ethoxy-7,8-dimethyl-3-phenylimidazo[1,2-b]pyridazin-2-yl)phenyl]-cyclobutanamine

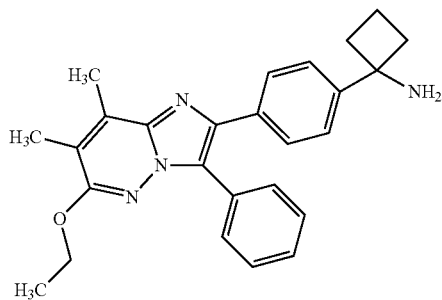 [SMILES: CCOc1nn2c(-c3ccccc3)c(-c3ccc(C4(N)CCC4)cc3)nc2c(C)c1C]

To a mixture of the tert-butyl {1-[4-(6-ethoxy-7,8-dimethyl-3-phenylimidazo[1,2-b]pyridazin-2-yl)phenyl]cyclobutyl}carbamate that was prepared in a manner analgous to that described for Intermediate Example Int-36 (210 mg, 0.410 mmol, 1.0 eq) in DCM (2.64 mL) and MeOH (1.66 mL) was added a solution of 4M hydrogen chloride in dioxane (2.05 mL, 8.19 mmol, 20.0 eq) and the mixture was stirred overnight at rt. The mixture was poured onto ice, made alkaline, treated with DCM and filtered through a phase separator. The volatile components of the organic phase were removed in vacuo to give 145 mg (82% yield) of the title compound.

UPLC-MS (Method 2): RT=1.56 min; m/z=414 (M+H)+.
1H-NMR (400 MHz, d6-DMSO): δ [ppm]=1.30 (t, 3H), 1.59 (m, 1H), 1.87-2.10 (m, 5H), 2.15 (s, 3H), 2.33 (m, 2H), 2.51 (s, 3H), 4.17 (q, 2H), 7.34 (m, 2H), 7.37-7.50 (m, 4H), 7.50-7.56 (m, 3H).

Example 56

Methyl 2-[4-(1-aminocyclobutyl)phenyl]-3-phenyl-8-(1H-pyrazol-3-yl)-imidazo[1,2-b]pyridazine-6-carboxylate

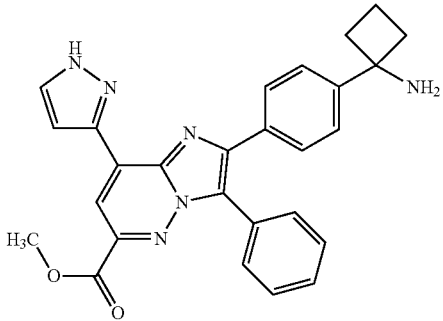 [SMILES: COC(=O)c1cc(-c2cc[nH]n2)c2nc(-c3ccc(C4(N)CCC4)cc3)c(-c3ccccc3)n2n1]

A solution of 1-{4-[6-chloro-3-phenyl-8-(1H-pyrazol-3-yl)imidazo[1,2-b]pyridazin-2-yl]phenyl}cyclobutanamine that was prepared in a manner analgous to that described for Example 19 (0.59 g, 1.34 mmol) in MeOH (2.2 mL) and THF (0.2 mL) in an autoclave was added 1,1'-bis(diphenylphosphino)ferrocenepalladium(II) dichloride (0.22 g, 0.27 mmol, 0.20 equiv) and triethylamine (0.20 mL, 1.47 mmol, 1.1 equiv.). The autoclave was flushed with CO (approximately 5 bar) three times, then was pressurized with CO (5.2 bar), stirred at room temperature 30 min., and briefly placed under reduced atmosphere (0.06 bar). The autoclave was then pressurized with CO (5.9 bar at 20° C.), heated to 110° C., and stirred at this temperature for 22 h.

The resulting solution was concentrated under reduced pressure. The resulting material was purified using MPLC (Biotage Isolera; SNAP 25 g cartridge: 100% DCM 2.0 min., gradient to 95% DCM/5% MeOH 1.0 min., 95% DCM/5% MeOH 2.5 min., gradient to 90% DCM/10% MeOH 1.5 min., 90% DCM/10% MeOH 4.5 min.) to give an impure material (0.45 g). A portion of the material was further purified using preparative HPLC (Agilent Prep 1200 equipped with 2× Prep Pump, DLA, MWD, ELSD and Prep FC using an XBrigde C18 5 μm 100×30 mm column; gradient from 70% water with 0.2% NH3/30% CH3CN to 40% water with 0.2% NH3/60% CH3CN over 17.5 min, gradient from 40% water with 0.2% NH3/60% CH3CN to 100% CH3CN over 2.5 min) to give methyl 2-[4-(1-aminocyclobutyl)phenyl]-3-phenyl-8-(1H-pyrazol-3-yl)imidazo[1,2-b]pyridazine-6-carboxylate (0.013 g, 17% based on purification of 11%):

UPLC-MS (Method 3): RT=1.28 min; m/z (rel intensity) 448 (100 (M+H-17)+), 465 (80, (M+H)+); ES− m/z (rel intensity) 463 (40, (M−H)−).

1H-NMR (d6-DMSO): δ 1.56-1.67 (m, 1H), 1.91-2.00 (m, 1H), 2.02-2.11 (m, 2H), 2.32-2.39 (m, 2H), 3.88 (s, 3H), 7.42 (d, J=8.6 Hz, 2H), 7.51-7.58 (m, 5H), 7.65 (d, J=8.3 Hz, 2H), 7.77 (d, J=2.3 Hz, 1H), 7.98 (br s, 1H), 8.28 (s, 1H).

The following examples were prepared in a manner analogous to Example 56 by reacting the corresponding halide with MeOH and CO in the presence of 1,1'-bis(diphenylphosphino)ferrocenepalladium(II) dichloride

| Example | Structure/Name | Characterization |
|---|---|---|
| 57 | Methyl 2-[4-(1-aminocyclobutyl)phenyl]-8-ethoxy-3-phenylimidazo[1,2-b]pyridazine-6-carboxylate | UPLC-MS (Method 3): RT = 1.29 min; m/z (rel intensity) 426 (100 (M + H − 17)+), 443 (100, (M + H)+).<br>1H-NMR (DMSO-d6): δ [ppm] 1.48 (t, J = 7.1 Hz, 3H), 1.56-1.65 (m, 1H), 1.89-2.14 (m, 5H), 2.29-2.36 (m, 2H), 3.85 (s, 3H), 4.47 (q, J = 7.1 Hz, 2H), 7.14 (s, 1H), 7.37 (d, J = 8.6 Hz, 2H), 7.47-7.54 (m, 7H). |

| Example | Structure/Name | Characterization |
|---|---|---|
| 58 | Methyl 2-[4-(1-aminocyclobutyl)phenyl]-8-(1H-imidazol-2-yl)-3-phenylimidazo[1,2-b]pyridazine-6-carboxylate | UPLC-MS (Method 3): RT = 1.25 min; m/z (rel intensity) 448 (100 (M + H − 17)$^+$), 465 (80, (M + H)$^+$), 929 (20, (2M + H)$^+$). 1H-NMR (DMSO-d$_6$): δ [ppm] 1.57-1.68 (m, 1H), 12.90-2.00 (m, 1H), 2.02-2.12 (m, 2H), 2.31-2.39 (m, 2H), 3.90 (s, 3H), 7.27 (s, 1H), 7.43 (d, J = 8.5 Hz, 2H), 7.52-7.59 (m, 6H), 7.63 (d, J = 8.5 Hz, 2H), 8.09 (s, 1H), 8.57 (s, 1H), 9.31 (s, 1H). |

Example 59 tert-Butyl {1-[4-(8-acetamido-3-phenylimidazo[1,2-b]pyridazin-2-yl)phenyl]-cyclobutyl}carbamate

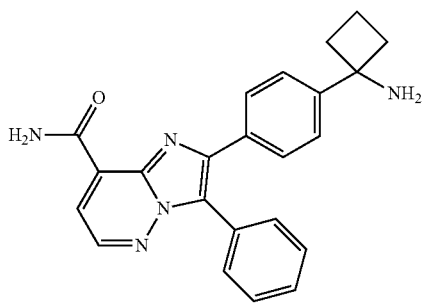 [SMILES: NC(=O)c1ccnn2c(-c3ccccc3)c(-c3ccc(C4(N)CCC4)cc3)nc12]

A solution of methyl 2-[4-(1-aminocyclobutyl)phenyl]-3-phenylimidazo[1,2-b]pyridazine-8-carboxylate that was prepared in a manner analogous to that described for Example 31 (0.040 g, 0.10 mmol) in a solution of ammonia in MeOH (7N, 0.7 mL, 5.0 mmol, 50 equiv) was irradiated in a microwave apparatus at 130° C. for 90 min. The resulting mixture was concentrated under reduced pressure. The resulting material was triturated with diisopropyl ether to give tert-butyl {1-[4-(8-acetamido-3-phenylimidazo[1,2-b]pyridazin-2-yl)phenyl]cyclobutyl}carbamate (0.025 g, 60%):

UPLC-MS (Method 3): RT=1.17 min; m/z (rel intensity) 367 (100, (M+H-17)$^+$), 384 (70, (M+H)$^+$).

1H-NMR (DMSO-d$_6$): δ [ppm]1.54-1.69 (m, 1H), 1.90-2.01 (m, 1H), 2.03-2.13 (m, 2H), 2.31-2.40 (m, 2H), 7.41 (d, J=8.5 Hz, 2H), 7.48-7.56 (m, 5H), 7.61 (d, J=8.5 Hz, 2H), 7.75 (d, J=4.7 Hz, 1H), 8.41 (br s, 1H), 8.63 (d, J=4.7 Hz, 1H), 9.25 (br s, 1H).

The following examples were prepared in a manner analogous to Example 59 by reacting the corresponding ester with ammonia

| Example | Structure/Name | Characterization |
|---|---|---|
| 60 | 2-[4-(1-Aminocyclobutyl)phenyl]-3-phenyl-8-(1H-pyrazol-3-yl)imidazo[1,2-b]pyridazine-6-carboxamide | UPLC-MS (Method 3): RT = 1.11 min; m/z (rel intensity) 433 (100 (M + H − 17)$^+$), 450 (80, (M + H)$^+$), 921 (10, (2M + Na)$^+$); ES− m/z (rel intensity) 448 (100, (M − H)$^-$). 1H-NMR (DMSO-d$_6$): δ [ppm] 1.56-1.68 (m, 1H), 1.89-2.10 (m, 3H), 2.31-2.41 (m, 3H), 7.43 (d, J = 8.5 Hz, 2H), 7.47-7.56 (m, 4H), 7.62-7.68 (m, 4H), 7.75 (d, J = 2.0 Hz, 1H), 7.85 (br s, 1H), 7.95 (br s, 1H), 8.25 (s, 1H). |

-continued

| Example | Structure/Name | Characterization |
|---|---|---|
| 61 | 2-[4-(1-Aminocyclobutyl)phenyl]-8-ethoxy-3-phenylimidazo[1,2-b]pyridazine-6-carboxamide | UPLC-MS (Method 3): RT = 1.11 min; m/z (rel intensity) 411 (60 (M + H − 17)$^+$), 428 (70, (M + H)$^+$); ES− m/z (rel intensity) 446 (10, (M − H)$^-$).<br>1H-NMR (DMSO-d$_6$): δ [ppm] 1.47 (t, J = 7.1 Hz, 3H), 1.57-1.65 (m, 1H), 1.89-2.14 (m, 5H), 2.28-2.37 (m, 2H), 4.45 (q, J = 7.1 Hz, 2H), 7.12 (s, 1H), 7.37 (d, J = 8.3 Hz, 2H), 7.43-7.55 (m, 2H), 7.62-7.68 (m, 6H), 7.59 (d, J = 8.1 Hz, 2H), 7.82 (br s, 1H). |

The following examples were prepared in a manner analogous to Example 59 by reacting the corresponding ester with methylamine

| Example | Structure/Name | Characterization |
|---|---|---|
| 62 | 2-[4-(1-Aminocyclobutyl)phenyl]-8-(1H-imidazol-2-yl)-N-methyl-3-phenylimidazo[1,2-b]pyridazine-6-carboxamide | 1H-NMR (CD$_3$OD): δ [ppm] 1.70-1.82 (m, 1H), 1.99-2.14 (m, 1H), 2.19-2.31 (m, 2H), 2.50-2.61 (m, 2H), 7.29 (s, 1H), 7.40 (d, J = 8.5 Hz, 2H), 7.52-7.61 (m, 5H), 7.68 (d, J = 8.5 Hz, 2H), 7.99 (s, 1H), 8.33 (s, 1H), 9.38 (s, 1H). |
| 63 | 2-[4-(1-Aminocyclobutyl)phenyl]-N-methyl-3-phenylimidazo[1,2-b]pyridazine-8-carboxamide | UPLC-MS (Method 3): RT = 1.25 min; m/z (rel intensity) 381 (100 (M + H − 17)$^+$), 398 (50, (M + H)$^+$).<br>1H-NMR (DMSO-d$_6$): δ [ppm] 1.60-1.70 (m, 1H), 1.93-2.03 (m, 1H), 2.07-2.14 (m, 2H), 2.35-2.43 (m, 2H), 3.05 (d, J = 4.8 Hz, 3H), 7.44 (d, J = 8.5 Hz, 2H), 7.51-7.57 (m, 5H), 7.68 (d, J = 8.5 Hz, 2H), 7.79 (d, J = 4.5 Hz, 1H), 8.66 (d, J = 4.5 Hz, 1H), 9.75 (q, J = 4.5 Hz, 1H). |

| Example | Structure/Name | Characterization |
|---|---|---|
| 64 | 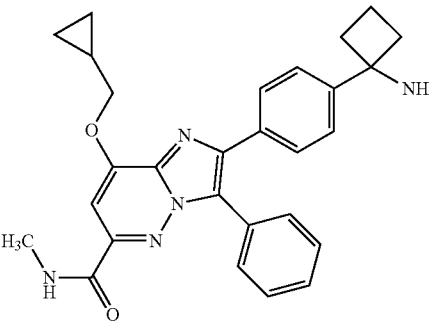<br>2-[4-(1-Aminocyclobutyl)phenyl]-8-(cyclopropylmethoxy)-N-methyl-3-phenylimidazo[1,2-b]pyridazine-6-carboxamide | UPLC-MS (Method 3): RT = 1.27 min; m/z (rel intensity) 451 (70 (M + H − 17)$^+$), 468 (100, (M + H)$^+$), 935 (70, (2M + H)$^+$); ES− m/z (rel intensity) 466 (100, (M − H)$^−$), 933 (10, (2M − H)$^−$), 1H-NMR (DMSO-$d_6$): δ [ppm] 0.41-0.46 (m, 2H), 0.62-0.68 (m, 2H), 1.33-1.41 (m, 1H), 1.55-1.65 (m, 1H), 1.90-2.10 (m, 5H), 2.29-2.37 (m, 2H), 2.77 (d, J = 4.8 Hz, 3H), 4.24 (d, J = 7.3 Hz, 2H), 7.08 (s, 1H), 7.37 (d, J = 8.3 Hz, 2H), 7.45-7.53 (m, 5H), 7.58 (d, J = 6.8 Hz, 2H), 8.08 (q, J = 4.6 Hz, 1H). |
| 65 | 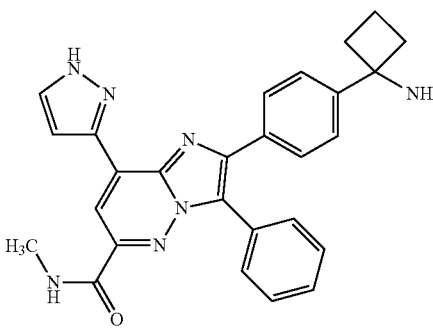<br>2-[4-(1-Aminocyclobutyl)phenyl]-N-methyl-3-phenyl-8-(1H-pyrazol-3-yl)imidazo[1,2-b]pyridazine-6-carboxamide | UPLC-MS (Method 3): RT = 1.18 min; m/z (rel intensity) 447 (100 (M + H − 17)$^+$), 464 (90, (M + H)$^+$), 927 (5, (2M + H)$^+$); ES− m/z (rel intensity) 462 (40, (M-H)$^−$), 925 (10, (2M − H)$^−$), 1H-NMR (DMSO-$d_6$): δ [ppm] 1.56-1.66 (m, 1H), 1.90-1.99 (m, 1H), 2.00-2.09 (m, 2H), 2.31-2.39 (m, 2H), 2.80 (d, J = 4.8 Hz, 3H), 7.42 (d, J = 8.3 Hz, 2H), 7.48-7.55 (m, 3H), 7.61-7.65 (m, 4H), 7.75 (d, J = 2.3 Hz, 1H), 7.95 (br d, J = 1.8 Hz, 1H), 8.15 (br q, J = 4.8 Hz, 1H), 8.24 (s, 1H). |

The following examples were prepared in a manner analogous to Example 59 by reacting the corresponding ester with ethylamine

| Example | Structure/Name | Characterization |
|---|---|---|
| 66 | 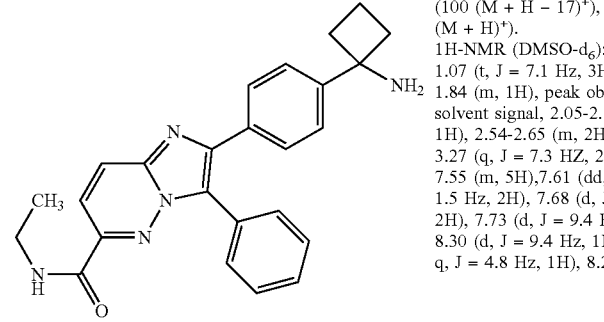<br>2-[4-(1-Aminocyclobutyl)phenyl]-N-ethyl-3-phenylimidazo[1,2-b]pyridazine-6-carboxamide | UPLC-MS (Method 3): RT = 1.17 min; m/z (rel intensity) 395 (100 (M + H − 17)$^+$), 412 (50, (M + H)$^+$). 1H-NMR (DMSO-$d_6$): δ [ppm] 1.07 (t, J = 7.1 Hz, 3H), 1.72-1.84 (m, 1H), peak obscured by solvent signal, 2.05-2.16 (m, 1H), 2.54-2.65 (m, 2H), 2.31-3.27 (q, J = 7.3 HZ, 2H), 7.46-7.55 (m, 5H), 7.61 (dd; J = 7.6, 1.5 Hz, 2H), 7.68 (d, J = 8.6 Hz, 2H), 7.73 (d, J = 9.4 Hz, 1H), 8.30 (d, J = 9.4 Hz, 1H), 8.15 (br q, J = 4.8 Hz, 1H), 8.24 (s, 1H). |

Example 67

2-[4-(1-Aminocyclobutyl)phenyl]-3-phenyl-8-(1H-pyrazol-3-yl)imidazo[1,2-b]-pyridazine-6-carboxylic acid

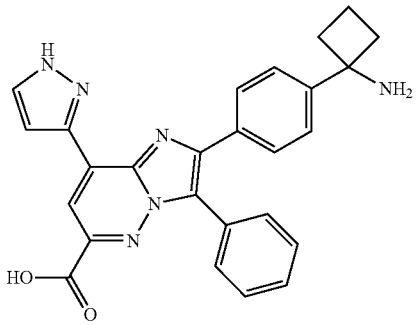 [SMILES: NC1(c2ccc(-c3nc4c(-c5cc[nH]n5)cc(C(=O)O)nn4c3-c3ccccc3)cc2)CCC1]

To a solution of methyl 2-[4-(1-aminocyclobutyl)phenyl]-3-phenyl-8-(1H-pyrazol-3-yl)imidazo[1,2-b]pyridazine-6-carboxylate that was prepared in a manner analgous to that described for Example 56 (0.19 g, 0.41 mmol) in MeOH (5 mL) was added an aqueous NaOH solution (10% 0.65 mL, 1.64 mmol, 4.0 equiv). The resulting mixture was stirred at room temperature for 48 h. Water 10 mL) was added to the resulting mixture and the pH was adjusted to pH 4 using an aqueous 2N HCl solution. The resulting precipitate was collected by filtration, and recrystallized from dimethyl sulfoxide to give 2-[4-(1-aminocyclobutyl)phenyl]-3-phenyl-8-(1H-pyrazol-3-yl)imidazo[1,2-b]pyridazine-6-carboxylic acid (0.012 g, 6%).

UPLC-MS (Method 3): RT=0.70 min; m/z (rel intensity) 434 (40 (M+H-17)$^+$), 451 (100, (M+H)$^+$); ES− m/z (rel intensity) 449 (70, (M−H)$^−$), 899 (50, (2M−H)$^−$), 1H-NMR (DMSO-d$_6$): δ [ppm]1.70-1.83 (m, 1H), 2.04-2.17 (m, 1H), 2.03-2.13 (m, 2H), 2.53-2.64 (m, 3.5H partially obscured by solvent signal), 7.50 (d, J=8.5 Hz, 2H), 7.52-7.58 (m, 5H), 7.75-7.80 (m, 3H), 7.97 (d, J=2.3 Hz, 1H), 8.30 (s, 1H).

Example 68

2-[4-(1-Aminocyclobutyl)phenyl]-N-methyl-3-phenylimidazo[1,2-b]-pyridazine-6-carboxamide

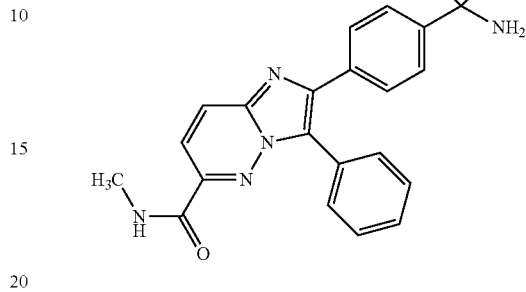

To a solution of 2-[4-(1-aminocyclobutyl)phenyl]-3-phenylimidazo[1,2-b]pyridazine-6-carboxylic acid that was prepared in a manner analgous to that described for Example 8 (0.15 g, 0.39 mmol) and methylamine (2M in THF, 1.43 mL, 2.93 mmol, 7.5 equiv) in DMF (1 mL) was added PYBOP (0.22 g, 0.43 mmol 1.10 equiv) and N,N-diisopropylethylamine (0.27 mL, 1.56 mmol, 4.0 equiv). The resulting mixture was stirred at room temperature for 25 h, then was treated with water (10 mL). The resulting aqueous mixture was extracted with EtOAc (4×15 mL). The combined organic phases were washed with water (2×15 mL), dried (Na2SO4 anh.) and concentrated under reduced pressure. The resulting material was triturated with MeOH to give 2-[4-(1-aminocyclobutyl)phenyl]-N-methyl-3-phenylimidazo[1,2-b]pyridazine-6-carboxamide (0.085 g, 55%):

UPLC-MS (Method 3): RT=1.09 min; m/z (rel intensity) 381 (100 (M+H-17)$^+$), 398 (70, (M+H)$^+$), 795 (10, (2M+H)$^+$); ES− m/z (rel intensity) 396 (40, (M−H)$^−$).

1H-NMR (DMSO-d$_6$): δ [ppm]1.55-1.66 (m, 1H), 1.89-2.08 (m, 5H), 2.28-2.38 (m, 2H), 2.78 (d, J=4.7 Hz, 3H), 7.38 (d, J=8.3 Hz, 2H), 7.46-7.56 (m, 5H), 7.61 (dd, J=7.7, 1.3 Hz, 2H), 7.68 (d, J=9.4 Hz, 1H), 8.16 (br q, J=4.7 Hz, 1H), 8.26 (s, 1H).

The following examples were prepared in a manner analogous to Example 68 by the PYBOP-mediated reaction of the appropriate carboxylic acid with the appropriate amine

| Example | Structure/Name | Characterization |
|---|---|---|
| 69 | 2-[4-(1-Aminocyclobutyl)phenyl]-N,N-dimethyl-3-phenylimidazo[1,2-b]pyridazine-6-carboxamide | UPLC-MS (Method 3): RT = 1.09 min; m/z (rel intensity) 395 (100 (M + H − 17)$^+$), 412 (90, (M + H)$^+$), 823 (10, (2M + H)$^+$); ES− m/z (rel intensity) 426 (100, (M − H)$^−$), 853 (10, (2M − H)$^−$). 1H-NMR (DMSO-d$_6$): δ [ppm] 1.56-1.65 (m, 1H), 1.89-2.07 (m, 5H), 2.28-2.36 (m, 2H), 2.97 (s, 3H), 2.99 (s, 3H), 7.36-7.39 (m, 3H), 7.45-7.54 (m, 5H),7.57 (d; J = 8.3 Hz, 2H), 8.24 (d, J = 9.4 Hz, 1H). |

| Example | Structure/Name | Characterization |
|---|---|---|
| 70 | 2-[4-(1-Aminocyclobutyl)phenyl]-N-(2-hydroxyethyl)-3-phenylimidazo[1,2-b]pyridazine-6-carboxamide | UPLC-MS (Method 3): RT = 0.99 min; m/z (rel intensity) 411 (100 (M + H − 17)$^+$), 427 (80, (M + H)$^+$), 855 (10, (2M + H)$^+$). 1H-NMR (DMSO-d$_6$): δ [ppm] 1.58-1.66 (m, 1H), 1.90-2.08 (m, 5H), 2.29-2.37 (m, 2H), 3.33 (q, J = 5.8 Hz, 2H), 3.47 (q, J = 5.6 Hz, 2H), 4.75 (t, J = 5.3 Hz, 1H), 7.39 (d, J = 8.3 Hz, 2H), 7.45-7.54 (m, 3H), 7.56 (d; J = 8.3 Hz, 2H), 7.61 (dm, J = 8.3 Hz, 2H), 7.70 (d, J = 9.4 Hz, 1H), 8.06 (t, J = 6.1 Hz, 1H), 8.28 (d, J = 9.60 Hz, 1H). |
| 71 | 2-[4-(1-Aminocyclobutyl)phenyl]-N-(2-hydroxyethyl)-3-phenyl-8-(1H-pyrazol-3-yl)imidazo[1,2-b]pyridazine-6-carboxamide | UPLC-MS (Method 3): RT = 1.02 min; m/z (rel intensity) 477 (60 (M + H − 17)$^+$), 494 (100, (M + H)$^+$); ES− m/z (rel intensity) 492 (20, (M − H)$^-$). 1H-NMR (DMSO-d$_6$): δ [ppm] 1.56-1.66 (m, 1H), 1.90-2.14 (m, 5H), 2.32-2.39 (m, 2H), 3.36 (q, J = 5.8 Hz, 2H), 3.49 (q, J = 5.6 Hz, 2H), 4.76 (t, J = 5.3 Hz, 1H), 7.42 (d, J = 8.6 Hz, 2H), 7.47-7.55 (m, 3H), 7.62-7.67 (m, 4H), 7.76 (d, J = 2.3 Hz, 1H), 7.94 (br s, 1H), 8.05 (br t, J = 5.6 Hz, 1H), 8.27 (s, 1H). |

Example 72

Methyl 3-{2-[4-(1-aminocyclobutyl)phenyl]-3-phenylimidazo[1,2-b]pyridazin-8-yl}propanoate Step 1: Methyl (2E)-3-[6-bromo-2-(4-{1-[(tert-butoxycarbonyl)amino]cyclobutyl}phenyl)-3-phenylimidazo[1,2-b]pyridazin-8-yl]acrylate

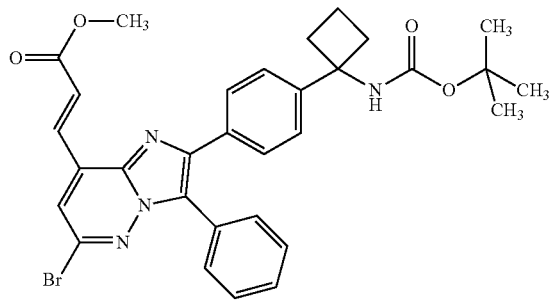 [SMILES: COC(=O)/C=C/c1cc(Br)nn2c(-c3ccccc3)c(-c3ccc(C4(NC(=O)OC(C)(C)C)CCC4)cc3)nc12]

A solution of tert-butyl (1-{4-[3-phenyl-6,8-dibromoimidazo[1,2-b]pyridazin-2-yl]phenyl}cyclobutyl)carbamate that was prepared in a manner analgous to that described for Intermediate Example Int-6 (0.50 g, 0.84 mmol), methyl acrylate (0.11 mL, 1.3 mmol, 1.5 equiv) and triethylamine (0.13 mL, 0.96 mmol, 1.1 equiv) in acetonitrile (6 mL) was placed under an argvon atmosphere. To this was added tri(2-tolyl)phosphine (0.043 g, 0.14 mmol, 0.17 equiv) and palladium(II) acetate (0.013 g, 0.059 mmol, 0.07 equiv). The resulting mixture was irradiated in a microwave apparatus at 150° C. for 60 min. The resulting mixture was then added to water (15 mL). The resulting mixture was extracted with EtOAc (2×25 mL). The combined organic phases were washed with water (25 mL), dried (Na$_2$SO$_4$), and concentrated under reduced pressure. The resulting material was purified using MPLC (Biotage Isolera; Snap 10 g cartridge, 100% hexane 1.5 min, gradient to 80% hexane/20% EtOAc 1.0 min, 80% hexane/20% EtOAc 2.0 min, gradient to 50% hexane/50% EtOAc 3.0 min, 50% hexane/50% EtOAc 4.0 min, gradient to 100% EtOAc 4.5 min, 100% EtOAc 7.7 min) to give methyl (2E)-3-[6-bromo-2-(4-{1-[(tert-butoxy-carbonyl)amino]cyclobutyl}phenyl)-3-phenylimidazo[1,2-b]pyridazin-8-yl]acrylate (0.50 g, 99%) which was used without further purification.

Step 2: Methyl 3-{2-[4-(1-aminocyclobutyl)phenyl]-3-phenylimidazo[1,2-b]-pyridazin-8-yl}propanoate

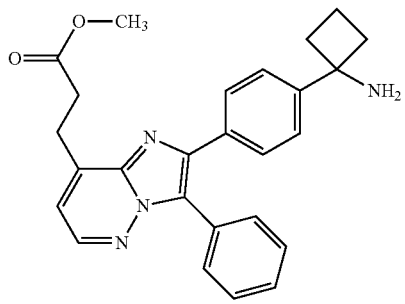 [SMILES: COC(=O)CCc1ccnn2c(-c3ccccc3)c(-c3ccc(C4(N)CCC4)cc3)nc12]

To a mixture of methyl (2E)-3-[6-bromo-2-(4-{1-[(tert-butoxycarbonyl)amino]cyclobutyl}phenyl)-3-phenylimidazo[1,2-b]pyridazin-8-yl]acrylate that was prepared in a manner analgous to that described for Example 72, Step 1 (0.50 g, 0.83 mmol) and 10% palladium on carbon (0.26 g) in a mixture of ethanol (14 mL) and THF (5 mL) was placed under a hydrogen atmosphere at room temperature for 1 h. The resulting mixture was treated with additional 10% palladium on carbon (0.26 g) and placed under a hydrogen atmosphere for 1 h. Solids were removed by filtration and washed with ethanol (20 mL). The combined organic solutions were treated with 10% palladium on carbon (0.26 g) and placed under a hydrogen atmosphere for 1 h. Solids were removed by filtration and washed with ethanol (20 mL). The combined organic solutions were concentrated under reduced pressure. The resulting material was purified using MPLC (Biotage Isolera; Snap 25 g cartridge, 100% hexane 2.0 min, gradient to 80% hexane/20% EtOAc 1.5 min, gradient to 74% hexane/26% EtOAc 2.5 min, gradient to 70% hexane/30% EtOAc 2.0 min, gradient to 50% hexane/50% EtOAc 3.0 min, 50% hexane/50% EtOAc 6.4 min, gradient to 25% hexane/75% EtOAc 3.5 min, 25% hexane/75% EtOAc 5.3 min gradient to 100% EtOAc 5.3 min, 100% EtOAc 21.2 min). The resulting material was further purified using preparative HPLC (Agilent Prep 1200 equipped with 2× Prep Pump, DLA, MWD, ELSD and Prep FC using an XBrigde C18 5 μm 100×30 mm column; gradient from 100% water with 0.1% HCO$_2$H to 70% water with 0.1% HCO$_2$H/30% MeOH over 1.0 min, gradient to 30% water with 0.1% HCO$_2$H/70% MeOH over 7.0 min, gradient to 100% MeOH over 0.1 min, 100% MeOH 1.9 min) to give methyl 3-{2-[4-(1-aminocyclobutyl)phenyl]-3-phenylimidazo[1,2-b]pyridazin-8-yl}propanoate (0.003 g, 1%):

UPLC-MS (Method 3): RT=0.97 min; m/z (rel intensity) 410 (500 (M+H-17)$^+$), 427 (60, (M+H)$^+$).

1H-NMR (CD$_3$OD): δ [ppm]1.76-1.89 (m, 1H), 2.04-2.18 (m, 1H), 2.30-2.41 (m, 2H), 2.58-2.69 (m, 2H), 2.97 (t, J=7.4 Hz, 2H), 3.40 (t, J=7.5 Hz, 2H), 3.68 (s, 3H), 7.10 (d, J=4.5 Hz, 1H), 7.41-7.47 (m, 5H), 7.48-7.53 (m, 2H), 7.65 (d, J=8.5 Hz, 2H), 8.29 (d, J=4.7 Hz, 1H).

Example 73

1-{4-[6-Methoxy-3-phenyl-8-(1H-pyrazol-3-yl)imidazo[1,2-b]pyridazin-2-yl]-phenyl}cyclobutanamine

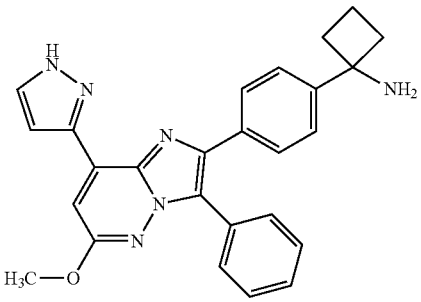 [SMILES: COc1cc(-c2cc[nH]n2)c2nc(-c3ccc(C4(N)CCC4)cc3)c(-c3ccccc3)n2n1]

To a solution of 1-{4-[6-chloro-3-phenyl-8-(1H-pyrazol-3-yl)imidazo[1,2-b]pyridazin-2-yl]phenyl}cyclobutanamine that was prepared in a manner analgous to that described for Example 19 (0.14 g, 0.32 mmol) and sodium methoxide (0.051 g, 0.95 mmol, 3.0 equiv) in MeOH (0.8 mL) was irradiated in a microwave apparatus at 120° C. for 90 min. The resulting mixture was added to water 10 mL. The aqueous mixture was extracted with DCM (3×15 mL), dried (Na$_2$SO$_4$ anh.) and concentrated under reduced pressure. The resulting material was purified using MPLC (Biotage Isolera; Snap 10 g cartridge, 100% hexane 2.0 min, gradient to 80% hexane/20% EtOAc 1.0 min, 80% hexane/20% EtOAc 3.0 min, gradient to 50% hexane/50% EtOAc 2.5 min, 50% hexane/50% EtOAc 3.5 min, gradient to 100% EtOAc 3.0 min, 100% EtOAc 4.8 min) to give an oil which was triturated with MeOH to give 1-{4-[6-methoxy-3-phenyl-8-(1H-pyrazol-3-yl)imidazo[1,2-b]pyridazin-2-yl]phenyl}cyclobutanamine (0.052 g, 36%):

UPLC-MS (Method 3): RT=1.37 min; m/z (rel intensity) 420 (100 (M+H-17)$^+$), 437 (60, (M+H)$^+$); ES- m/z (rel intensity) 435 (80, (M-H)$^-$).

1H-NMR (DMSO-d$_6$): δ [ppm]1.55-1.66 (m, 1H), 1.87-2.13 (m, 5H), 2.29-2.39 (m, 2H), 3.82 (s, 3H), 7.32 (s, 1H), 7.39 (d, J=8.5 Hz, 2H), 7.42-7.53 (m, 3H), 7.56-7.62 (m, 4H), 7.69 (d, J=2.1 Hz, 1H), 7.91 (br s, 1H).

The following examples were prepared in a manner analogous to Example 73 by the reaction of the sodium methoxide with the appropriate halide

| Example | Structure/Name | Characterization |
|---|---|---|
| 74 | 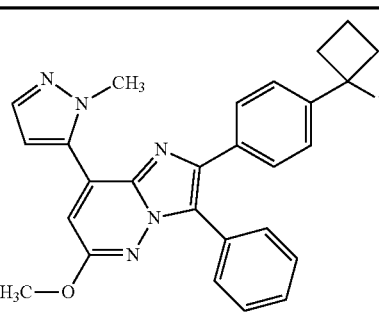<br>1-{4-[6-Methoxy-8-(1-methyl-1H-pyrazol-5-yl)-3-phenylimidazo[1,2-b]pyridazin-2-yl]phenyl}cyclobutanamine | UPLC-MS (Method 3): RT = 1.38 min; m/z (rel intensity) 434 (100 (M + H − 17)$^+$), 451 (80, (M + H)$^+$), 901 (20, (2M + H)$^+$). 1H-NMR (DMSO-d$_6$): δ [ppm] 1.51-1.65 (m, 1H), 1.85-2.15 (m, 5H), 2.27-2.37 (m, 2H), 3.84 (s, 3H), 4.02 (s, 3H), 6.92 (d, J = 1.9 Hz, 1H), 7.06 (s, 1H), 7.35 (d, J = 8.5 Hz, 2H), 7.43-7.53 (m, 5H), 7.57-7.62 (m, 3H). |
| 75 | 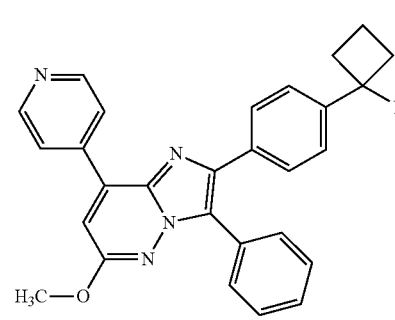<br>1-{4-[6-Methoxy-3-phenyl-8-(pyridin-4-yl)imidazo[1,2-b]pyridazin-2-yl]phenyl}cyclobutanamine | 1H-NMR (DMSO-d$_6$): δ [ppm] 1.60-1.65 (m, 1H), 1.93-2.02 (m, 1H), 2.05-2.14 (m, 4H), 2.35-2.41 (m, 2H), 3.90 (s, 3H), 7.43 (d, J = 8.5 Hz, 2H), 7.46 (s, 1H), 7.48-7.59 (m, 5H), 7.65 (dM, J = 7.3 Hz, 2H), 8.41 (d, J = 6.3 Hz, 2H), 8.83 (d, J = 6.3 HZ, 2H). |

The following examples were prepared in a manner analogous to Example 73 by the reaction of the sodium ethoxide with the appropriate halide

| Example | Structure/Name | Characterization |
|---|---|---|
| 76 | 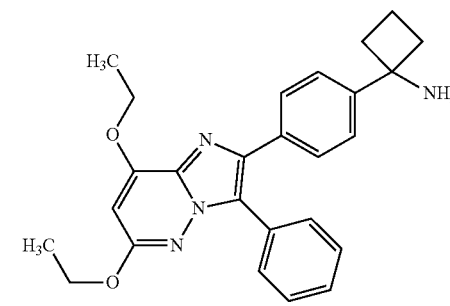<br>1-[4-(6,8-Diethoxy-3-phenylimidazo[1,2-b]pyridazin-2-yl)phenyl]cyclobutanamine | UPLC-MS (Method 3): RT = 1.46 min; m/z (rel intensity) 412 (100 (M + H − 17)$^+$), 429 (90, (M + H)$^+$), 857 (50, (2M + H)$^+$). 1H-NMR (DMSO-d$_6$): δ [ppm] 1.27 (t, J = 7.1 Hz, 3H), 1.43 (t, J = 7.1 HZ, 3H), 1.56-1.64 (m, 1H), 1.89-2.09 (m, 5H), 2.28-2.36 (m, 2H), 4.15 (q, J = 7.1 Hz, 2H), 4.32 (q, J = 7.1 Hz, 2H), 6.36 (s, 1H), 7.34 (d, J = 8.6 Hz, 2H), 7.38-7.48 (m, 5H), 7.52 (dm, J = 8.1 Hz, 2H). |

Example 77

1-[4-(8-Butoxy-6-ethoxy-3-phenylimidazo[1,2-b]pyridazin-2-yl)phenyl]-cyclobutanamine

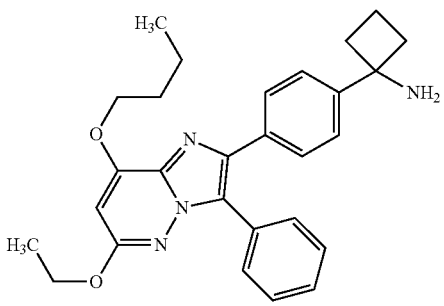 [SMILES: CCCCOc1cc(OCC)nn2c(-c3ccccc3)c(-c3ccc(C4(N)CCC4)cc3)nc12]

A mixture of ethyl {1-[4-(6,8-diethoxy-3-phenylimidazo[1,2-b]pyridazin-2-yl)phenyl]cyclobutyl}carbamate (0.12 g, 0.24 mmol) and potassium hydroxide (powder, 0.077 g, 1.17 mmol, 5.0 equiv) in n-butanol (2.5 mL) was heated at the reflux temperature for 24 h. The resulting mixture was cooled to room temperature and separated between a 4:1 DCM/isopropanol solution (50 mL) and water 50 mL). The organic phase was washed with a saturated aqueous NaCl solution (25 mL), dried (Na$_2$SO$_4$ anh.) and concentrated under reduced pressure. The resulting material was purified using MPLC (Biotage Isolera; SNAP 10 g cartridge: 100% DCM 4.0 min., gradient to 95% DCM/5% MeOH 1 min., 95% DCM/5% MeOH 3.5 min., gradient to 90% DCM/10% MeOH 1 min., 90% DCM/10% MeOH 3.5 min., gradient to 80% DCM/20% MeOH 6 min., 80% DCM/20% MeOH 4.7 min.) to give 1-[4-(8-butoxy-6-ethoxy-3-phenylimidazo[1,2-b]pyridazin-2-yl)phenyl]cyclobutanamine (0.013 g, 9%):

1H-NMR (DMSO-d$_6$): δ [ppm]0.97 (t, J=7.5 Hz, 3H), 1.30 (t, J=7.0 Hz, 3H), 1.49 (sext, J=7.5 Hz, 2H), 1.56-1.67 (m, 1H), 1.83 apparent (pent, J=7.0 Hz, 2H), 1.91-2.24 (m, 5H), 2.31-2.39 (m, 2H), 4.17 (q, J=7.3 Hz, 2H), 4.30 (t, J=6.6 Hz, 2H), 6.40 (s, 1H), 7.37 (d, J=8.5 Hz, 2H), 7.40-7.50 (m, 5H), 7.53-7.56 (m, 2H).

Example 78

1-[4-(6-Ethoxy-3-phenylimidazo[1,2-b]pyridazin-2-yl)phenyl]cyclobutanamine

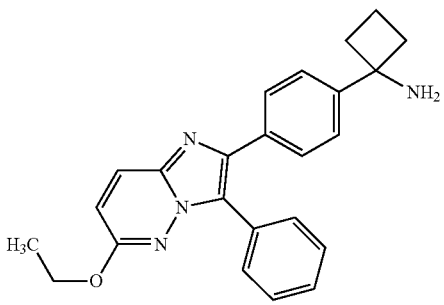 [SMILES: CCOc1ccc2nc(-c3ccc(C4(N)CCC4)cc3)c(-c3ccccc3)n2n1]

A mixture of tert-butyl {1-[4-(6-chloro-3-phenylimidazo[1,2-b]pyridazin-2-yl)phenyl]cyclobutyl}carbamate that was prepared in a manner analgous to that described for Intermediate Example Int-6.2 (0.050 g, 0.11 mmol) and potassium hydroxide (powder, 0.050 g, 0.89 mmol, 8.5 equiv) in ethanol (0.8 mL) was irradiated in a microwave apparatus at 120° C. for 120 min. The resulting mixture was added to ice water (10 mL). The aqueous mixture was extracted with a 4:1 DCM/isopropanol solution (4×10 mL). The combined organic phases were dried (Na$_2$SO$_4$ anh.) and concentrated under reduced pressure. The resulting material was purified using MPLC (Biotage Isolera; SNAP 10 g cartridge: 100% DCM 4.0 min., gradient to 95% DCM/5% MeOH 1 min., 95% DCM/5% MeOH 3.5 min., gradient to 90% DCM/10% MeOH 1 min., 90% DCM/10% MeOH 3.5 min., gradient to 80% DCM/20% MeOH 6 min., 80% DCM/20% MeOH 4.7 min.) to give 1-[4-(6-ethoxy-3-phenylimidazo[1,2-b]pyridazin-2-yl)phenyl]cyclobutanamine (0.017 g, 42%):

UPLC-MS (Method 3): RT=1.39 min; m/z (rel intensity) 368 (100 (M+H-17)$^+$), 385 (80, (M+H)$^+$), 769 (10, (2M+H)$^+$).

1H-NMR (DMSO-d$_6$): δ [ppm]1.28 (t, J=7.0 Hz, 3H), 1.53-1.65 (m, 1H), 1.87-2.08 (m, 5H), 2.27-2.33 (m, 2H), 4.18 (q, J=7.0 Hz, 2H), 6.88 (d, J=9.6 Hz, 1H), 1H), 7.35 (d, J=8.5 Hz, 2H), 7.41-7.56 (m, 7H), 8.03 (d, J=9.6 Hz, 1H).

Example 79

2-[4-(1-Aminocyclobutyl)phenyl]-3-phenylimidazo[1,2-b]pyridazin-6-ol

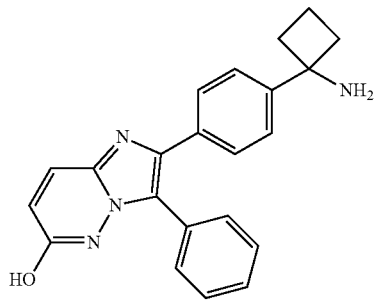 [SMILES: NC1(c2ccc(-c3nc4ccc(O)nn4c3-c3ccccc3)cc2)CCC1]

A mixture of tert-butyl (1-{4-[3-phenyl-6-methoxyimidazo[1,2-b]pyridazin-2-yl]phenyl}cyclobutyl)carbamate that was prepared in a manner analogous to that described for Intermediate Example Int-5 (0.25 g, 0.53 mmol) in N-methylpyrrolidone (5 mL) was warmed to 100° C., then sodium sulfide (0.21 g, 2.66 mmol, 5.0 equiv) was added and the mixture was heated to 160° C. for 10 minutes. The resulting mixture was added to ice water (15 mL). The aqueous mixture was made acidic with an aqueous 2N HCl solution, then was buffered with a saturated aqueous sodium bicarbonate solution. The resulting precipitate was removed by filtration, washed with water, and dried at 50° C. under vacuum to give 2-[4-(1-Aminocyclobutyl)phenyl]-3-phenylimidazo[1,2-b]pyridazin-6-ol (0.10 g, 53%):

UPLC-MS (Method 3): RT=0.61 min; m/z (rel intensity) 340 (100 (M+H-17)$^+$), 357 (90, (M+H)$^+$), 713 (20, (2M+H)$^+$); ES– m/z (rel intensity) 355 (100, (M–H)$^-$), 711 (100, (2M–H)$^-$).

1H-NMR (DMSO-d$_6$): δ [ppm]1.55-1.66 (m, 1H), 1.86-1.99 (m, 1H), 2.20-2.11 (m, 2H), 2.30-2.38 (m, 2H), 6.70 (d, J=9.6 Hz, 1H), 7.32 (d, J=8.3 Hz, 2H), 7.38-7.49 (m, 7H), 7.88 (d, J=9.6 Hz, 1H).

Example 80

Methyl ({2-[4-(1-aminocyclobutyl)phenyl]-3-phenylimidazo[1,2-b]pyridazin-6-yl}oxy)acetate

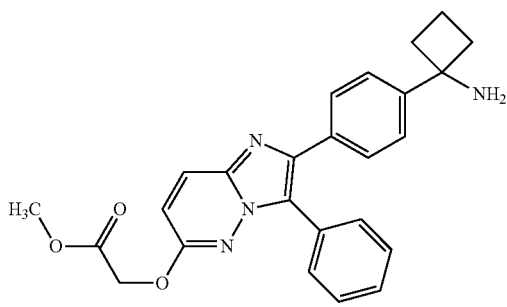 [SMILES: COC(=O)COc1ccc2nc(-c3ccc(C4(N)CCC4)cc3)c(-c3ccccc3)n2n1]

To a solution of 2-[4-(1-aminocyclobutyl)phenyl]-3-phenylimidazo[1,2-b]pyridazin-6-ol that was prepared in a manner analgous to that described for Example 79 (0.093 g, 0.26 mmol) in DMF (2.5 mL) was added cesium carbonate (0.26 g, 0.79 mmol, 3.0 equiv) and bromoacetic acid methyl ester (0.03 mL, 0.31 mmol, 1.20 equiv). The resulting mixture was stirred at room temperature for 1 h, then was warmed to 60° C. for 3 h. The resulting mixture was diluted with water (10 mL). The aqueous mixture was extracted with EtOAC (3×10 mL). The combined organic phases were dried ($Na_2SO_4$ anh.) and concentrated under reduced pressure. The resulting material was further purified using preparative HPLC (Agilent Prep 1200 equipped with 2× Prep Pump, DLA, MWD, ELSD and Prep FC using an XBrigde C18 5 µm 100×30 mm column; gradient from 100% water with 0.1% $HCO_2H$ to 70% water with 0.1% $HCO_2H$/30% MeOH over 1.0 min, gradient to 30% water with 0.1% $HCO_2H$/70% MeOH over 7.0 min, gradient to 100% MeOH over 0.1 min, 100% MeOH 1.9 min) to give methyl ({2-[4-(1-aminocyclobutyl)phenyl]-3-phenylimidazo[1,2-b]pyridazin-6-yl}oxy)acetate (0.056 g, 49%):

UPLC-MS (Method 3): RT=1.21 min; m/z (rel intensity) 412 (100 (M+H-17)$^+$), 429 (60, (M+H)$^+$), 857 (10, (2M+H)$^+$).

1H-NMR (DMSO-$d_6$): δ [ppm]1.54-1.68 (m, 1H), 1.86-2.11 (m, 3H), 2.30-2.39 (m, 2H), 3.56 (s, 3H), 4.81 (s, 2H), 7.03 (d, J=9.6 Hz, 1H), 7.37 (d, J=8.5 Hz, 2H), 7.41-7.47 (m, 5H), 7.52 (d, J=8.5 Hz, 2H), 8.12 (d, J=9.6 Hz, 1H).

Biological Investigations

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Biological Assay 1.0: Akt1 Kinase Assay

Akt1 inhibitory activity of compounds of the present invention was quantified employing the Akt1 TR-FRET assay as described in the following paragraphs.

His-tagged human recombinant kinase full-length Akt1 expressed in insect cells was purchased form Invitrogen (part number PV 3599). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt1 in assay buffer [50 mM TRIS/HCl pH 7.5, 5 mM $MgCl_2$, 1 mM dithiothreitol, 0.02% (v/v) Triton X-100 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt1 in the assay was adjusted depending of the activity of the enzyme lot and was chosen appropriate to have the assay in the linear range, typical enzyme concentrations were in the range of about 0.05 ng/µl (final conc. in the 5 µl assay volume). The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5). The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

Biological Assay 2.0: Akt2 Kinase Assay

Akt2 inhibitory activity of compounds of the present invention was quantified employing the Akt2 TR-FRET assay as described in the following paragraphs.

His-tagged human recombinant kinase full-length Akt2 expressed in insect cells and activated by PDK1 was purchased form Invitrogen (part number PV 3975). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of Akt2 in assay buffer [50 mM TRIS/HCl pH 7.5, 5 mM $MgCl_2$, 1 mM dithiothreitol, 0.02% (v/v) Triton X-100 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt2 in the assay was adjusted depending of the activity of the enzyme lot and was chosen appropriate to have the assay in the linear range, typical enzyme concentrations were in the range of about 0.2 ng/µl (final conc. in the 5 µl assay volume). The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5). The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100-fold conc. stock solutions by serial 1:3 dilutions) in duplicate values for each concentration and $IC_{50}$ values were calculated by a 4 parameter fit using an in-house software.

Preferred compounds of the present invention show in either the Akt1 or Akt2 kinase assay: median $IC_{50}$<5 µM or greater than 50% inhibition at 5 µM, more preferably, median $IC_{50}$<0.5 µM or greater than 50% inhibition at 0.5 µM, even more preferably, median $IC_{50}$≤0.1 µM or greater than 50% inhibition at 0.1 µM.

The following Table gives selected data for selected Examples of the present invention.

| Example | Akt1 median $IC_{50}$ (nM) | Akt2 median $IC_{50}$ (nM) |
|---|---|---|
| 1 | 170.0 | 380.0 |
| 2 | 65.0 | 97.0 |
| 3 | 120.0 | 70.0 |
| 4 | 85.0 | 190.0 |
| 5 | 5.2 | 18.0 |
| 6 | 4.2 | 80.0 |
| 7 | 6.9 | 9.7 |
| 8 | 450.0 | 400.0 |
| 9 | 3.9 | 18.0 |
| 10 | 2.6 | 4.1 |
| 11 | 130.0 | 110.0 |
| 12 | 21.0 | 38.0 |
| 13 | 78.0 | 42.0 |
| 14 | 9.8 | 65.0 |
| 15 | 4.4 | 56.0 |
| 16 | 160.0 | 160.0 |
| 17 | 43.0 | 92.0 |
| 18 | 86.0 | 53.0 |
| 19 | 15.0 | 42.0 |
| 20 | 120.0 | 170.0 |
| 21 | 73.0 | 130.0 |
| 22 | 8.0 | 18.0 |
| 23 | 1200.0 | 190.0 |
| 24 | 35.0 | 81.0 |
| 25 | 190.0 | 160.0 |
| 26 | 6.3 | 10.0 |
| 27 | 15.0 | 29.0 |
| 28 | 5.0 | 5.4 |
| 29 | 56.0 | 78.0 |
| 30 | 51.0 | 58.0 |
| 31 | 48.0 | 140.0 |
| 32 | 3700.0 | 3300.0 |
| 33 | 690.0 | Not tested |
| 34 | 3.9 | 14.0 |
| 35 | 350.0 | 1200.0 |
| 36 | 17.0 | 54.0 |
| 37 | 580.0 | 510.0 |
| 38 | 370.0 | 140.0 |
| 39 | 38.0 | 160.0 |
| 40 | 1700.0 | 1400.0 |
| 41 | 33.0 | 66.0 |
| 42 | 20000.0 | 20000.0 |
| 43 | 36.0 | 110.0 |
| 44 | 190.0 | 310.0 |
| 45 | 1200.0 | 6600.0 |
| 46 | 110.0 | 85.0 |
| 47 | 220.0 | 350.0 |
| 48 | 180.0 | 610.0 |
| 49 | 68.0 | 120.0 |
| 50 | 44.0 | 27.0 |
| 51 | 42.0 | 81.0 |
| 52 | 26.0 | 15.0 |
| 53 | 9.2 | 2.4 |
| 54 | 12.0 | 35.0 |
| 55 | 45.0 | 56.0 |
| 56 | 6.6 | 16.0 |
| 57 | 25.0 | 29.0 |
| 58 | 110.0 | 280.0 |
| 59 | 65.0 | 110.0 |
| 60 | 7.2 | 24.0 |
| 61 | 4.1 | 3.7 |
| 62 | 16.0 | 62.0 |
| 63 | 46.0 | 120.0 |
| 64 | 4.8 | 12.0 |
| 65 | 3.1 | 2.6 |
| 66 | 51.0 | 180.0 |
| 67 | 58.0 | 96.0 |
| 68 | 21.0 | 66.0 |
| 69 | 310.0 | 750.0 |
| 70 | 130.0 | 110.0 |
| 71 | 11.0 | 20.0 |
| 72 | 310.0 | 580.0 |
| 73 | 4.3 | 43.0 |
| 74 | 96.0 | 120.0 |
| 75 | 21.0 | 100.0 |
| 76 | 11.0 | 23.0 |
| 77 | 10.0 | 61.0 |
| 78 | 32.0 | 230.0 |

| Example | Akt1 median IC$_{50}$ (nM) | Akt2 median IC$_{50}$ (nM) |
|---|---|---|
| 79 | 2000.0 | 2800.0 |
| 80 | 96.0 | 610.0 |

Cellular Assays 3.0: p-AKT1/2/3-S473, -T308, and p-4E-BP1-T70 Assays

The molecular mechanism of action was investigated in a set of experiments to assess the inhibition of the PI3K-AKT-mTOR pathway in responsive cell lines such as KPL-4 breast tumour cell line (PIK3CA$^{H1047R}$, HER2$^{O/E}$ and hormone independent). The phospho-substrates of PI3K-AKT-mTOR axis were used as the read-outs to reflect pathway inhibition. Cells were seeded at 60-80% confluency per well in 96-well cell culture plates. After overnight incubation at 37° C. 5% CO2, cells were treated with compounds and vehicle at 37° C. for 2 hours. Thereafter, cells were lysed in 150 μl lysis buffer and the levels of phospho-AKT at T308 and S473 and p-4E-BP1 at T70 sites were determined with the corresponding AlphaScreen® SureFire® assay kits (Perkin Elmer: 4E-BP1 Assay Kit Cat #TRG4E2S1K; Akt 1/2/3 p-Ser 473 #TGRA4S500 and Akt 1/2/3 p-Thr 308 #TGRA3S500 as well as IgG detection Kit #6760617M) as described in the manuals. All measurements where at least done in duplicates and confirmed by independent repetition.

Alternatively pAKT-S473 was measured using the "Akt Duplex" of the MULTI-SPOT® Assay System (Fa. Meso Scale Discovery, Cat#N41100B-1) following manufacturers instructions. Each assay used 20 μg of protein extract and measured total AKT and p-AKT content simultaneously in one well. All measurements where at least done in duplicates and confirmed by independent repetition. Values for P-AKT are expressed as percentage of P-AKT level compared to total-AKT content of the extracts.

The following Table gives selected data for selected Examples of the present invention.

| Example | pAKT-S743 median IC$_{50}$ (nM) | P4EBP1-T70 median IC$_{50}$ (nM) |
|---|---|---|
| 1 | 160.0 | Not tested |
| 2 | 310.0 | 2100.0 |
| 3 | 360.0 | 4500.0 |
| 4 | 610.0 | 2400.0 |
| 5 | 0.9 | 35.0 |
| 6 | 210.0 | 1300.0 |
| 7 | 27.0 | 1300.0 |
| 8 | >10000.0 | >10000.0 |
| 9 | 36.0 | 690.0 |
| 10 | 2.4 | 28.0 |
| 11 | 14.0 | 160.0 |
| 12 | 52.0 | 260.0 |
| 13 | 82.0 | 660.0 |
| 14 | 220.0 | 320.0 |
| 15 | 590.0 | 1700.0 |
| 16 | 520.0 | 2500.0 |
| 17 | 12.0 | 430.0 |
| 18 | 180.0 | 710.0 |
| 19 | 390.0 | 5100.0 |
| 20 | 520.0 | 1500.0 |
| 21 | 420.0 | 1700.0 |
| 22 | 0.3 | 23.0 |
| 23 | 1400.0 | 2900.0 |
| 24 | 200.0 | 500.0 |
| 25 | 90.0 | 550.0 |
| 26 | 0.9 | 90.0 |
| 27 | 36.0 | 480.0 |
| 28 | 1.0 | 6.2 |
| 29 | 210.0 | 1300.0 |
| 30 | 400.0 | 2500.0 |
| 31 | 1800.0 | 4300.0 |
| 32 | 160.0 | 2200.0 |
| 33 | 2900.0 | Not tested |
| 34 | 3.1 | 150.0 |
| 35 | 190.0 | 1700.0 |
| 36 | 26.0 | 1600.0 |
| 37 | 81.0 | 2500.0 |
| 38 | 20.0 | 530.0 |
| 39 | 280.0 | 7500.0 |
| 40 | 2000.0 | 6100.0 |
| 41 | >10000.0 | >10000.0 |
| 42 | 120.0 | 2600.0 |
| 43 | 96.0 | 1600.0 |
| 44 | 800.0 | 380.0 |
| 45 | >10000.0 | >10000.0 |
| 46 | 430.0 | 300.0 |
| 47 | 140.0 | 96.0 |
| 48 | 42.0 | 29.0 |
| 49 | 8.0 | 41.0 |
| 50 | 450.0 | 2000.0 |
| 51 | 590.0 | 1200.0 |
| 52 | 2.1 | 9.9 |
| 53 | 200.0 | 1000.0 |
| 54 | 690.0 | 1600.0 |
| 55 | 680.0 | 1800.0 |
| 56 | 570.0 | 360.0 |
| 57 | 250.0 | 1800.0 |
| 58 | 1000.0 | 10000.0 |
| 59 | 11.0 | 100.0 |
| 60 | 1.0 | 8100.0 |
| 61 | 0.5 | 2.0 |
| 62 | 0.4 | 35.0 |
| 63 | 3.8 | 0.3 |
| 64 | 0.9 | 84.0 |
| 65 | 1.4 | 22.0 |
| 66 | 17.0 | 180.0 |
| 67 | >10000.0 | >10000.0 |
| 68 | 3.7 | 5300.0 |
| 69 | 250.0 | 4400.0 |
| 70 | 5.7 | 2400.0 |
| 71 | 92.0 | 10000.0 |
| 72 | 1000.0 | 590.0 |
| 73 | 230.0 | 1700.0 |
| 74 | 450.0 | 1200.0 |
| 75 | 230.0 | 1500.0 |
| 76 | 120.0 | 940.0 |
| 77 | 460.0 | 1400.0 |
| 78 | 92.0 | 580.0 |
| 79 | 210.0 | 910.0 |
| 80 | 190.0 | 9800.0 |

Biological Assay 4.0: Tumor Cell Proliferation Assays

Compounds were tested in a cell-based assay that measures the capacity of the compounds to inhibit tumour cell proliferation following a 72 h drug exposure. Cell viability is determined using CellTiter-Glow® (CTG, Promega, cat#G7571/2/3). The CellTiter-Glo® Luminescent Cell Viability Assay is a homogeneous method to determine the number of viable cells in culture.

Detection is based on using the luciferase reaction to measure the amount of ATP from viable cells. The amount of ATP in cells correlates with cell viability. Within minutes after a loss of membrane integrity, cells lose the ability to synthesize ATP, and endogenous ATPases destroy any remaining ATP; thus the levels of ATP fall precipitously.

Cells were plated at 3000-5000 cells/well (depending on the cell lines) in 90 μL growth medium on MTPs (Corning; #3603, black plate, clear flat bottom). For each cell line assayed, cells were plated onto a separate plate for determination of fluorescence at t=0 hour and t=72 hour time points. Following overnight incubation at 37° C., chemiluminescence values for the t=0 samples were determined after adding 10 µl medium and 100 µl CTG solution according to manufacture protocol. Plates for the t=72 hour time points were treated with compounds diluted into growth medium at ten times final concentration added in 10 µL to the cell culture plate. Cells were then incubated for 72 hours at 37° C. Chemiluminescence values for the t=72 hour samples were determined. For data analysis, briefly, data from 24 h plate where used to reflect 100% inhibition of growth ("Ci") and DMSO control for uninhibited growth ("C0") and analyzed using MTS software package for $IC_{50}$ and Hill coefficient. Experiments were controlled using a reference compound as standard.

Preferred compounds of the present invention show in this assay an inhibition of cell growth of cell lines such as the KPL-4 breast cancer cell line MCF-7 breast tumour cell line (PIK3CA$^{E542K;E545K}$, hormone dependent) and LNCaP prostate tumour cell line with a median $IC_{50}$ of <10 µM, more preferably, median IC50≤1 µM.

The following Table gives selected data for selected Examples of the present invention.

| Example | KLP-4 median $IC_{50}$ (nM) | MCF-7 median $IC_{50}$ (nM) |
|---|---|---|
| 1 | 1800.0 | 600.0 |
| 2 | 1700.0 | 1700.0 |
| 3 | 1700.0 | 1800.0 |
| 4 | 2400.0 | 1800.0 |
| 5 | 170.0 | 63.0 |
| 6 | 1100.0 | 1200.0 |
| 7 | 250.0 | 410.0 |
| 8 | >10000.0 | >10000.0 |
| 9 | 770.0 | 340.0 |
| 10 | 49.0 | 39.0 |
| 11 | 630.0 | 470.0 |
| 12 | 2000.0 | 1800.0 |
| 13 | 1500.0 | 1100.0 |
| 14 | 1900.0 | 1800.0 |
| 15 | 1800.0 | 1800.0 |
| 16 | 2000.0 | 1800.0 |
| 17 | Not tested | Not tested |
| 18 | 1600.0 | 1100.0 |
| 19 | 2000.0 | 1800.0 |
| 20 | 2600.0 | 1800.0 |
| 21 | 2000.0 | 1800.0 |
| 22 | 190.0 | 240.0 |
| 23 | 2200.0 | 2100.0 |
| 24 | 1700.0 | 1800.0 |
| 25 | 2000.0 | 1900.0 |
| 26 | 1800.0 | 1800.0 |
| 27 | 1800.0 | 1800.0 |
| 28 | 1900.0 | 1800.0 |
| 29 | 2000.0 | 1700.0 |
| 30 | 6000.0 | 2600.0 |
| 31 | 8400.0 | 1400.0 |
| 32 | Not tested | Not tested |
| 33 | Not tested | Not tested |
| 34 | 1100.0 | 330.0 |
| 35 | 6100.0 | 3000.0 |
| 36 | 1800.0 | 1700.0 |
| 37 | 3200.0 | 2000.0 |
| 38 | 740.0 | 510.0 |
| 39 | >10000.0 | 6100.0 |
| 40 | >10000.0 | 8400.0 |
| 41 | >10000.0 | >10000.0 |
| 42 | 2800.0 | 4200.0 |
| 43 | 6200.0 | 6700.0 |
| 44 | 2000.0 | 1900.0 |
| 45 | >10000.0 | >10000.0 |
| 46 | 1900.0 | 1500.0 |
| 47 | 1700.0 | 1100.0 |
| 48 | 1100.0 | 1300.0 |
| 49 | 140.0 | 610.0 |
| 50 | 1700.0 | 1800.0 |
| 51 | 7000.0 | 1400.0 |
| 52 | 140.0 | 110.0 |
| 53 | 1700.0 | 870.0 |
| 54 | 740.0 | 1800.0 |
| 55 | 2000.0 | 1900.0 |
| 56 | 8200.0 | 1100.0 |
| 57 | 9400.0 | 2100.0 |
| 58 | >10000.0 | >10000.0 |
| 59 | Not tested | Not tested |
| 60 | 1500.0 | 73.0 |
| 61 | 33.0 | 56.0 |
| 62 | Not tested | Not tested |
| 63 | 1600.0 | 760.0 |
| 64 | 360.0 | 150.0 |
| 65 | 470.0 | 280.0 |
| 66 | 2500.0 | 980.0 |
| 67 | Not tested | Not tested |
| 68 | 1500.0 | 680.0 |
| 69 | 10000.0 | 1500.0 |
| 70 | 2600.0 | 940.0 |
| 71 | 2000.0 | 780.0 |
| 72 | 2200.0 | 3000.0 |
| 73 | 1800.0 | 2000.0 |
| 74 | 2100.0 | 2000.0 |
| 75 | 1800.0 | 1800.0 |
| 76 | 1700.0 | 940.0 |
| 77 | 1900.0 | 1700.0 |
| 78 | Not tested | Not tested |
| 79 | 10000.0 | 10000.0 |
| 80 | 10000.0 | 10000.0 |

Example 5.0

Caco2 Permeability Assay

Caco-2 cells (purchased from DSMZ Braunschweig, Germany) were seeded at a density of 4.5×10$^4$ cell per well on 24 well insert plates, 0.4 µm pore size, and grown for 15 days in DMEM medium supplemented with 10% fetal bovine serum, 1% GlutaMAX (100×, GIBCO), 100 U/ml penicillin, 100 µg/ml streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by a FCS-free hepes-carbonate transport puffer (pH 7.2) For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app} = (V_r/P_o)(1/S)(P_2/t)$$

Where $V_r$ is the volume of medium in the receiver chamber, $P_o$ is the measured peak area of the test drug in the donor chamber at t=0, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B-A by the $P_{app}$ A-B. In addition the compound recovery was calculated. As assay control reference compounds were analyzed in parallel.

Example 6.0

In Vivo Rat Pharmacokinetics

For in vivo pharmacokinetic experiments test compounds were administered to male Wistar rats intravenously at doses of 0.5 to 1 mg/kg and intragastral at doses of 1 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

The person skilled in the art will be aware of methods to show in vivo efficacy of anti-cancer compounds. By way of illustration, the following example describes methods of quantifying the in vivo efficacy in a mouse xenograft model. The skilled person will be able to apply such principles to derive models from alternative tumor material.

Example 7.0

In Vivo Xenograft Mechanism of Action Study

To demonstrate that compounds act in tumours by the anticipated mode of action phosphorylation of the AKT protein was investigated in KPL-4 breast tumours treated once with 50 mg/kg compound.

To this extent KPL-4 human breast tumours were xenografted onto athymic nude mice. KPL-4 tumour cells were cultivated according to ATCC protocols in recommended media contained 10% FCS and harvested for transplantation in a subconfluent (70%) state. $3\times10^6$ tumour cells suspended in 50% Matrigel were subcutaneously implanted into the inguinal region of female mice. Tumours were allowed to grow to the predetermined size of 60-80 $mm^2$. When the tumours were approximately in size, the animals were randomized to treatment and control groups (groups size: 9 animals) and treatment was started. Animals were treated once with 50 mg/kg compound or vehicle per oral administration (p.o.) carried out via a gastric tube. Treatment of each animal was based on individual body weight. At 2, 5 and 24 hours post treatment 3 animals each were sacrificed and the KPL-4 tumours excised. Tumour samples of approximately 5×5×5 mm were lysed on ice in MSD lysis buffer in the presence of protease and phosphatase inhibitors using Tissue Lyzer (Qiagen, Germany). The levels of p-AKT S473 in extracts from tumour tissue were analysed in an ELISA based assay. This assay is based on the "Akt Duplex" of the MULTI-SPOT® Assay System (Fa. Meso Scale Discovery, Cat#N41100B-1) following manufacturers instructions. Each assay used 20 μg of protein extract and measured total AKT and p-AKT content simultaneously in one well. All measurements where at least done in duplicates and confirmed by independent repetition.

Values for P-AKT are expressed as percentage of P-AKT level compared to total-AKT content of the extracts. Vehicle treated tumours were analyzed to determine the basal level of P-AKT in this model and used as a normalization control to determine the % P-AKT relative to vehicle levels.

Preferred compounds of the present invention show in this assay: relative to vehicle levels P-AKT<30% at 2 hours post treatment, more preferably at 5 hours post treatment, even more preferably at 24 hours post treatment.

Example 7.1

In Vivo Xenograft Efficacy Study

To determine the therapeutic efficacy and tolerability of compounds, tumour growth of KPL-4 breast tumours xenografted onto nude mice may be observed. Mice were treated either with vehicle or compounds.

To this extent KPL-4 xenografts were established as described above. Tumours were allowed to grow to the predetermined size of 25-35 $mm^2$. When the tumours were approximately in size, the animals were randomized to treatment and control groups (groups size: 8 animals) and treatment was started. Treatment of each animal was based on individual body weight and oral administration (p.o.) was carried out via a gastric tube. The oral application volumes were 10 ml/kg for mice. Mice were treated once daily with 50 mg/kg compounds.

Tumour response was assessed by determination of the tumour area (product of the longest diameter and its perpendicular) using a calliper. The animal body weight was monitored as a measure for treatment-related toxicity. Measurement of tumour area and body weight were performed 2-3 times weekly. Statistical analysis was assessed using the SigmaStat software. A one way analysis of variance was performed, and differences to the control were compared by

The invention claimed is:

1. A method for the treatment of a cancer that is responsive to inhibition of an AKT kinase in a mammal in need thereof comprising administering to the mammal a therapeutically effective amount of a compound of formula (I)

(I)

[Chemical structure showing an azetidine ring with Y-X, connected to a carbon bearing NH₂ and a phenyl group, which is attached to an imidazo-pyridazine core bearing substituents R1, R2, R3, R4]

in which

R1 is hydrogen, hydroxy, NR5R6, halogen, cyano, CO(NR8R9), C(O)OR8, C(O)(1-6C-alkyl), NHC(O)(1-6C-alkyl), NHS(O)₂R11, NHC(O)NHR11, —S(O)ₙ-1-6C-alkyl, —S(O)₂NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl,
  wherein said group being optionally substituted, one or more times, identically or differently, with a substituent selected from:
  hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-cycloalkyl, 3-7C-heterocyclyl, aryl, R2 is hydrogen, hydroxy, NR5R6, halogen, cyano, CO(NR8R9), C(O)OR8, C(O)(1-6C-alkyl), NHC(O)(1-6C-alkyl), NHS(O)₂R11, NHC(O)NHR11, —S(O)ₙ-1-6C-alkyl, —S(O)₂NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl,
  wherein said group being optionally substituted, one or more times, identically or differently, with a substituent selected from:
  hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-heterocyclyl, aryl, R3 is hydrogen, hydroxy, NR5R6, halogen, cyano, CO(NR8R9), C(O)OR8, C(O)(1-6C-alkyl), NHS(O)₂R11, NHC(O)NHR11, —S(O)ₙ-1-6C-alkyl, —S(O)₂NR5R6 or a group selected from 1-6C-alkyl, 1-6C-alkoxy 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, NHC(O)(1-6C-alkyl),
  wherein said group being optionally substituted, one or more times, identically or differently, with a substituent selected from:
  hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-heterocyclyl, aryl, R4 is phenyl which is optionally substituted one, two or three times, identically or differently, with a halogen atom;

R5 is hydrogen, 1-6C-alkyl,

R6 is hydrogen, 1-6C-alkyl,

R8 is hydrogen, 1-6C-alkyl which optionally is substituted with hydroxy,

R9 is hydrogen, 1-6C-alkyl,

R10 is hydrogen, 1-6C-alkyl,

R11 is hydrogen, 1-6C-alkyl,

X, Y is CH₂;

n is 0, 1, 2;

or an N-oxide, a salt, a tautomer or a stereoisomer of said compound, or a salt of said N-oxide, tautomer or stereoisomer.

2. A method for inhibiting AKT kinase activity in cells in a mammal in need thereof comprising administering to the mammal a therapeutically effective amount of a compound of formula (I)

(I)

[Chemical structure same as above]

in which

R1 is hydrogen, hydroxy, NR5R6, halogen, cyano, CO(NR8R9), C(O)OR8, C(O)(1-6C-alkyl), NHC(O)(1-6C-alkyl), NHS(O)₂R11, NHC(O)NHR11, —S(O)ₙ-1-6C-alkyl, —S(O)₂NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl,
  wherein said group being optionally substituted, one or more times, identically or differently, with a substituent selected from:
  hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-cycloalkyl, 3-7C-heterocyclyl, aryl, R2 is hydrogen, hydroxy, NR5R6, halogen, cyano, CO(NR8R9), C(O)OR8, C(O)(1-6C-alkyl), NHC(O)

(1-6C-alkyl), NHS(O)₂R11, NHC(O)NHR11, —S(O)$_n$-1-6C-alkyl, —S(O)₂NR5R6 or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-heterocyclyl, aryl, R3 is hydrogen, hydroxy, NR5R6, halogen, cyano, CO(NR8R9), C(O)OR8, C(O)(1-6C-alkyl), NHS(O)₂R11, NHC(O)NHR11, —S(O)$_n$-1-6C-alkyl, —S(O)₂NR5R6 or a group selected from 1-6C-alkyl, 1-6C-alkoxy 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl, NHC(O)(1-6C-alkyl), 2-6C-alkenyl, 2-6C-alkynyl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHC(O)NHR11, —NHS(O)₂R11, 3-7C-heterocyclyl, aryl, R4 is phenyl which is optionally substituted one, two or three times, identically or differently, with a halogen atom;

R5 is hydrogen, 1-6C-alkyl,
R6 is hydrogen, 1-6C-alkyl,
R8 is hydrogen, 1-6C-alkyl which optionally is substituted with hydroxy,
R9 is hydrogen, 1-6C-alkyl,
R10 is hydrogen, 1-6C-alkyl,
R11 is hydrogen, 1-6C-alkyl,
X, Y is CH₂;
n is 0, 1, 2;
or an N-oxide, a salt, a tautomer or a stereoisomer of said compound, or a salt of said N-oxide, tautomer or stereoisomer.

3. The method as in claim 1 or 2,
wherein
R1 is hydrogen, hydroxy, NR5R6, halogen, cyano, CO(NR8R9), C(O)OR8, C(O)(1-3C-alkyl), NHC(O)(1-6C-alkyl), NHS(O)₂R11, NHC(O)NHR11, —S(O)$_n$-1-3C-alkyl, —S(O)₂NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, 2-3C-alkenyl, 2-3C-alkynyl, wherein said group being optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)₂R11, 3-6-cycloalkyl, 3-6C-heterocyclyl, aryl, R2 is hydrogen, hydroxy, NR5R6, halogen, cyano, CO(NR8R9), C(O)OR8, C(O)(1-3C-alkyl), NHC(O)(1-3C-alkyl), NHS(O)₂R11, NHC(O)NHR11, —S(O)$_n$-1-3C-alkyl, —S(O)₂NR5R6 or a group selected from 1-3C-alkyl, 1-3C-alkoxy, 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, 2-3C-alkenyl, 2-3C-alkynyl, wherein said group being optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)₂R11, 3-6C-heterocyclyl, aryl, R3 is hydrogen, hydroxy, NR5R6, halogen, cyano, CO(NR8R9), C(O)OR8, C(O)(1-3C-alkyl), NHS(O)₂R11, NHC(O)NHR11, —S(O)$_n$-1-3C-alkyl, —S(O)₂NR5R6 or a group selected from 1-3C-alkyl, 1-3C-alkoxy 3-6C-cycloalkyl, aryl, heteroaryl, -(1-3C-alkyl)-aryl, -(1-3C-alkyl)-heteroaryl, —O-(3-6C-cycloalkyl), —O-aryl, —O-(3-6C-heterocyclyl), —O-heteroaryl, —O-(1-3C-alkyl)-heteroaryl, —O-(1-3C-alkyl)-(3-6C-heterocyclyl), —O-(1-3C-alkyl)-aryl, NHC(O)(1-3C-alkyl), 2-3C-alkenyl, 2-3C-alkynyl, wherein said group being optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHC(O)NHR11, —NHS(O)₂R11, 3-6C-heterocyclyl, aryl, R4 is phenyl which is optionally substituted one, two or three times, identically or differently, with a halogen atom;

R5 is hydrogen, 1-3C-alkyl,
R6 is hydrogen, 1-3C-alkyl,
R8 is hydrogen, 1-3C-alkyl which optionally is substituted with hydroxy,
R9 is hydrogen, 1-3C-alkyl,
R10 is hydrogen, 1-3C-alkyl,
R11 is hydrogen, 1-3C-alkyl,
X, Y is CH₂;
n is 0, 1, 2;
or an N-oxide, a salt, a tautomer or a stereoisomer of said compound, or a salt of said N-oxide, tautomer or stereoisomer.

4. The method as in claim 1 or 2,
wherein
R1 is hydrogen, hydroxy, NR5R6, CO(NR8R9), C(O)OR8, NHC(O)(1-6C-alkyl), or a group selected from 1-6C-alkyl, 3-7C-cycloalkyl, aryl, heteroaryl, 1-4C-alkoxy, wherein said group being optionally substituted, one or more times, identically or differently, with a substituent selected from: halogen, 1-6C-alkyl, 1-6C-alkoxy, —C(O)OR10, 3-7-cycloalkyl, aryl, R2 is hydrogen, 1-6C-alkyl,
R3 is hydrogen, hydroxy, NR5R6, halogen, CO(NR8R9), C(O)OR8, C(O)(1-6C-alkyl), NHS(O)2R11, S(O)n-1-6C-alkyl, or a group selected from 1-6C-alkyl, 1-6C-alkoxy aryl, NHC(O)(1-6C-alkyl), 2-6C-alkenyl, wherein said group being optionally substituted, one or more times, identically or differently, with a substituent selected from: halogen, —C(O)OR10,
R4 is phenyl,
R5 is hydrogen,
R6 is hydrogen,
R8 is hydrogen, 1-4C-alkyl, which optionally is substituted with hydroxy,
R9 is hydrogen, 1-4C-alkyl,
R10 is, 1-4C-alkyl,
R11 is 1-4C-alkyl,
X, Y is CH$_2$
n is 0, 1, 2;
or an N-oxide, a salt, a tautomer or a stereoisomer of said compound, or a salt of said N-oxide, tautomer or stereoisomer.

5. A method as in claim 1 or 2,
wherein
R1 is hydrogen, hydroxyl, amino, methoxy, ethoxy, butoxy, pyridine-3-yl, pyridine-4-yl, pyrazol-3-yl, 1-methyl-pyrazol-3-yl, imidazole-2-yl, methyl, propyl, —O—(CH$_2$)—O—CH$_3$, —O—CH$_2$-phenyl, —O—CH$_2$-cyclopropyl, —C(O)OCH$_3$, —C(O)—NHCH$_3$, —C(O)—NH$_2$, 4-fluoro-phenyl, —(CH$_2$)$_2$—C(O)OCH$_3$, cyclopropyl, —NH—C(O)CH$_3$,
R2 is hydrogen, methyl,
R3 is hydrogen, hydroxy, amino, methyl, ethyl, methoxy, ethoxy, —O—CH$_2$—C(O)OCH$_3$, —S—CH$_3$, —SO$_2$—CH$_3$, bromine, chlorine, trifluoromethyl, C(O)NH$_2$, COOH, C(O)OCH$_3$, C(O)OCH$_2$CH$_3$, C(O)NH$_2$, C(O)NHCH$_3$, C(O)N(CH$_3$)$_2$, C(O)NH(CH$_2$)$_2$—OH, —CH=CH$_2$, 4-fluoro-phenyl, NHC(O)CH$_3$, NHC(O)CF$_3$, NH—SO$_2$—CH$_3$, C(O)CH$_3$,
R4 is phenyl
X, Y is CH2
or an N-oxide, a salt, a tautomer or a stereoisomer of said compound, or a salt of said N-oxide, tautomer or stereoisomer.

6. A method as in claim 1 or 2, wherein the compound of formula (I) is selected from the group consisting of 1-[4-(6-Methyl-3-phenylimidazo[1,2-b]pyridazin-2-yl)phenyl]-cyclobutanamine,
1-[4-(6-Ethyl-3-phenylimidazo[1,2-b]pyridazin-2-yl)phenyl]-cyclobutanamine,
1-{4-[3-Phenyl-6-(trifluoromethyl)imidazo[1,2-b]pyridazin-2-yl]phenyl}cyclobutanamine,
Ethyl 2-[4-(1-aminocyclobutyl)phenyl]-3-phenylimidazo[1,2-b]pyridazine-6-carboxylate,
2-[4-(1-Aminocyclobutyl)phenyl]-3-phenylimidazo[1,2-b]-pyridazine-6-carboxamide,
1-[4-(6-Methyloxy-3-phenylimidazo[1,2-b]pyridazin-2-yl)-phenyl]cyclobutanamine,
1-[4-(6-bromo-8-methyloxy-3-phenylimidazo[1,2-b]pyridazin-2-yl)phenyl]cyclobutanamine,
2-[4-(1-aminocyclobutyl)phenyl]-3-phenylimidazo[1,2-b]-pyridazine-6-carboxylic acid,
1-[4-(6,8-dimethyloxy-3-phenylimidazo[1,2-b]pyridazin-2-yl)-phenyl]cyclobutanamine,
2-[4-(1-aminocyclobutyl)phenyl]-8-methoxy-3-phenyl-imidazo[1,2-b]pyridazine-6-carboxamide,
1-[4-(8-Methoxy-3-phenylimidazo[1,2-b]pyridazin-2-yl)-phenyl]cyclobutanamine,
Methyl 2-[4-(1-aminocyclobutyl)phenyl]-8-methoxy-3-phenyl-imidazo[1,2-b]pyridazine-6-carboxylate,
1-[4-(6-Ethyl-8-methoxy-3-phenylimidazo[1,2-b]pyridazin-2-yl)phenyl]cyclobutanamine,
1-{4-[6-Methoxy-3-phenyl-8-(pyridin-3-yl)imidazo[1,2-b]-pyridazin-2-yl]phenyl}cyclobutanamine,
1-{4-[6-Methoxy-3-phenyl-8-(1H-pyrazol-4-yl)imidazo[1,2-b]-pyridazin-2-yl]phenyl}cyclobutanamine HCl salt, 1-[4-(6,8-Diethyl-3-phenylimidazo[1,2-b]pyridazin-2-yl)-phenyl]cyclobutanamine,
1-[4-(6-Chloro-3-phenylimidazo[1,2-b]pyridazin-2-yl)phenyl]-cyclobutanamine,
1-[4-(8-Methoxy-3-phenyl-6-vinylimidazo[1,2-b]pyridazin-2-yl)phenyl]cyclobutanamine,
1-{4-[6-Chloro-3-phenyl-8-(1H-pyrazol-3-yl)imidazo[1,2-b]pyridazin-2-yl]phenyl}cyclobutanamine,
1-{4-[3-Phenyl-8-(1H-pyrazol-3-yl)-6-vinylimidazo[1,2-b]pyridazin-2-yl]phenyl}cyclobutanamine,
1-{4-[6-Ethyl-3-phenyl-8-(1H-pyrazol-3-yl)imidazo[1,2-b]pyridazin-2-yl]phenyl}cyclobutanamine,
2-[4-(1-Aminocyclobutyl)phenyl]-8-ethoxy-N-methyl-3-phenylimidazo[1,2-b]pyridazine-6-carboxamide,
1-{4-[6-Chloro-8-(1-methyl-1H-pyrazol-5-yl)-3-phenylimidazo[1,2-b]pyridazin-2-yl]phenyl}cyclobutanamine,
1-{4-[6-Chloro-8-(1H-imidazol-2-yl)-3-phenylimidazo[1,2-b]pyridazin-2-yl]phenyl}cyclobutanamine,
1-[4-(3-Phenylimidazo[1,2-b]pyridazin-2-yl)phenyl]-cyclobutanamine,
2-[4-(1-Aminocyclobutyl)phenyl]-8-methoxy-N-methyl-3-phenylimidazo[1,2-b]pyridazine-6-carboxamide,
1-{4-[3-Phenyl-8-(1H-pyrazol-3-yl)imidazo[1,2-b]pyridazin-2-yl]phenyl}cyclobutanamine,
2-[4-(1-Aminocyclobutyl)phenyl]-8-(2-methoxyethoxy)-3-phenylimidazo[1,2-b]pyridazine-6-carboxamide,
1-{4-[8-(Benzyloxy)-6-chloro-3-phenylimidazo[1,2-b]-pyridazin-2-yl]phenyl}cyclobutanamine,
1-[4-(6-Chloro-8-ethoxy-3-phenylimidazo[1,2-b]pyridazin-2-yl)phenyl]cyclobutanamine,
Methyl 2-[4-(1-aminocyclobutyl)phenyl]-3-phenylimidazo[1,2-b]pyridazine-8-carboxylate,
2-[4-(1-Aminocyclobutyl)phenyl]-3-phenylimidazo[1,2-b]-pyridazin-8-ol,
1-{4-[6-(4-Fluorophenyl)-3-phenylimidazo[1,2-b]pyridazin-2-yl]phenyl}cyclobutanamine,
2-[4-(1-Aminocyclobutyl)phenyl]-3-phenylimidazo[1,2-b]-pyridazine-6,8-dicarboxamide,
2-[4-(1-Aminocyclobutyl)phenyl]-3-phenylimidazo[1,2-b]-pyridazin-6-amine,
1-{4-[6-(Methylsulfanyl)-3-phenylimidazo[1,2-b]pyridazin-2-yl]phenyl}cyclobutanamine,
N-{2-[4-(1-Aminocyclobutyl)phenyl]-3-phenylimidazo[1,2-b]-pyridazin-6-yl}acetamide,
N-{2-[4-(1-1-{4-[6-(Methylsulfonyl)-3-phenylimidazo[1,2-b]-pyridazin-2-yl]phenyl}cyclobutanamine,
Methyl 2-[4-(1-aminocyclobutyl)phenyl]-3-phenylimidazo[1,2-b]pyridazine-6-carboxylate,
N-{2-[4-(1-Aminocyclobutyl)phenyl]-3-phenylimidazo[1,2-b]-pyridazin-6-yl}-2,2,2-trifluoroacetamide,
1-[4-(6-Bromo-3-phenylimidazo[1,2-b]pyridazin-2-yl)phenyl]-cyclobutanamine,
1-{4-[6,8-Bis(4-fluorophenyl)-3-phenylimidazo[1,2-b]-pyridazin-2-yl]phenyl}cyclobutanamine,
1-{2-[4-(1-Aminocyclobutyl)phenyl]-3-phenylimidazo[1,2-b]-pyridazin-6-yl}ethanone,
1-{4-[8-(4-Fluorophenyl)-3-phenylimidazo[1,2-b]pyridazin-2-yl]phenyl}cyclobutanamine,
N-{2-[4-(1-Aminocyclobutyl)phenyl]-3-phenylimidazo[1,2-b]-pyridazin-6-yl}methanesulfonamide,
1-[4-(6-Chloro-8-cyclopropyl-3-phenylimidazo[1,2-b]-pyridazin-2-yl)phenyl]cyclobutanamine,
1-[4-(3-Phenyl-8-propylimidazo[1,2-b]pyridazin-2-yl)phenyl]-cyclobutanamine,
2-[4-(1-Aminocyclobutyl)phenyl]-3-phenylimidazo[1,2-b]-pyridazin-8-amine,
N-{2-[4-(1-Aminocyclobutyl)phenyl]-3-phenylimidazo[1,2-b]-pyridazin-8-yl}acetamide,
1-[4-(6-Chloro-7,8-dimethyl-3-phenylimidazo[1,2-b]pyridazin-2-yl)phenyl]cyclobutanamine,
Methyl 2-[4-(1-aminocyclobutyl)phenyl]-7,8-dimethyl-3-phenylimidazo[1,2-b]pyridazine-6-carboxylate,
2-[4-(1-Aminocyclobutyl)phenyl]-7,8-dimethyl-3-phenyl-imidazo[1,2-b]pyridazine-6-carboxamide,
1-[4-(6-Methoxy-7,8-dimethyl-3-phenylimidazo[1,2-b]-pyridazin-2-yl)phenyl]cyclobutanamine,
1-{4-[7,8-Dimethyl-6-(methylsulfanyl)-3-phenylimidazo[1,2-b]-pyridazin-2-yl]phenyl}cyclobutanamine, 1-[4-(6-Ethoxy-7,8-dimethyl-3-phenylimidazo[1,2-b]pyridazin-2-yl)phenyl]cyclobutanamine,
Methyl 2-[4-(1-aminocyclobutyl)phenyl]-3-phenyl-8-(1H-pyrazol-3-yl)imidazo[1,2-b]pyridazine-6-carboxylate,
Methyl 2-[4-(1-aminocyclobutyl)phenyl]-8-ethoxy-3-phenylimidazo[1,2-b]pyridazine-6-carboxylate,
Methyl 2-[4-(1-aminocyclobutyl)phenyl]-8-(1H-imidazol-2-yl)-3-phenylimidazo[1,2-b]pyridazine-6-carboxylate,
tert-Butyl {1-[4-(8-acetamido-3-phenylimidazo[1,2-b]pyridazin-2-yl)phenyl]cyclobutyl}carbamate,
2-[4-(1-Aminocyclobutyl)phenyl]-3-phenyl-8-(1H-pyrazol-3-yl)imidazo[1,2-b]pyridazine-6-carboxamide,
2-[4-(1-Aminocyclobutyl)phenyl]-8-ethoxy-3-phenylimidazo[1,2-b]pyridazine-6-carboxamide,
2-[4-(1-Aminocyclobutyl)phenyl]-8-(1H-imidazol-2-yl)-N-methyl-3-phenylimidazo[1,2-b]pyridazine-6-carboxamide,
2-[4-(1-Aminocyclobutyl)phenyl]-N-methyl-3-phenylimidazo[1,2-b]pyridazine-8-carboxamide,
2-[4-(1-Aminocyclobutyl)phenyl]-8-(cyclopropylmethoxy)-N-methyl-3-phenylimidazo[1,2-b]pyridazine-6-carboxamide,
2-[4-(1-Aminocyclobutyl)phenyl]-N-methyl-3-phenyl-8-(1H-pyrazol-3-yl)imidazo[1,2-b]pyridazine-6-carboxamide,
2-[4-(1-Aminocyclobutyl)phenyl]-N-ethyl-3-phenylimidazo[1,2-b]pyridazine-6-carboxamide,
2-[4-(1-Aminocyclobutyl)phenyl]-3-phenyl-8-(1H-pyrazol-3-yl)imidazo[1,2-b]pyridazine-6-carboxylic acid,
2-[4-(1-Aminocyclobutyl)phenyl]-N-methyl-3-phenyl-imidazo[1,2-b]pyridazine-6-carboxamide,
2-[4-(1-Aminocyclobutyl)phenyl]-N,N-dimethyl-3-phenyl-imidazo[1,2-b]pyridazine-6-carboxamide,
2-[4-(1-Aminocyclobutyl)phenyl]-N-(2-hydroxyethyl)-3-phenylimidazo[1,2-b]pyridazine-6-carboxamide,
2-[4-(1-Aminocyclobutyl)phenyl]-N-(2-hydroxyethyl)-3-phenyl-8-(1H-pyrazol-3-yl)imidazo[1,2-b]pyridazine-6-carboxamide,
Methyl 3-{2-[4-(1-aminocyclobutyl)phenyl]-3-phenyl-imidazo[1,2-b]pyridazin-8-yl}propanoate,
1-{4-[6-Methoxy-3-phenyl-8-(1H-pyrazol-3-yl)imidazo[1,2-b]pyridazin-2-yl]phenyl}cyclobutanamine,
1-{4-[6-Methoxy-8-(1-methyl-1H-pyrazol-5-yl)-3-phenyl-imidazo[1,2-b]pyridazin-2-yl]phenyl}cyclobutanamine,
1-{4-[6-Methoxy-3-phenyl-8-(pyridin-4-yl)imidazo[1,2-b]pyridazin-2-yl]phenyl}cyclobutanamine,
1-[4-(6,8-Diethoxy-3-phenylimidazo[1,2-b]pyridazin-2-yl)phenyl]cyclobutanamine,
1-[4-(8-Butoxy-6-ethoxy-3-phenylimidazo[1,2-b]pyridazin-2-yl)phenyl]cyclobutanamine,
1-[4-(6-Ethoxy-3-phenylimidazo[1,2-b]pyridazin-2-yl)phenyl]cyclobutanamine,
2-[4-(1-Aminocyclobutyl)phenyl]-3-phenylimidazo[1,2-b]pyridazin-6-ol, and
Methyl ({2-[4-(1-aminocyclobutyl)phenyl]-3-phenylimidazo-[1,2-b]pyridazin-6-yl}oxy)acetate.

* * * * *